United States Patent
Fujita et al.

(10) Patent No.: US 11,925,111 B2
(45) Date of Patent: *Mar. 5, 2024

(54) ORGANIC LIGHT EMITTING DEVICE

(71) Applicant: SAMSUNG DISPLAY CO., LTD., Yongin-si (KR)

(72) Inventors: Yoshimasa Fujita, Yokohama (JP); Shuri Sato, Yokohama (JP); Hiroaki Itoi, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/495,551

(22) Filed: Oct. 6, 2021

(65) Prior Publication Data

US 2022/0029102 A1 Jan. 27, 2022

Related U.S. Application Data

(63) Continuation of application No. 16/946,396, filed on Jun. 19, 2020, now Pat. No. 11,145,819, which is a
(Continued)

(30) Foreign Application Priority Data

Mar. 30, 2016 (KR) ........................ 10-2016-0038593

(51) Int. Cl.
*H01L 51/50* (2006.01)
*C07C 211/54* (2006.01)
(Continued)

(52) U.S. Cl.
CPC .......... *H10K 85/636* (2023.02); *C07C 211/54* (2013.01); *C07C 211/58* (2013.01);
(Continued)

(58) Field of Classification Search
None
See application file for complete search history.

(56) References Cited

U.S. PATENT DOCUMENTS

| 8,648,363 B2 | 2/2014 | Matsumoto et al. |
| 9,660,202 B2 | 5/2017 | Itoi et al. |

(Continued)

FOREIGN PATENT DOCUMENTS

| JP | H04-308688 A | 10/1992 |
| JP | 2004-231547 A | 8/2004 |

(Continued)

*Primary Examiner* — Gregory D Clark
(74) *Attorney, Agent, or Firm* — Lewis Roca Rothgerber Christie LLP

(57) ABSTRACT

An organic light emitting device including an anode; a hole transport region on the anode; an emission layer on the hole transport region; an electron transport region on the emission layer; and a cathode on the electron transport region, wherein the hole transport region includes: a first hole transport layer including a first hole transport material represented by the following Formula 1 or a second hole transport material represented by the following Formula 2; and a second hole transport layer on the first hole transport layer, the second hole transport layer including a third hole transport material represented by the following Formula 3 or a fourth hole transport material represented by the following Formula 4:

(Continued)

US 11,925,111 B2

Page 2

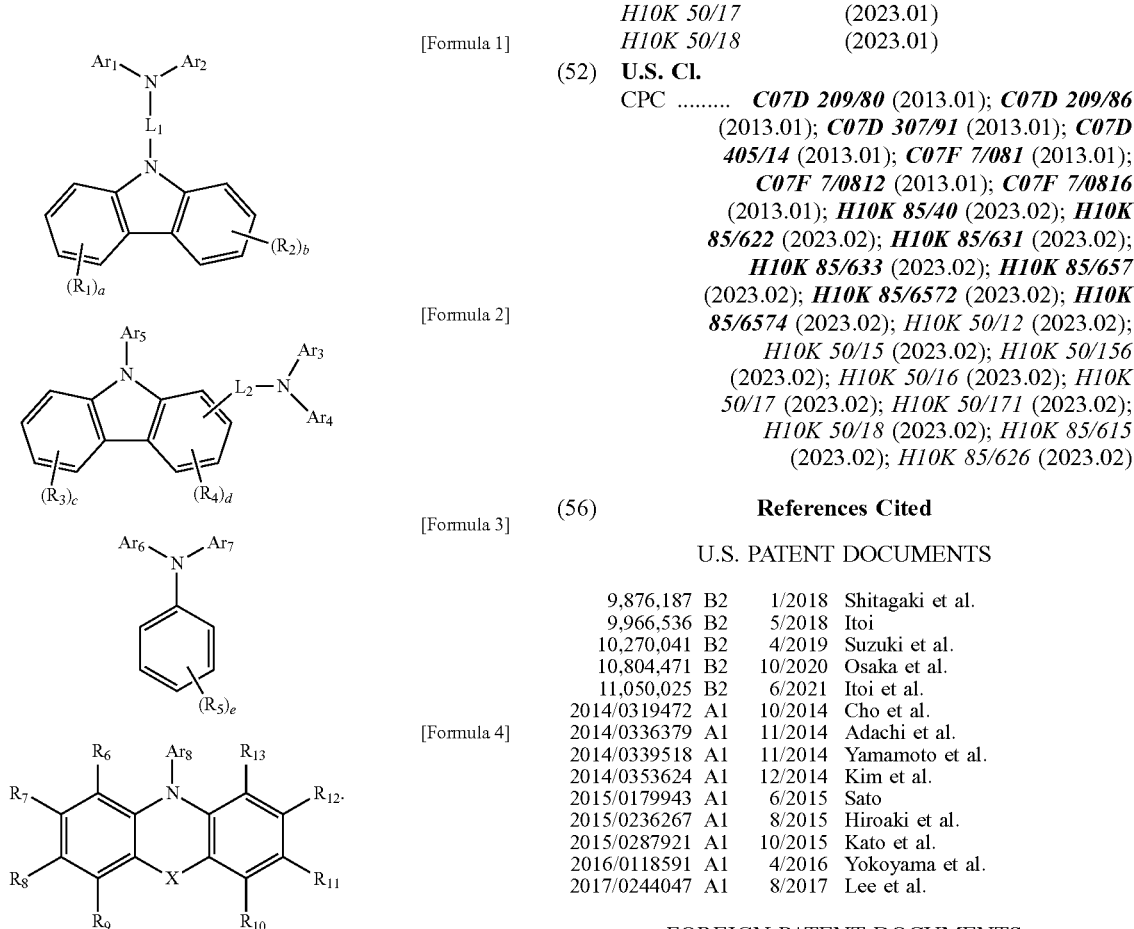

19 Claims, 1 Drawing Sheet

Related U.S. Application Data continuation of application No. 15/447,704, filed on Mar. 2, 2017, now Pat. No. 10,734,586.

(51) Int. Cl.
| | |
|---|---|
| C07C 211/58 | (2006.01) |
| C07D 209/80 | (2006.01) |
| C07D 209/86 | (2006.01) |
| C07D 307/91 | (2006.01) |
| C07D 405/14 | (2006.01) |
| C07F 7/08 | (2006.01) |
| H10K 85/40 | (2023.01) |
| H10K 85/60 | (2023.01) |
| H10K 50/12 | (2023.01) |
| H10K 50/15 | (2023.01) |
| H10K 50/16 | (2023.01) |
| H10K 50/17 | (2023.01) |
| H10K 50/18 | (2023.01) |

(52) U.S. Cl.
CPC ......... C07D 209/80 (2013.01); C07D 209/86 (2013.01); C07D 307/91 (2013.01); C07D 405/14 (2013.01); C07F 7/081 (2013.01); C07F 7/0812 (2013.01); C07F 7/0816 (2013.01); H10K 85/40 (2023.02); H10K 85/622 (2023.02); H10K 85/631 (2023.02); H10K 85/633 (2023.02); H10K 85/657 (2023.02); H10K 85/6572 (2023.02); H10K 85/6574 (2023.02); H10K 50/12 (2023.02); H10K 50/15 (2023.02); H10K 50/156 (2023.02); H10K 50/16 (2023.02); H10K 50/17 (2023.02); H10K 50/171 (2023.02); H10K 50/18 (2023.02); H10K 85/615 (2023.02); H10K 85/626 (2023.02)

(56) References Cited

U.S. PATENT DOCUMENTS

| | | | |
|---|---|---|---|
| 9,876,187 | B2 | 1/2018 | Shitagaki et al. |
| 9,966,536 | B2 | 5/2018 | Itoi |
| 10,270,041 | B2 | 4/2019 | Suzuki et al. |
| 10,804,471 | B2 | 10/2020 | Osaka et al. |
| 11,050,025 | B2 | 6/2021 | Itoi et al. |
| 2014/0319472 | A1 | 10/2014 | Cho et al. |
| 2014/0336379 | A1 | 11/2014 | Adachi et al. |
| 2014/0339518 | A1 | 11/2014 | Yamamoto et al. |
| 2014/0353624 | A1 | 12/2014 | Kim et al. |
| 2015/0179943 | A1 | 6/2015 | Sato |
| 2015/0236267 | A1 | 8/2015 | Hiroaki et al. |
| 2015/0287921 | A1 | 10/2015 | Kato et al. |
| 2016/0118591 | A1 | 4/2016 | Yokoyama et al. |
| 2017/0244047 | A1 | 8/2017 | Lee et al. |

FOREIGN PATENT DOCUMENTS

| | | |
|---|---|---|
| JP | 2009-099967 A | 5/2009 |
| JP | 2011-233855 A | 11/2011 |
| JP | 2012-507507 A | 3/2012 |
| JP | 2014-139156 A | 7/2014 |
| JP | 2015-092581 A | 5/2015 |
| JP | 2015-122459 A | 7/2015 |
| JP | 2015-128113 A | 7/2015 |
| JP | 2015-128115 A | 7/2015 |
| JP | 2015-154068 A | 8/2015 |
| JP | 5848480 B1 | 1/2016 |
| JP | 2017-76780 A | 4/2017 |
| KR | 10-2013-0106255 A | 9/2013 |
| KR | 10-1370183 B1 | 3/2014 |
| KR | 10-2014-0091487 A | 7/2014 |
| KR | 10-2015-0006694 A | 1/2015 |
| KR | 10-1493482 | 2/2015 |
| KR | 10-2015-0075352 A | 7/2015 |
| KR | 10-2015-0077269 A | 7/2015 |
| KR | 10-2015-0098181 A | 8/2015 |
| KR | 10-2016-0004513 A | 1/2016 |
| KR | 10-2016-0030429 A | 3/2016 |
| KR | 10-1684979 B1 | 12/2016 |
| WO | WO 2011/070963 A1 | 6/2011 |
| WO | WO 2014/128945 A1 | 8/2014 |
| WO | WO 2015/004875 A1 | 1/2015 |
| WO | WO 2016/009823 A1 | 1/2016 |

ORGANIC LIGHT EMITTING DEVICE

CROSS-REFERENCE TO RELATED APPLICATIONS

This application is a continuation of U.S. application Ser. No. 16/946,396, filed on Jun. 19, 2020, which is a continuation of U.S. application Ser. No. 15/447,704, filed on Mar. 2, 2017, now U.S. Pat. No. 10,734,586, which claims priority to and benefit of Korean Patent Application No. 10-2016-0038593, filed on Mar. 30, 2016, in the Korean Intellectual Property Office, the entire content of each of which is incorporated by reference herein.

BACKGROUND

1. Field

Embodiments relate to an organic light emitting device.

2. Description of the Related Art

Recently, the development of an organic light emitting display device as an image display device is being actively conducted. Different from a liquid crystal display device, the organic light emitting display device is a self-luminescent display device in which holes and electrons injected from an anode and a cathode recombine in an emission layer, and a luminescent material including an organic compound in the emission layer emits light to accomplish display.

As an organic light emitting device, an organic device may include, e.g., an anode, a hole transport region disposed on the anode, an emission layer disposed on the hole transport region, an electron transport region disposed on the emission layer, and a cathode disposed on the electron transport region. Holes are injected from the anode, and the injected holes move and are injected into the emission layer. Meanwhile, electrons are injected from the cathode, and the injected electrons move and are injected into the emission layer. The holes and electrons injected into the emission layer recombine to generate excitons in the emission layer. The organic light emitting device emits light using light generated by the radiation deactivation of the excitons. In addition, the organic light emitting device is not limited to the above-described configuration; and various modifications may be possible.

SUMMARY

Embodiments are directed to an organic light emitting device.

The embodiments may be realized by providing an organic light emitting device including an anode; a hole transport region on the anode; an emission layer on the hole transport region; an electron transport region on the emission layer; and a cathode on the electron transport region, wherein the hole transport region includes: a first hole transport layer including a first hole transport material represented by the following Formula 1 or a second hole transport material represented by the following Formula 2; and a second hole transport layer on the first hole transport layer, the second hole transport layer including a third hole transport material represented by the following Formula 3 or a fourth hole transport material represented by the following Formula 4:

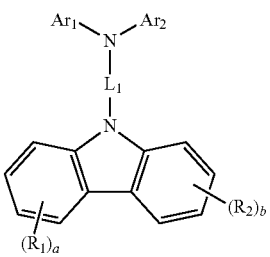

[Formula 1]

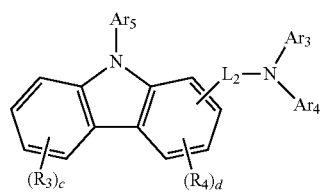

[Formula 2]

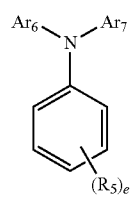

[Formula 3]

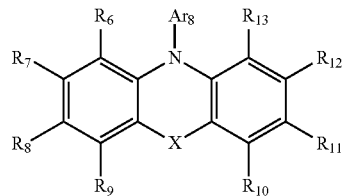

[Formula 4]

wherein, in Formulae 1, 2, 3 and 4, $Ar_1$, $Ar_2$, $Ar_3$, $Ar_4$, $Ar_5$, $Ar_6$, $Ar_7$, and $Ar_8$ are each independently a substituted or unsubstituted aryl group having 6 to 30 ring carbon atoms, a substituted or unsubstituted heteroaryl group having 5 to 30 ring carbon atoms, a substituted or unsubstituted alkyl group having 1 to 20 carbon atoms, a substituted or unsubstituted silyl group, a halogen atom, a deuterium atom, or a hydrogen atom, X is a direct linkage or $CR_{14}R_{15}$, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{15}$ are each independently a substituted or unsubstituted aryl group having 6 to 30 ring carbon atoms, a substituted or unsubstituted heteroaryl group having 5 to 30 ring carbon atoms, a substituted or unsubstituted alkyl group having 1 to 20 carbon atoms, a substituted or unsubstituted silyl group, a halogen atom, a deuterium atom, or a hydrogen atom, $L_1$ and $L_2$ are each independently a direct linkage, a substituted or unsubstituted alkyl group having 6 to 30 carbon atoms, a substituted or unsubstituted arylene group having 6 to 30 ring carbon atoms, or a substituted or unsubstituted heteroarylene group having 5 to 30 ring carbon atoms, a, b, and c are each independently an integer of 0 to 4, d is an integer of 0 to 3, and e is an integer of 0 to 5, in the case where e is an integer of 2 to 5, adjacent ones of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{15}$ are separate or are bound form a ring.

The emission layer may include an emission material containing a donor and an acceptor, the emission material being a thermally activated delayed fluorescence material.

The first hole transport layer may include the first hole transport material represented by Formula 1, and $Ar_1$ and $Ar_2$ in Formula 1 may include a substituted or unsubstituted phenyl group, a substituted or unsubstituted biphenyl group, a substituted or unsubstituted naphthyl group, a substituted or unsubstituted fluorenyl group, or a substituted or unsubstituted acridine group.

The first hole transport layer may include the first hole transport material represented by Formula 1, and $L_1$ in Formula 1 may include a substituted or unsubstituted phenylene group, a substituted or unsubstituted divalent biphenyl group, or a substituted or unsubstituted fluorenylene group.

The first hole transport layer may include the first hole transport material represented by Formula 1, and the first hole transport material may include one of the following Compounds:

1-1
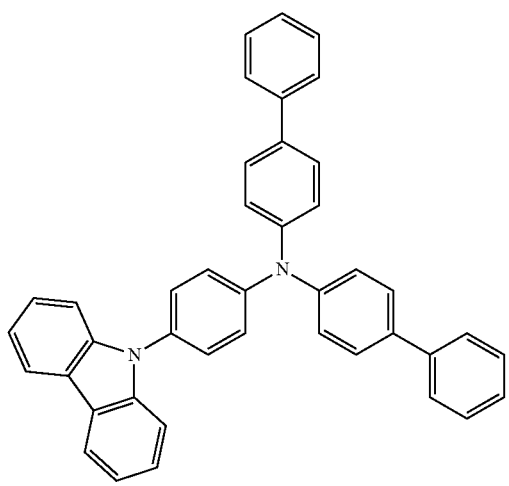

1-2
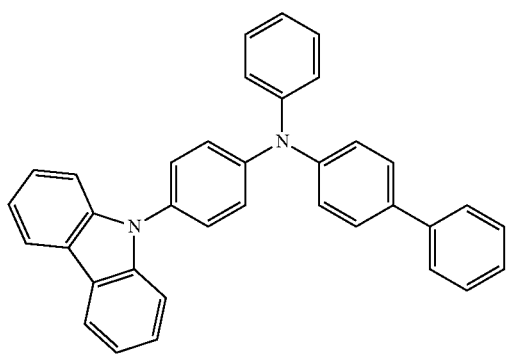

-continued 1-3
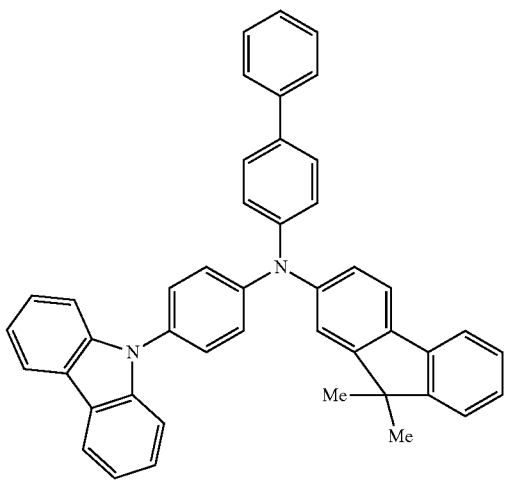

1-4
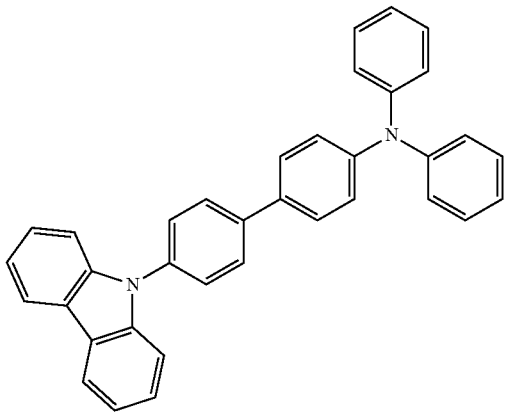

1-7
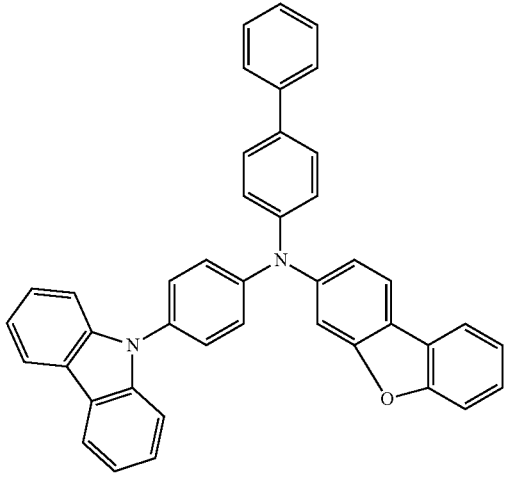

1-8
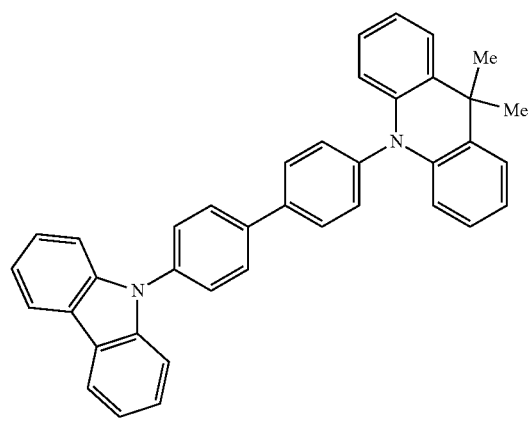
1-9
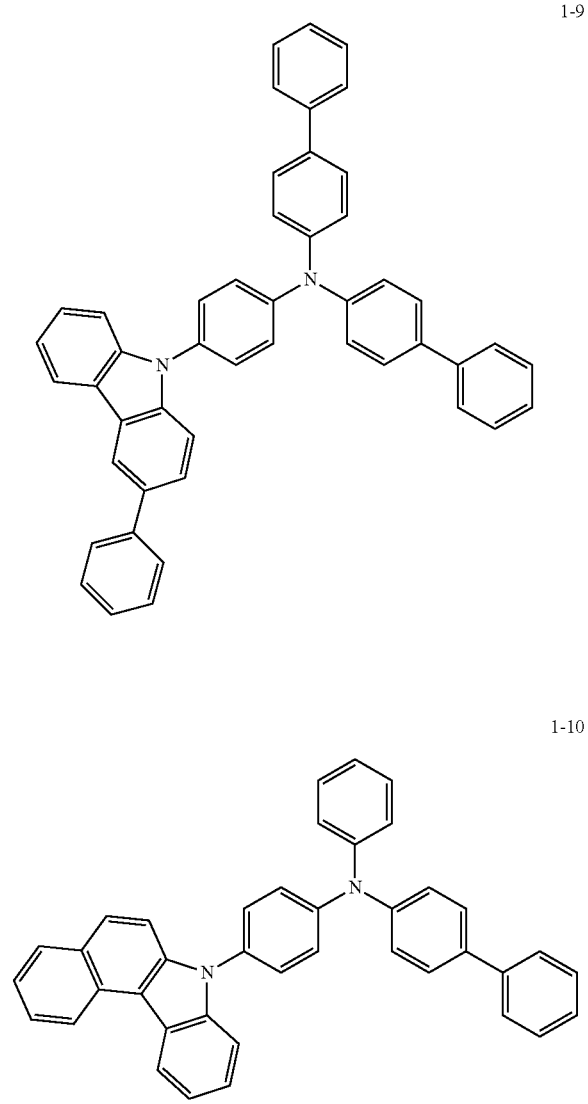
1-10
1-11
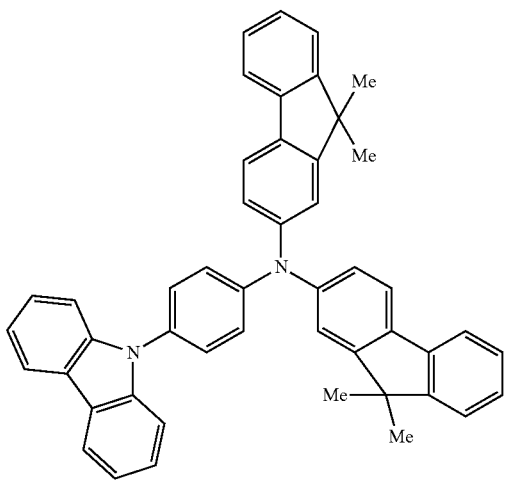
1-12
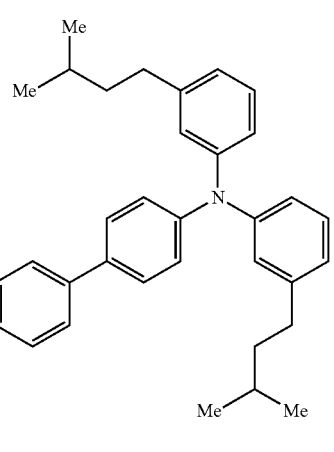
1-13
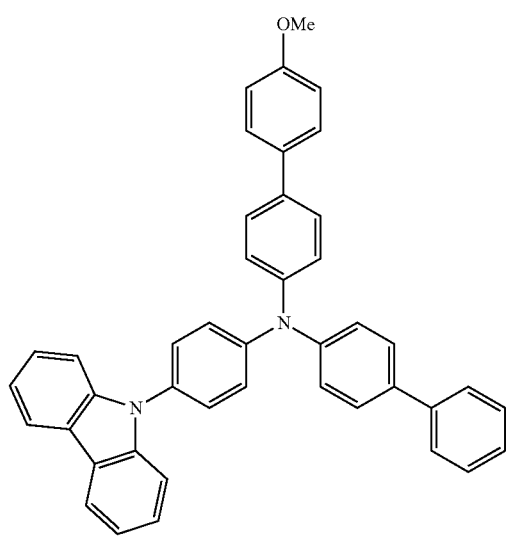

1-14
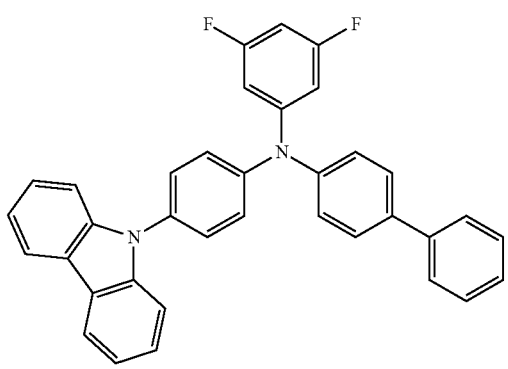
1-15
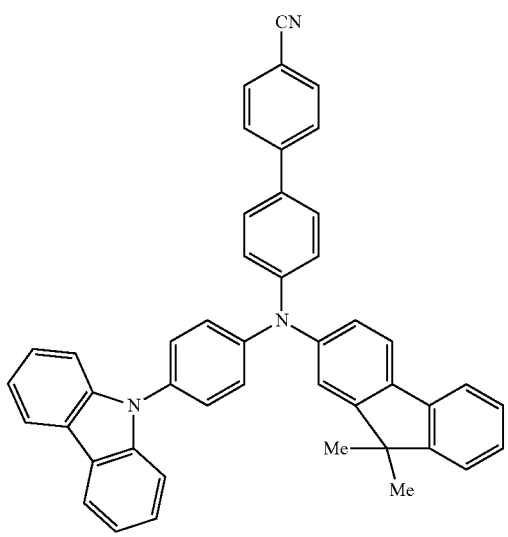
1-16
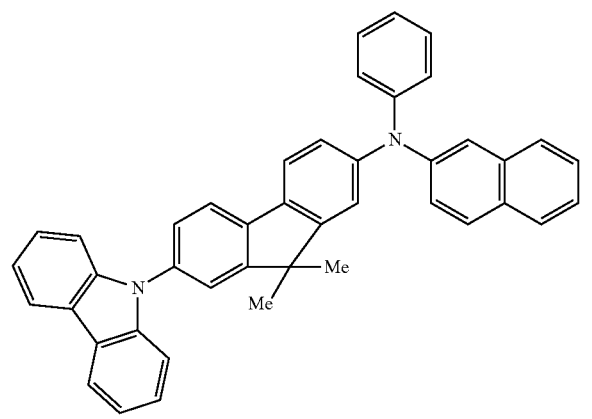
1-17
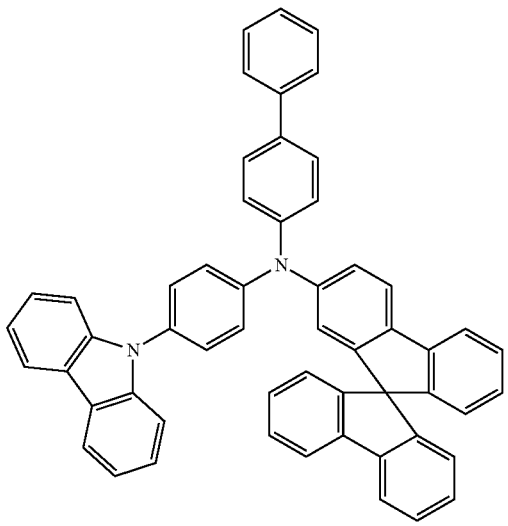
1-18
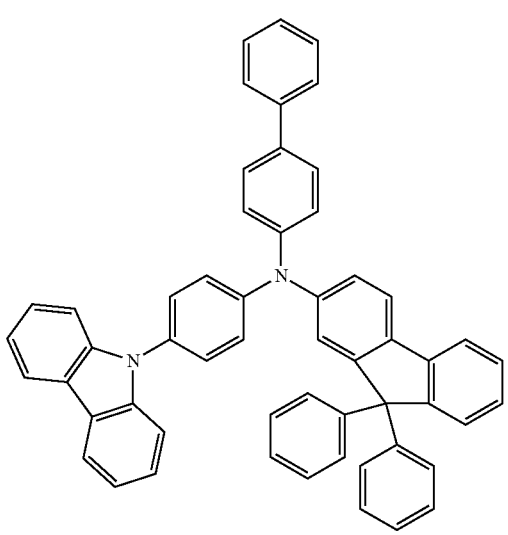
1-19
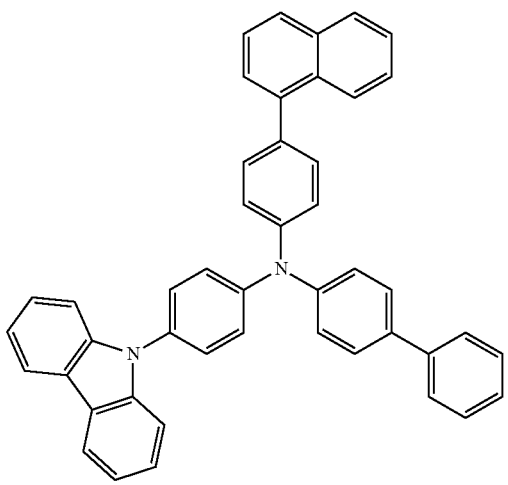

-continued 1-20

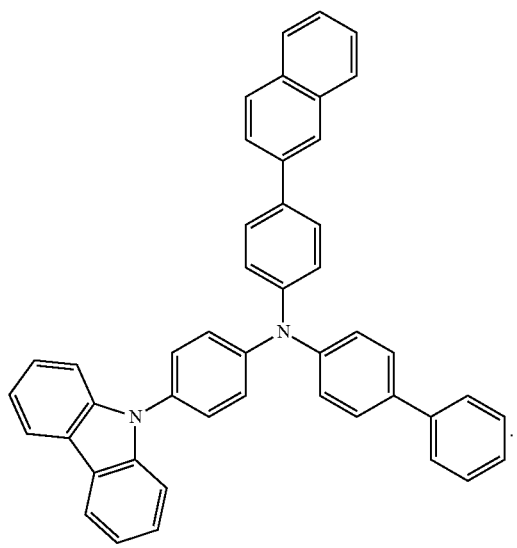

2-1

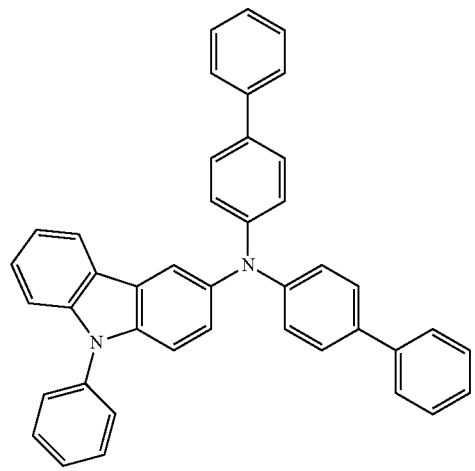

2-2

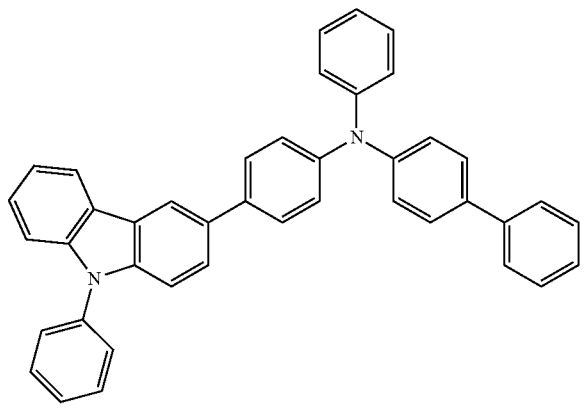

The first hole transport layer may include the second hole transport material represented by Formula 2, and $Ar_3$ and $Ar_4$ in Formula 2 may be bound to form a ring.

The first hole transport layer may include the second hole transport material represented by Formula 2, and $Ar_3$ and $Ar_4$ in Formula 2 may include a substituted or unsubstituted phenyl group, a substituted or unsubstituted biphenyl group, a substituted or unsubstituted naphthyl group, a substituted or unsubstituted fluorenyl group, or a substituted or unsubstituted spirobifluorenyl group.

The first hole transport layer may include the second hole transport material represented by Formula 2, and $Ar_5$ in Formula 2 may include a substituted or unsubstituted phenyl group, a substituted or unsubstituted dibenzofuran group, or a substituted or unsubstituted pyridine group.

The first hole transport layer may include the second hole transport material represented by Formula 2, and $L_2$ in Formula 2 may include a direct linkage, a substituted or unsubstituted phenylene group, a substituted or unsubstituted divalent biphenyl group, or a substituted or unsubstituted fluorenylene group.

The first hole transport layer may include the second hole transport material represented by Formula 2, and the second hole transport material may include one of the following Compounds 2-1 to 2-20:

2-3

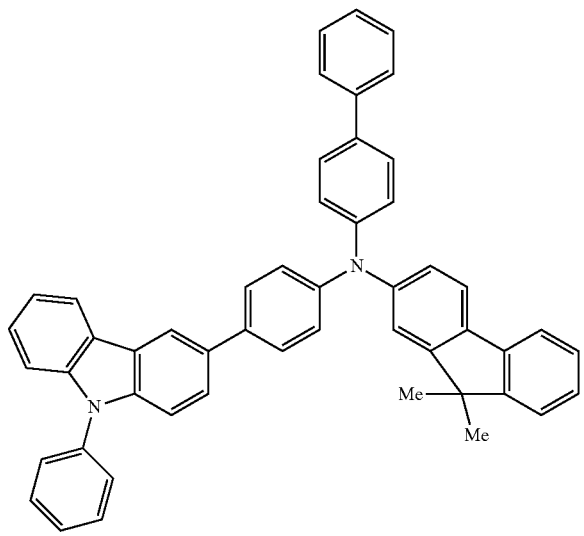

2-4
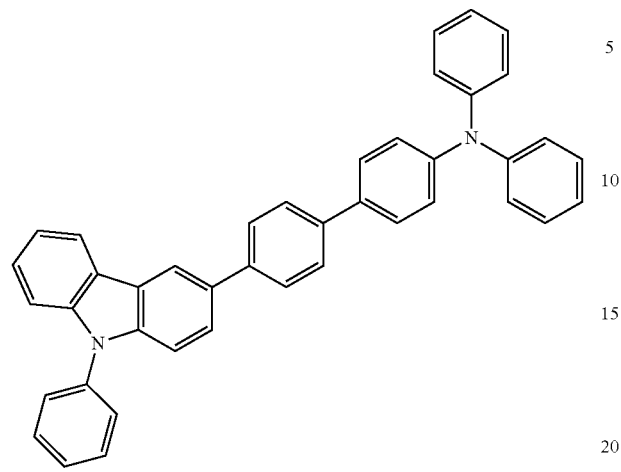
2-5
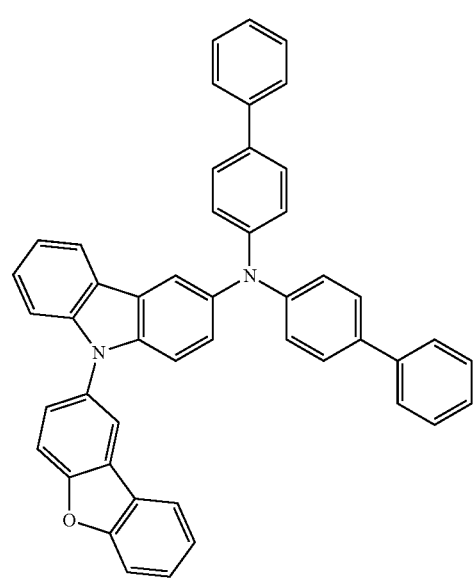
2-6
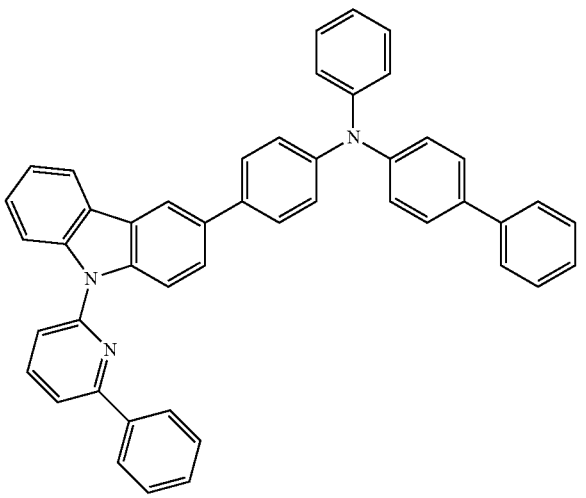
2-7
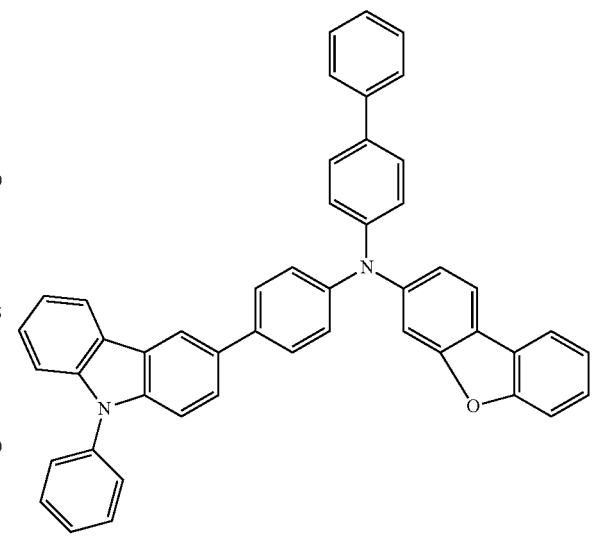
2-8
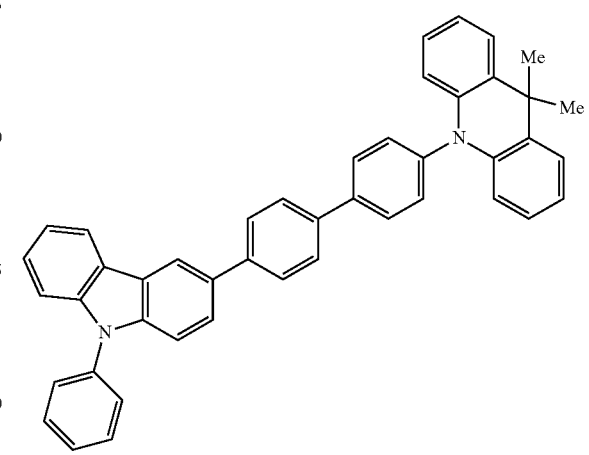
2-9
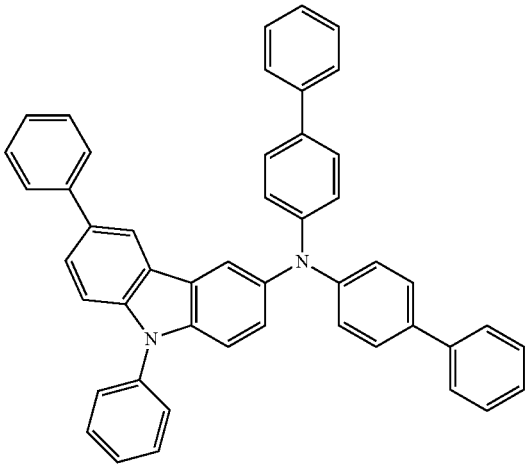

2-10
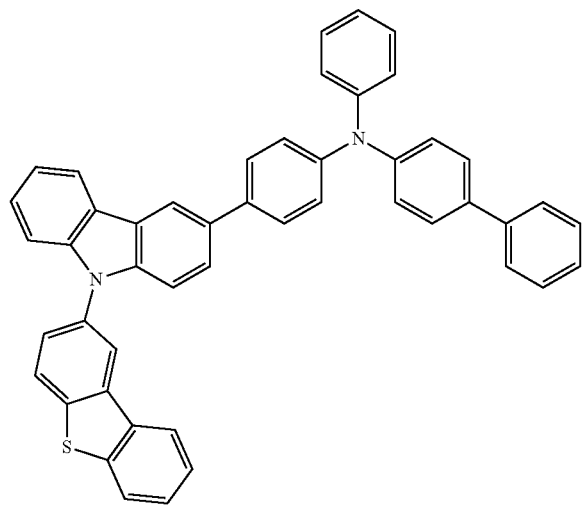
2-11
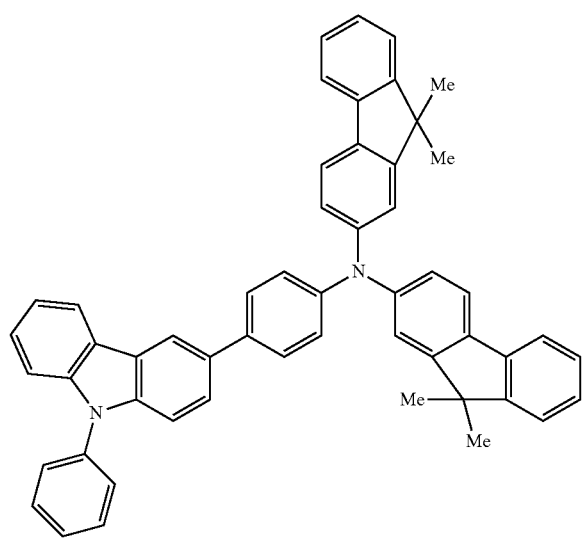
2-12
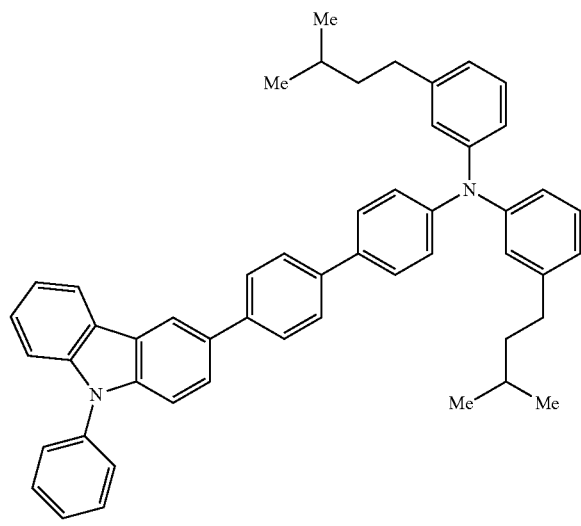
2-13
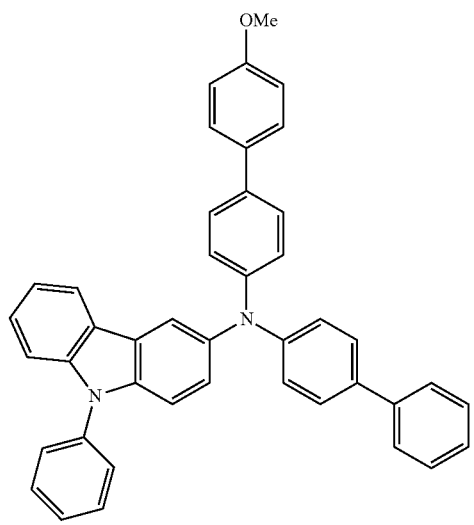
2-14
2-15
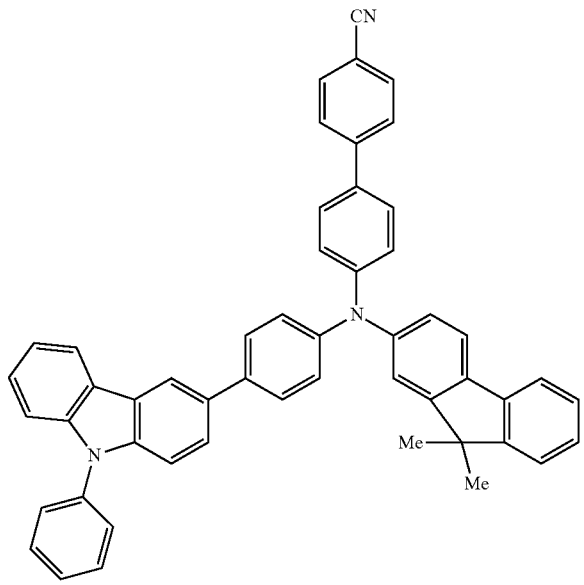

2-16

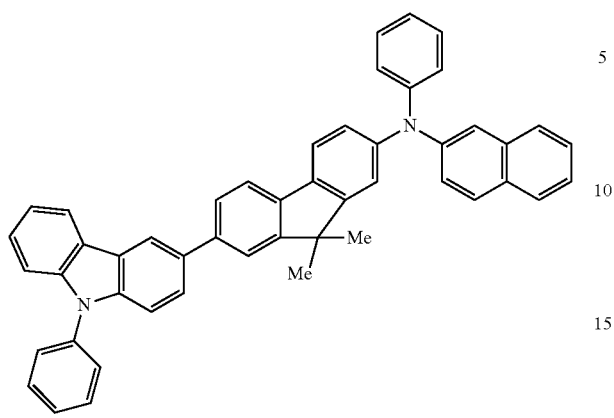

2-17

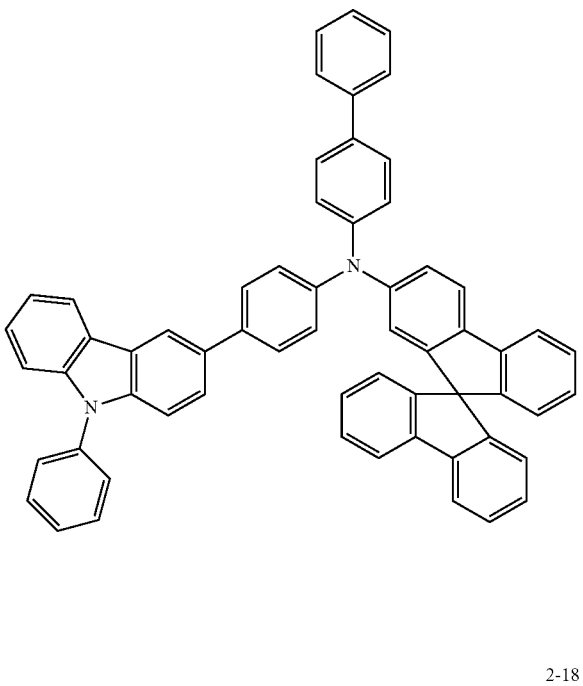

2-18

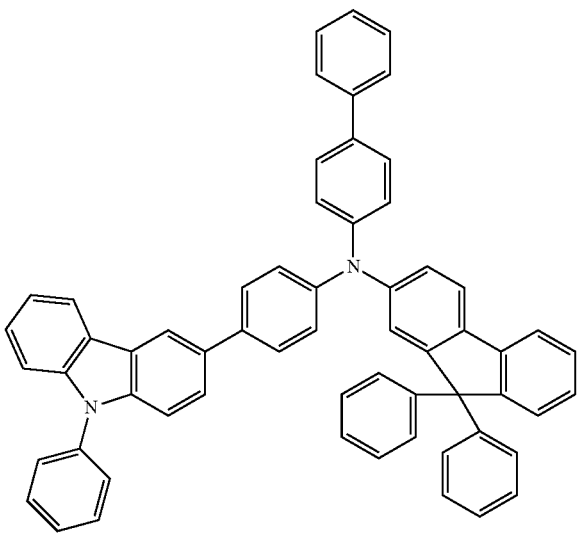

2-19

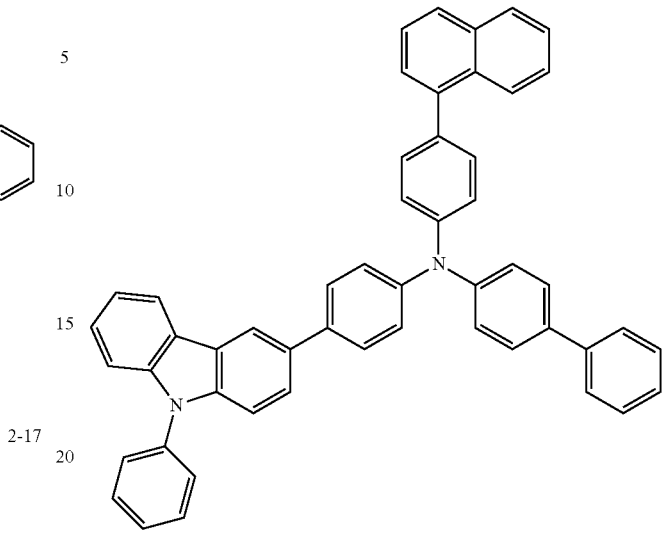

2-20

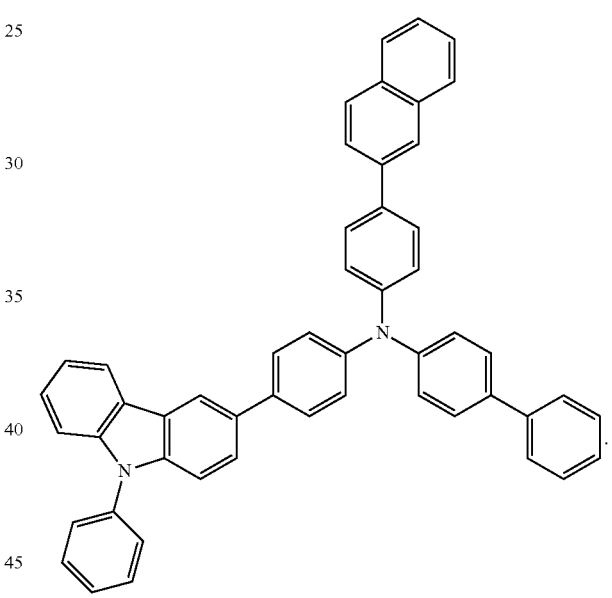

The second hole transport layer may include the third hole transport material represented by Formula 3, and $Ar_6$ and $Ar_7$ in Formula 3 may include a substituted or unsubstituted phenyl group, a substituted or unsubstituted biphenyl group, a substituted or unsubstituted naphthyl group, a substituted or unsubstituted dibenzofuran group, or a substituted or unsubstituted dibenzothiophene group.

The second hole transport layer may include the third hole transport material represented by Formula 3, and $R_5$ in Formula 3 may include a substituted or unsubstituted phenyl group, a substituted or unsubstituted biphenyl group, a substituted or unsubstituted naphthyl group, a substituted or unsubstituted fluorenyl group, a substituted or unsubstituted dibenzofuran group, or a substituted or unsubstituted benzo[def]carbazole group.

The second hole transport layer may include the third hole transport material represented by Formula 3, and the third hole transport material may include one of the following Compounds 3-1 to 3-20:

3-1
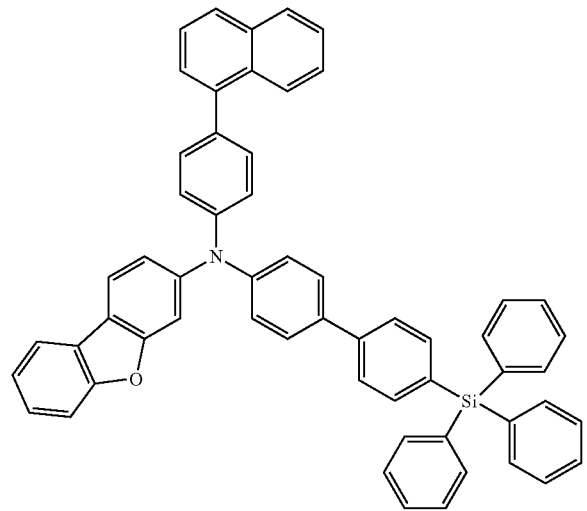
3-2
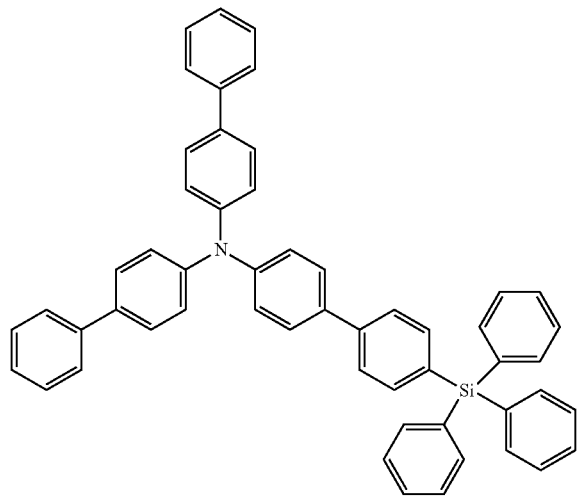
3-3
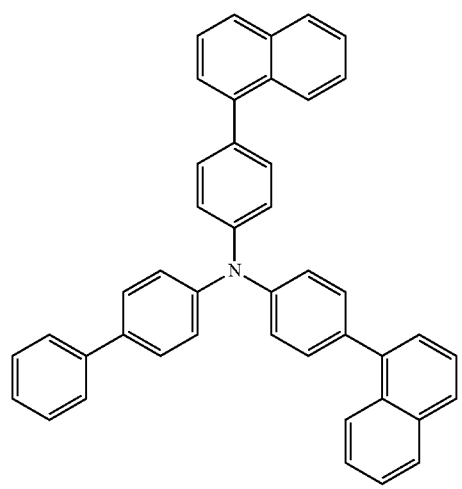
3-4
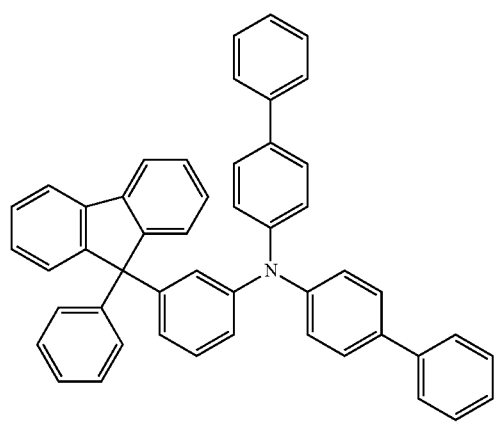
3-5
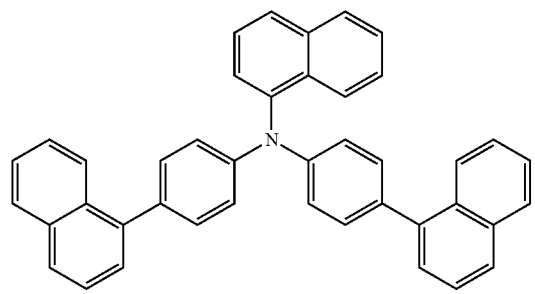
3-6
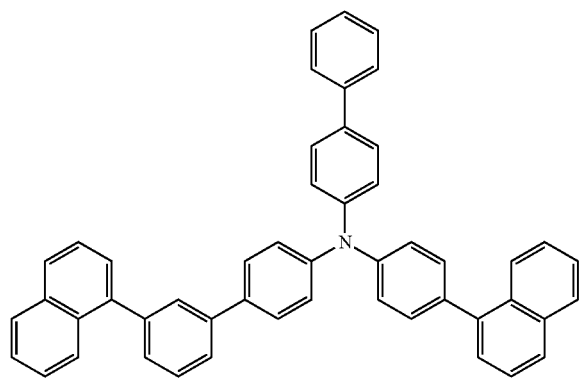

-continued
3-7
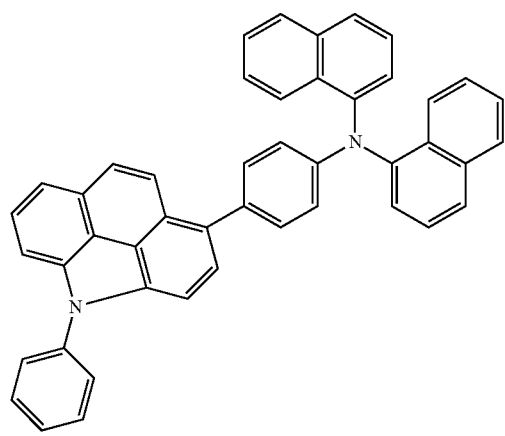
3-8
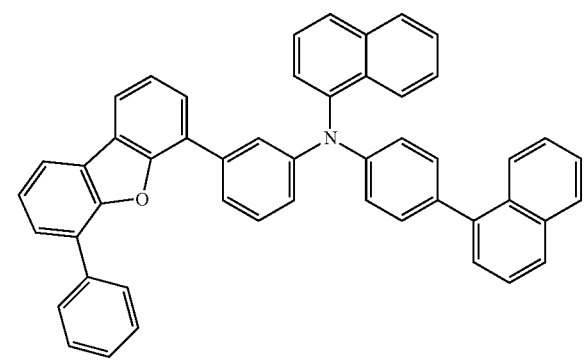
3-9
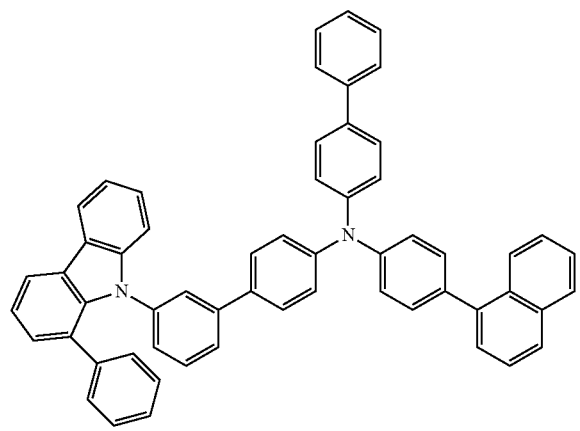
3-10
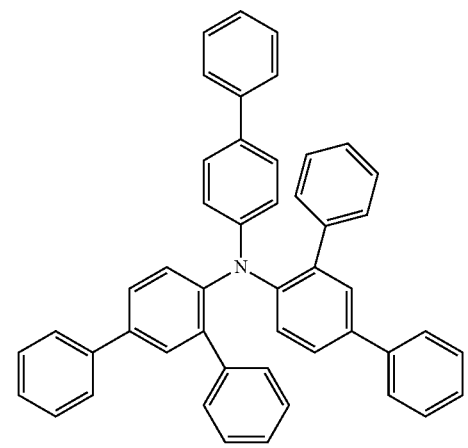
3-11
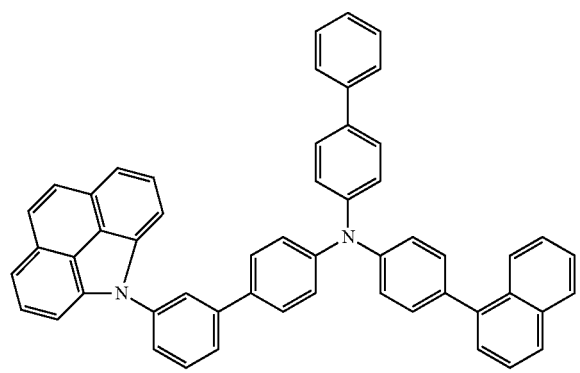
3-12
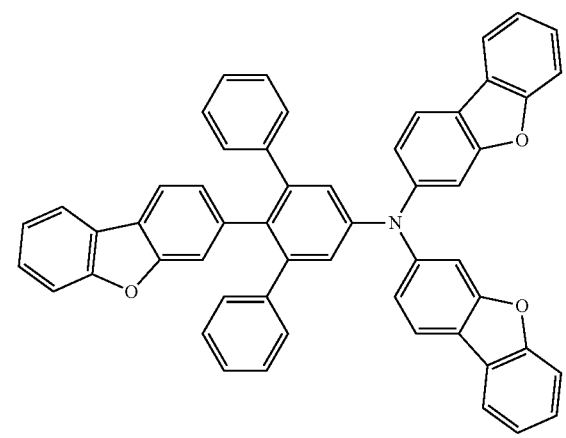

-continued
3-13
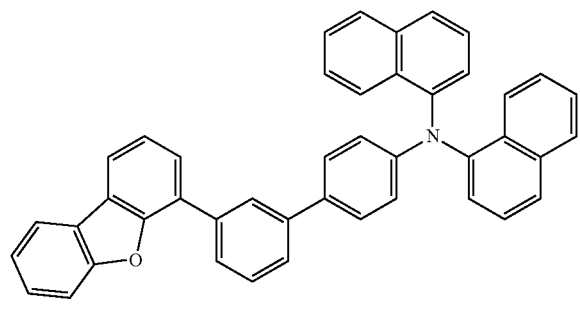
3-14
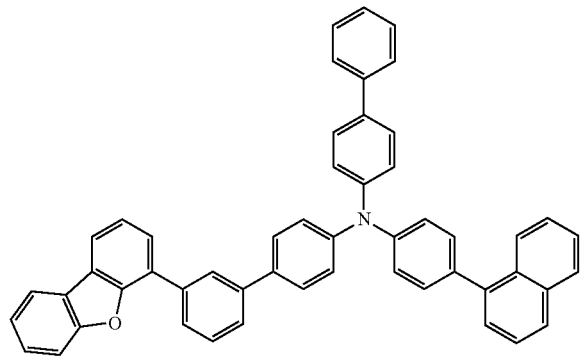
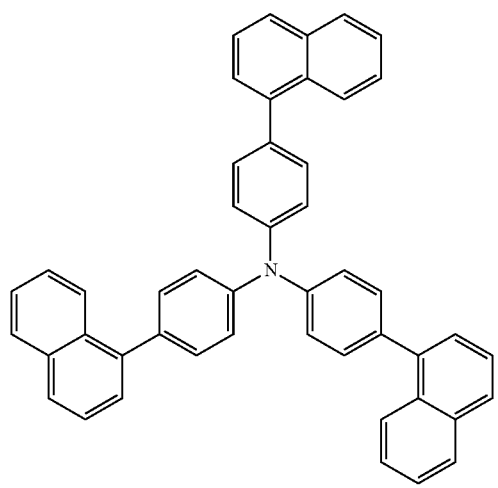
3-15
3-16
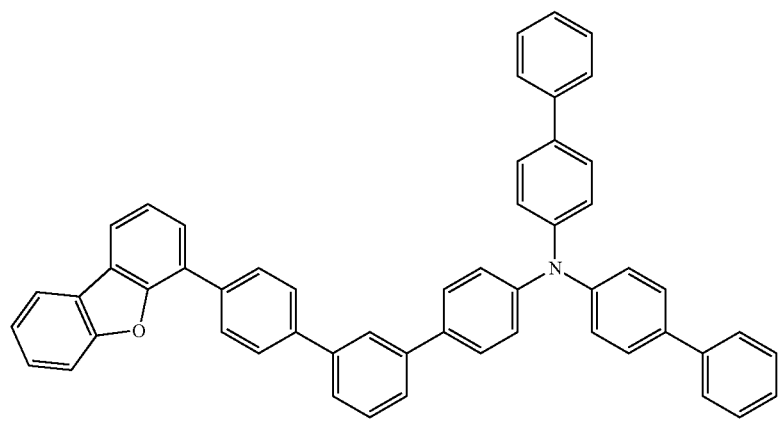

3-17

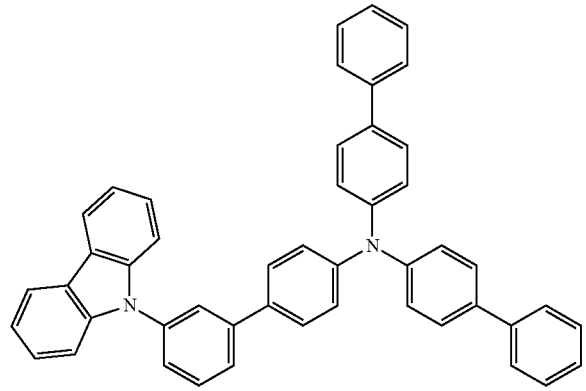

3-18

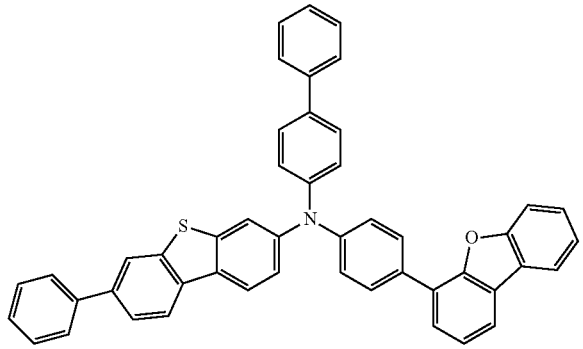

3-19

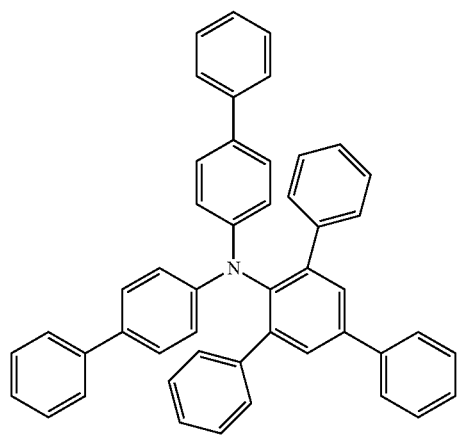

3-20

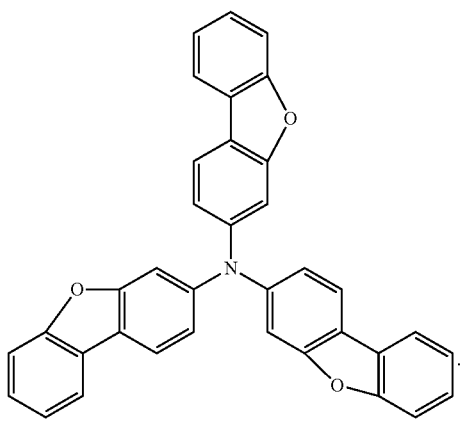

The second hole transport layer may include the fourth hole transport material represented by Formula 4, and $Ar_8$ in Formula 4 may combine with at least one of $R_6$ or $R_{13}$ to form a ring.

The second hole transport layer may include the fourth hole transport material represented by Formula 4, and $R_9$ and $R_{10}$ in Formula 4 may combine to form a ring that includes X.

The second hole transport layer may include the fourth hole transport material represented by Formula 4, and $Ar_8$ in Formula 4 may include a substituted or unsubstituted phenyl group, a substituted or unsubstituted biphenyl group, or a substituted or unsubstituted carbazole group.

The second hole transport layer may include the fourth hole transport material represented by Formula 4, and $R_6$, $R_7$, $R_8$, $R_9$, $R_{10}$, $R_{11}$, $R_{12}$, $R_{13}$, $R_{14}$ and $R_{15}$ in Formula 4 may include a substituted or unsubstituted phenyl group, a substituted or unsubstituted naphthyl group, substituted or unsubstituted carbazole group, a substituted or unsubstituted benzo[def]carbazole group, a substituted or unsubstituted fluorenyl group, a substituted or unsubstituted dibenzofuran group, a substituted or unsubstituted triphenylene group, a substituted or unsubstituted phenanthrene group, or a substituted or unsubstituted dibenzosilole group.

The second hole transport layer may include the fourth hole transport material represented by Formula 4, and the fourth hole transport material may include one of the following Compounds 4-1 to 4-20:

25 26
4-1
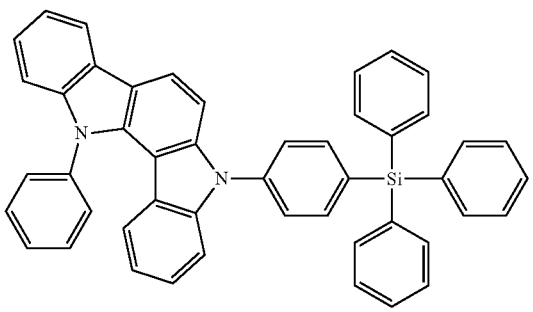
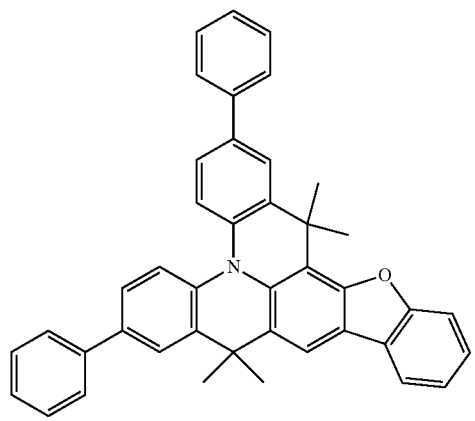
4-2
4-3
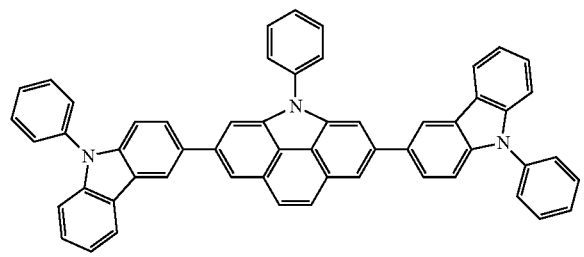
4-4
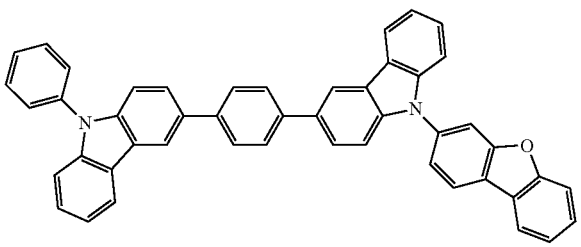
4-5
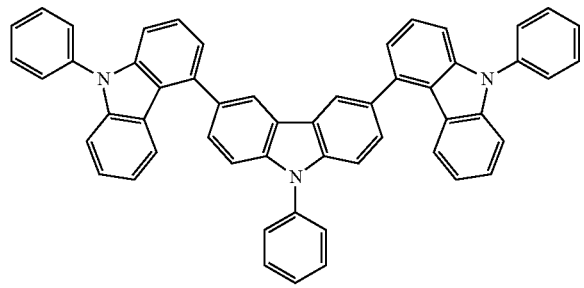
4-6
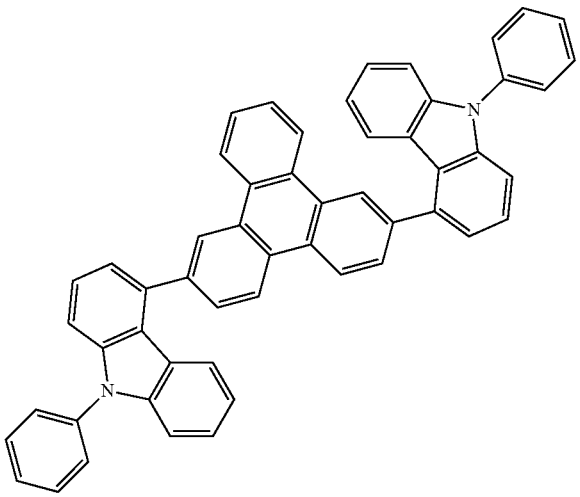
4-7
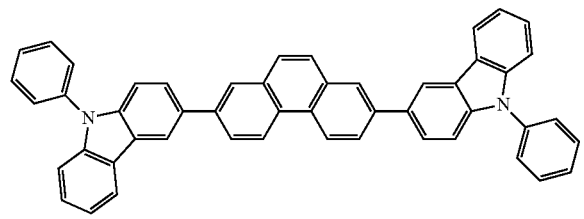
4-8
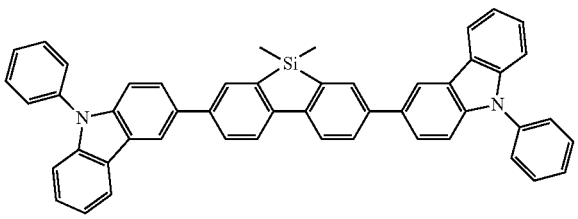

-continued
4-9
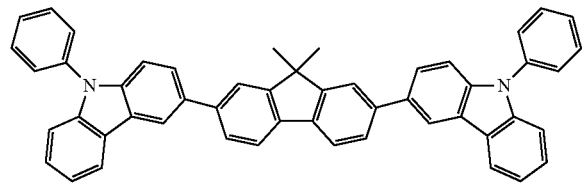
4-10
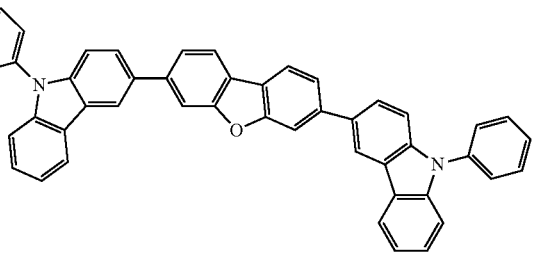
4-11
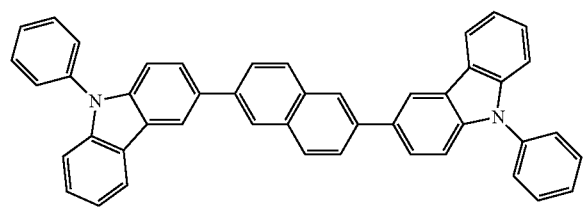
4-12
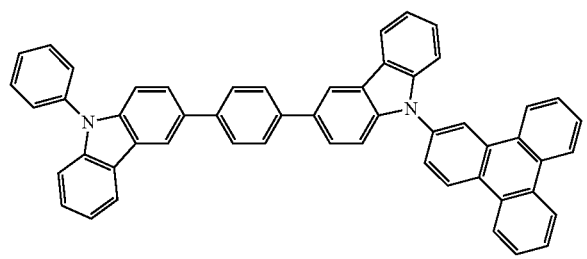
4-13
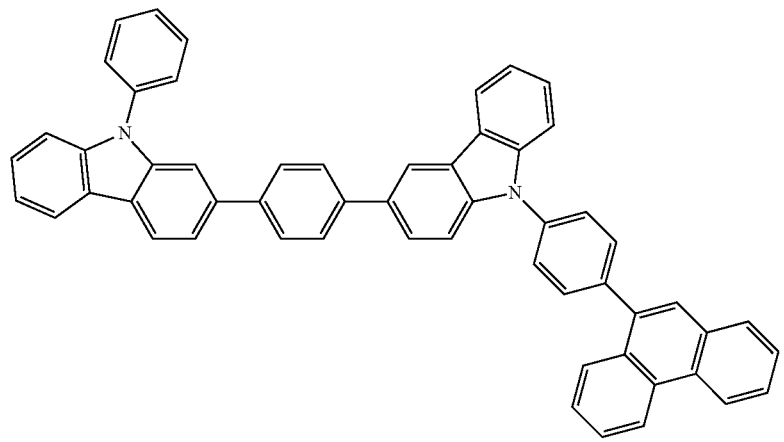
4-14
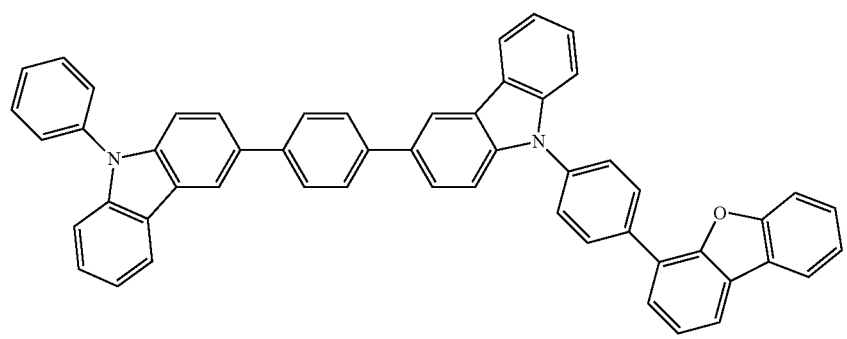

-continued
4-15
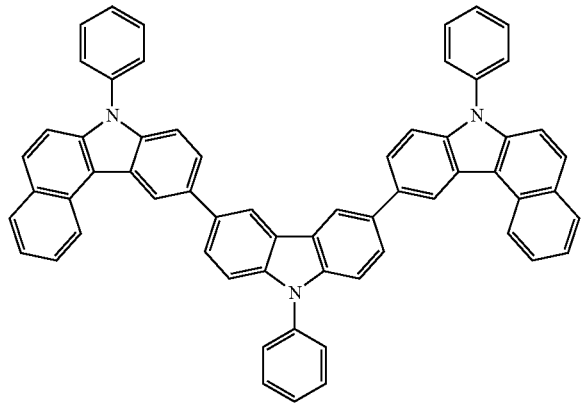
4-16
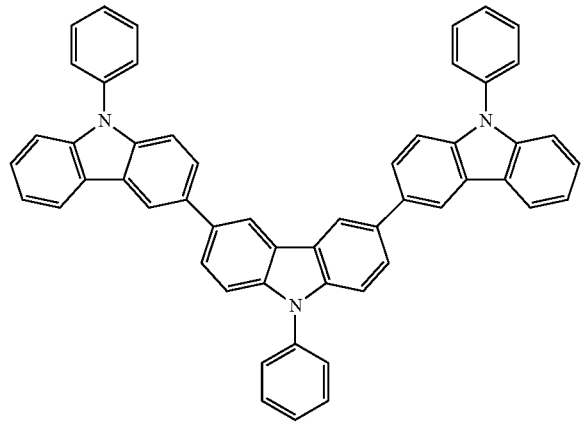
4-17
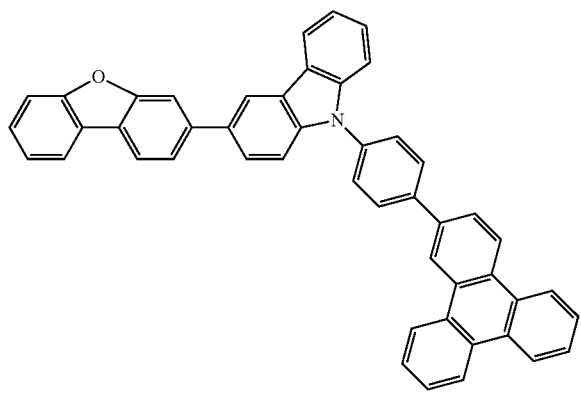
4-18
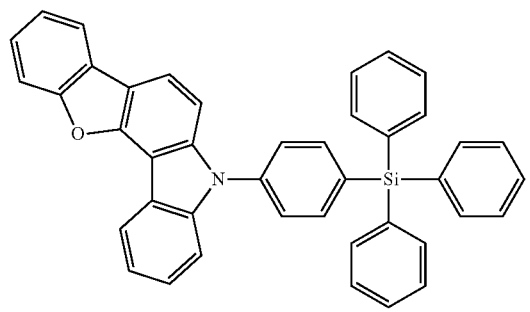
4-19
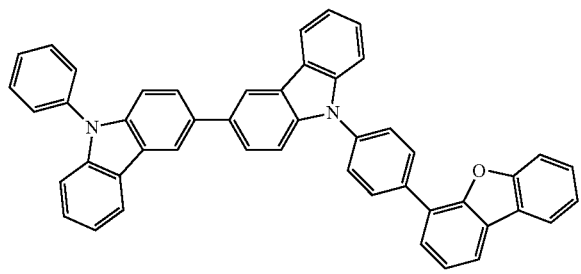
4-20
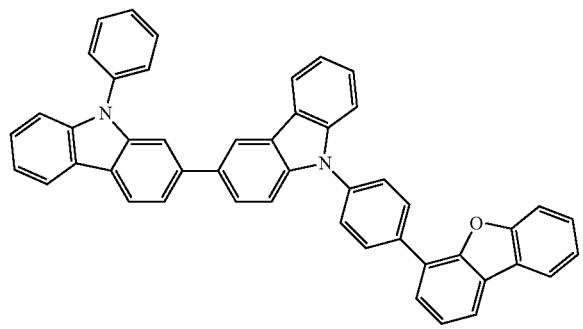
4-21
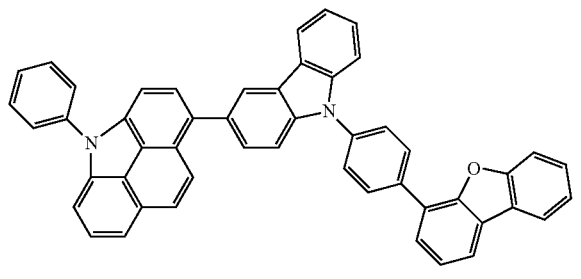
4-22
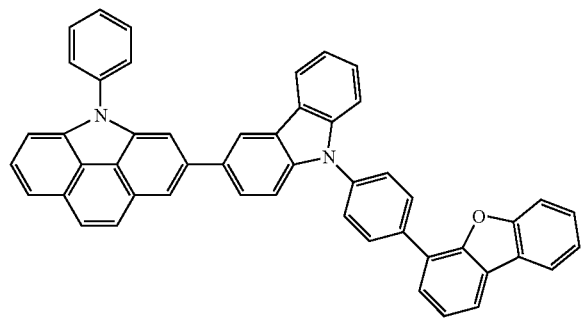

-continued 4-23
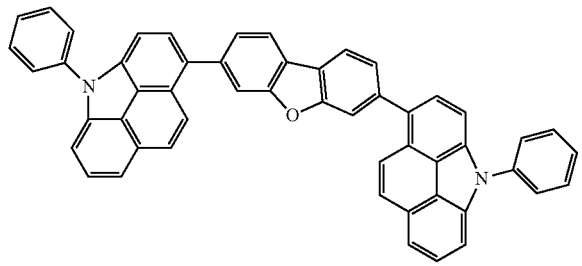

4-24
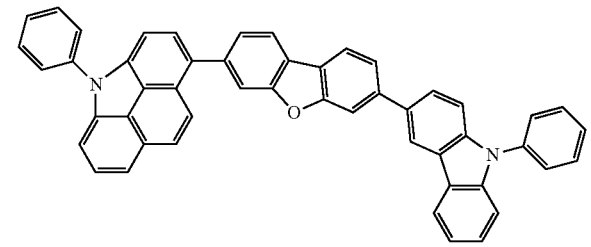

4-25
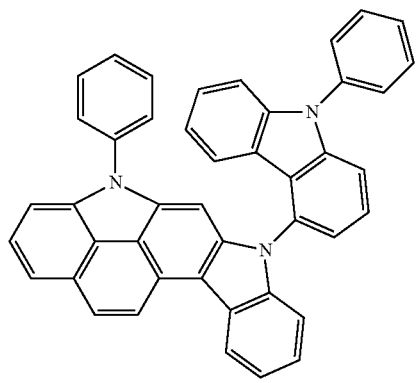

4-26
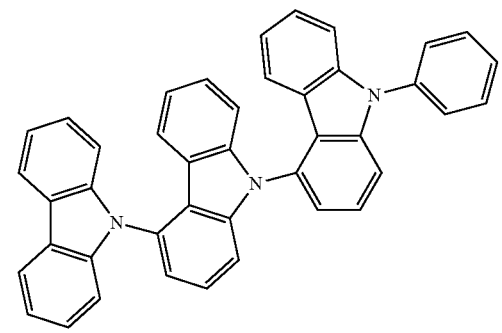

4-27
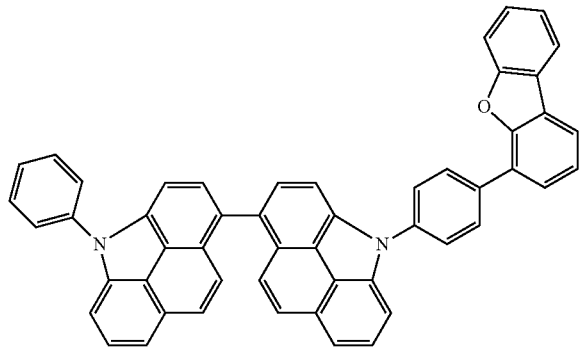

4-28
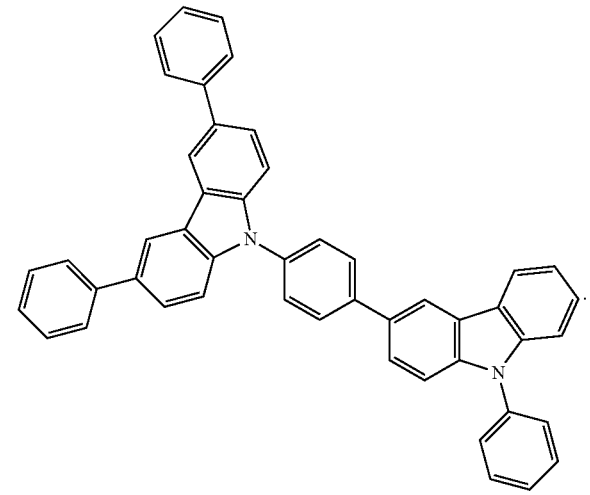

The hole transport region may further include a hole injection layer between the anode and the first hole transport layer.

The electron transport region may include an electron transport layer; and an electron injection layer on the electron transport layer.

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
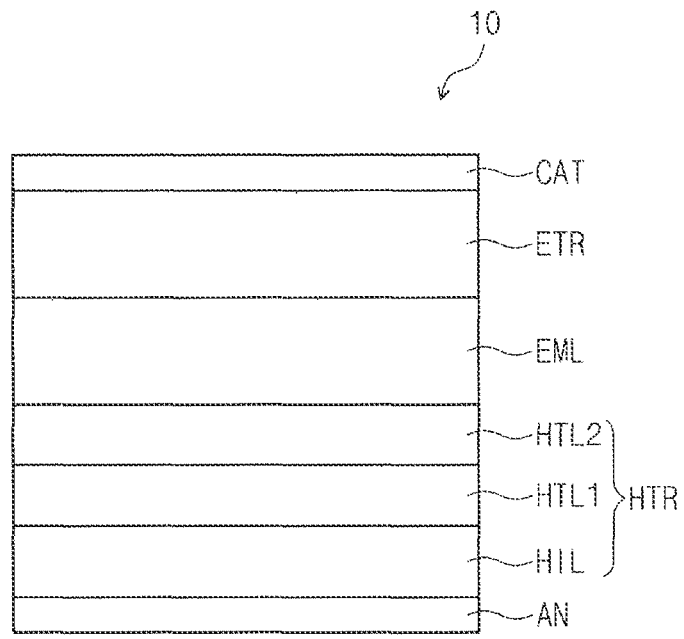
FIG. 1 illustrates a schematic cross-sectional view of an organic light emitting device according to an embodiment of the present disclosure.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

Like reference numerals refer to like elements for explaining each drawing. In the drawings, the sizes of elements may be enlarged for clarity of the present disclosure. It will be understood that, although the terms first, second, etc. may be used herein to describe various elements, these elements should not be limited by these terms. These terms are only used to distinguish one element from another element. For example, a first element discussed below could be termed a second element, and similarly, a second element could be termed a first element. As used herein, the singular forms are intended to include the plural forms as well, unless the context clearly indicates otherwise.

It will be further understood that the terms "comprises," "includes," "including," or "comprising," when used in this specification, specify the presence of stated features, numerals, steps, operations, elements, parts, or a combination thereof, but do not preclude the presence or addition of one or more other features, numerals, steps, operations, elements, parts, or a combination thereof. It will also be understood that when a layer, a film, a region, a plate, etc. is referred to as being cony another part, it can be directly on the other part, or intervening layers may also be present. On the contrary, when a layer, a film, a region, a plate, etc. is referred to as being 'under' another part, it can be directly under the other part, or intervening layers may also be present. In addition, the term "or" is not an exclusive term such that "A or B" would include all combinations thereof, i.e., A, B, or A and B.

In the present disclosure, "substituted or unsubstituted" may mean substituted with at least one substituent selected from deuterium, halogen, nitrile, nitro, amino, silyl, boron, phosphine oxide, alkyl, alkoxy, alkenyl, fluorenyl, aryl, and heterocycle or unsubstituted. In addition, each of the substituent illustrated above may be substituted or unsubstituted. For example, biphenyl may be interpreted as aryl, or phenyl substituted or unsubstituted with phenyl.

In the present disclosure, the description of forming a ring by combining or bonding adjacent groups with each other may mean forming a substituted or unsubstituted hydrocarbon ring or a substituted or unsubstituted heterocycle by the combination of adjacent groups with each other. The hydrocarbon ring may include an aliphatic hydrocarbon ring and an aromatic hydrocarbon ring. The heterocycle may include an aliphatic heterocycle and aromatic heterocycle. The hydrocarbon ring and heterocycle may be a monocycle or polycycle. In addition, the ring formed by combining adjacent groups may be connected with another ring to form a spiro structure.

In the present disclosure, the terms "an adjacent group" may mean a substituent at an atom which is directly connected with another atom at which a corresponding substituent is substituted, another substituent at an atom at which a corresponding substituent is substituted, or a substituent stereoscopically disposed at the nearest position to a corresponding substituent. For example, two methyl groups in 1,2-dimethylbenzene may be interpreted as "adjacent groups", and two ethyl groups in 1,1-diethylcyclopentene may be interpreted as "adjacent groups".

In the present disclosure, a halogen atom may include a fluorine atom, a chlorine atom, a bromine atom, or an iodine atom.

In the present disclosure, the alkyl group may have a linear, branched, or cyclic shape. The carbon number of the alkyl group may be 1 to 30, 1 to 20, 1 to 10, or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyl eicosyl, 2-butyl eicosyl, 2-hexyl eicosyl, 2-octyl eicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the present disclosure, the aryl group may mean an optional functional group or substituent derived from an aromatic hydrocarbon ring. The aryl group may be monocyclic aryl or polycyclic aryl. The carbon number of the aryl group for forming a ring may be 6 to 30, or 6 to 20. Examples of the aryl may include phenyl, naphthyl, fluorenyl, anthracenyl, phenanthryl, biphenyl, terphenyl, quaterphenyl, quinqphenyl, sexiphenyl, triphenylene, pyrenyl, benzofluoranthenyl, chrysenyl, etc., without limitation.

In the present disclosure, the fluorenyl group may be substituted, or two substituents may be combined with each other to form a spiro structure.

In the present disclosure, the heteroaryl group may be heteroaryl including at least one of O, N or S as a heteroatom. The carbon number of the heteroaryl group for forming a ring may be 2 to 30, or 2 to 20. Examples of the heteroaryl group may include thiophene, furan, pyrrole, imidazole, thiazole, oxazole, oxadiazole, triazole, pyridyl, bipyridyl, pyrimidyl, triazine, triazole, acridyl, pyridazine, pyrazinyl, quinolinyl, quinazoline, quinoxalinyl, phenoxazyl, phthalazinyl, pyrido pyrimidinyl, pyrido pyrazinyl, pyrazino pyrazinyl, isoquinoline, indole, carbazole, N-arylcarbazole, N-heteroaryl carbazole, N-alkyl carbazole, benzoxazole, benzoimidazole, benzothiazole, benzocarbazole, benzothiophene, dibenzothiophene, thienothiophene, benzofuranyl, phenanthroline, thiazolyl, isooxazolyl, oxadiazolyl, thiadiazolyl, benzothiazolyl, phenothiazinyl, dibenzofuranyl, etc., without limitation.

In the present disclosure, the explanation on the aryl group may be applied to the arylene group, except that the arylene group is a divalent group.

In the present disclosure, the silyl group may include alkyl silyl group and aryl silyl group. Examples of the silyl group may include trimethylsilyl, triethylsilyl, t-butyl dimethylsilyl, vinyl dimethylsilyl, propyl dimethylsilyl, triphenylsilyl, diphenylsilyl, phenylsilyl, etc., without limitation.

In the present disclosure, the boron group may include alkyl boron group and aryl boron group. Examples of the boron group may include trimethyl boron, triethyl boron, t-butyl dimethyl boron, triphenyl boron, diphenyl boron, phenyl boron, etc., without limitation.

In the present disclosure, the alkenyl group may be linear or branched. The carbon number is not specifically limited, however may be 2 to 30, 2 to 20, or 2 to 10. Examples of the alkenyl group may include vinyl, 1-butenyl, 1-pentenyl, 1,3-butadienyl aryl, styrenyl, stilbenyl, etc., without limitation.

Hereinafter, the organic light emitting device according to an embodiment of the present disclosure will be explained.

Figure 2:
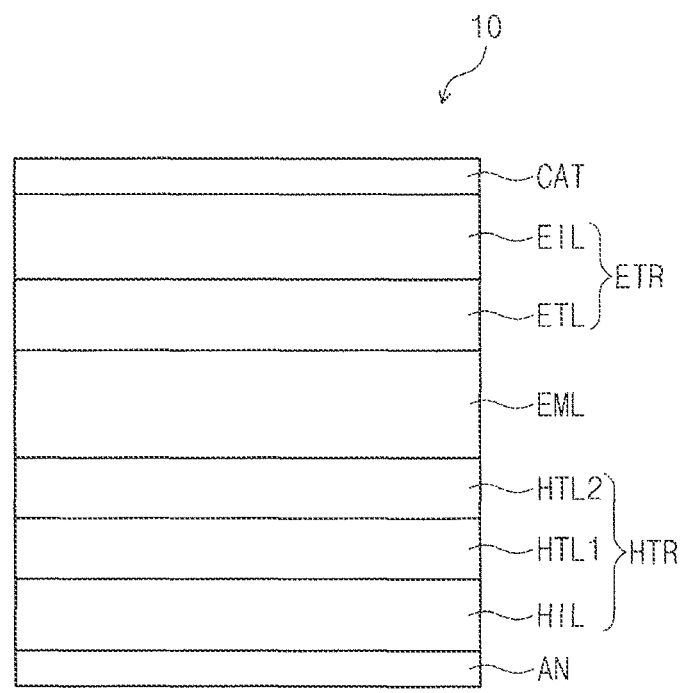
FIG. 2 illustrates a schematic cross-sectional view of an organic light emitting device according to an embodiment of the present disclosure.

FIG. 1 illustrates a schematic cross-sectional view of an organic light emitting device according to an embodiment of the present disclosure. FIG. 2 illustrates a schematic cross-sectional view of an organic light emitting device according to an embodiment of the present disclosure.

Referring to FIGS. 1 and 2, an organic light emitting device 10 according to an embodiment of the present disclosure may include an anode AN, a hole transport region HTR, an emission layer EML, an electron transport region ETR, and a cathode CAT.

The anode AN has conductivity. The anode AN may be a pixel electrode or a positive electrode. The anode AN may be a transmissive electrode, a transflective electrode, or a reflective electrode. In the case where the anode AN is the transmissive electrode, the anode AN may be formed using a transparent metal oxide such as indium tin oxide (ITO), indium zinc oxide (IZO), zinc oxide (ZnO), or indium tin zinc oxide (ITZO). In the case where the anode AN is the transflective electrode or reflective electrode, the anode AN may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). In an implementation, the anode AN may include a plurality of layers including a reflective layer or transflective layer formed using the above materials, and a transparent layer formed using ITO, IZO, ZnO, or ITZO.

The hole transport region HTR may be provided on the anode AN. The hole transport region HTR may include, e.g., a first hole transport layer HTL1 and a second hole transport layer HTL2 (e.g., different from the first hole transport layer). In an implementation, the hole transport region HTR may further include at least one of a hole injection layer HIL, a hole buffer layer and an electron blocking layer. In an implementation, the thickness of the hole transport region HTR may be, e.g., from about 1,000 Å to about 1,500 Å. In an implementation, the thickness of the hole transport region HTR may be from about 100 Å to about 10,000 Å, e.g., from about 100 Å to about 1,000 Å.

The hole transport region HTR may be formed using various methods, e.g., a vacuum deposition method, a spin coating method, a cast method, a Langmuir-Blodgett (LB) method, an inkjet printing method, a laser printing method, or a laser induced thermal imaging (LITI) method.

The hole injection layer HIL may include, e.g., a phthalocyanine compound such as copper phthalocyanine; N,N'-diphenyl-N,N'-bis-[4-(phenyl-m-tolyl-amino)-phenyl]-biphenyl-4,4'-diamine (DNTPD), 4,4',4''-tris(3-methylphenylphenylamino)triphenylamine (m-MTDATA), 4,4',4''-tris(N,N-diphenylamino)triphenylamine (TDATA), 4,4',4''-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrene-sulfonate) (PANI/PSS), N,N'-dinaphthalene-1-yl)-N,N'-diphenyl-benzidine (NPB), triphenylamine-containing polyether ketone (TPAPEK), 4-isopropyl-4'-methyldiphenyliodonium tetrakis(pentafluorophenyl)borate, or the like.

In an implementation, the first hole transport layer HTL1 may include, e.g., a first hole transport material represented by the following Formula 1 or a second hole transport material represented by the following Formula 2. The second hole transport layer HTL2 may be provided on the first hole transport layer HTL1. In an implementation, the second hole transport layer HTL2 may include, e.g., a third hole transport material represented by the following Formula 3 or a fourth hole transport material represented by the following Formula 4.

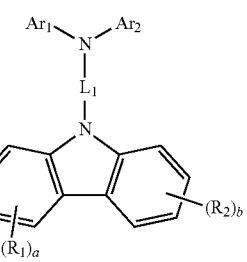

[Formula 1]

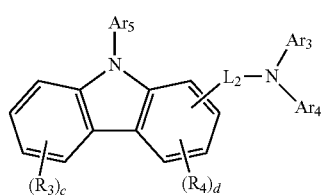

[Formula 2]

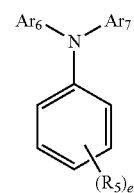

[Formula 3]

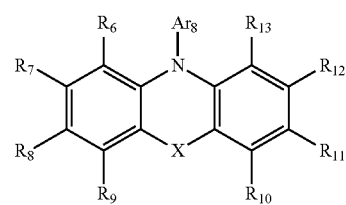

[Formula 4]

$Ar_1$, $Ar_2$, $Ar_3$, $Ar_4$, $Ar_5$, $Ar_6$, $Ar_7$, and $Ar_8$ may each independently be selected from or include, e.g., a substituted or unsubstituted aryl group having 6 to 30 ring carbon atoms, a substituted or unsubstituted heteroaryl group having 5 to 30 ring carbon atoms, a substituted or unsubstituted alkyl group having 1 to 20 carbon atoms, a substituted or unsubstituted silyl group, a halogen atom, a deuterium atom, or a hydrogen atom.

X may be, e.g., a direct linkage or $CR_{14}R_{15}$.

$R_1$, $R_2$, $R_3$, $R_4$, $R_5$, $R_6$, $R_7$, Ra, $R_9$, $R_{10}$, $R_{11}$, $R_{12}$, $R_{13}$, $R_{14}$ and $R_{15}$ may each independently be selected from or include, e.g., a substituted or unsubstituted aryl group having 6 to 30 ring carbon atoms, a substituted or unsubstituted heteroaryl group having 5 to 30 ring carbon atoms, a substituted or unsubstituted alkyl group having 1 to 20 carbon atoms, a substituted or unsubstituted silyl group, a halogen atom, a deuterium atom, or a hydrogen atom.

L$_1$ and L$_2$ may each independently be selected from or include, e.g., a direct linkage (e.g., single bond), a substituted or unsubstituted alkyl group having 6 to 30 carbon atoms, a substituted or unsubstituted arylene group having 6 to 30 ring carbon atoms, or a substituted or unsubstituted heteroarylene group having 5 to 30 ring carbon atoms.

a, b, and c may each independently be, e.g., an integer of 0 to 4, d may be, eg., an integer of 0 to 3, and e may be, e.g., an integer of 0 to 5, in the case where e is 2 or more (e.g., an integer of 2 to 5), adjacent groups or ones of R$_1$, R$_2$, R$_3$, R$_4$, R$_5$, R$_6$, R$_7$, Ra, R$_9$, R$_{10}$, R$_{11}$, R$_{12}$, R$_{13}$, R$_{14}$ and R$_{15}$ may be separate or may be bound to form a ring from each other.

In Formula 1, Ar$_1$ and Ar$_2$ may each independently be selected from or include, e.g., a substituted or unsubstituted aryl group having 6 to 30 ring carbon atoms, a substituted or unsubstituted heteroaryl group having 5 to 30 ring carbon atoms, a substituted or unsubstituted alkyl group having 1 to 20 carbon atoms, a substituted or unsubstituted silyl group, a halogen atom, a deuterium atom, or a hydrogen atom.

In an implementation, Ar$_1$ and Ar$_2$ may each independently be selected from or include, e.g., a substituted or unsubstituted phenyl group, a substituted or unsubstituted biphenyl group, a substituted or unsubstituted naphthyl group, a substituted or unsubstituted fluorenyl group, or a substituted or unsubstituted acridine group.

In an implementation, Ar$_1$ and Ar$_2$ may each independently be selected from or include, e.g., an unsubstituted or alkyl substituted fluorenyl group, an unsubstituted or alkyl substituted acridine group, an unsubstituted or alkyl substituted phenyl group, an unsubstituted or alkoxy substituted phenyl group, an unsubstituted or halogen substituted phenyl group, an unsubstituted or nitrile substituted phenyl group, or an unsubstituted or aryl substituted phenyl group.

In an implementation, Ar$_1$ and Ar$_2$ may each independently be selected from or include, e.g., an unsubstituted or phenyl substituted phenyl group or an unsubstituted or naphthyl substituted phenyl group.

In an implementation, L$_1$ in Formula 1 may be selected from or include, e.g., a direct linkage, a substituted or unsubstituted alkyl group having 6 to 30 carbon atoms, a substituted or unsubstituted arylene group having 6 to 30 ring carbon atoms, or a substituted or unsubstituted heteroarylene group having 5 to 30 ring carbon atoms.

In an implementation, L$_1$ in Formula 1 may be selected from or include, e.g., a substituted or unsubstituted phenylene group, a substituted or unsubstituted divalent biphenyl, or a substituted or unsubstituted fluorenylene group.

In an implementation, in Formula 1, R$_1$ and R$_2$ may each independently be selected from or include, e.g., a substituted or unsubstituted aryl group having 6 to 30 ring carbon atoms, a substituted or unsubstituted heteroaryl group having 5 to 30 ring carbon atoms, a substituted or unsubstituted alkyl group having 1 to 20 carbon atoms, a substituted or unsubstituted silyl group, a halogen atom, a deuterium atom, or a hydrogen atom.

In Formula 1, a and b may each independently be, e.g., an integer of 0 to 4.

In the case where a is an integer of 1 or more (e.g., 1 to 4), a plurality of R$_1$ may be the same or different, or at least one R$_1$ may be different. In the case where b is an integer of 1 or more (e.g., 1 to 4), a plurality of R$_2$ may be the same or different, or at least one R$_2$ may be different.

In an implementation, the first hole transport material may include, e.g., one of the following Compounds.

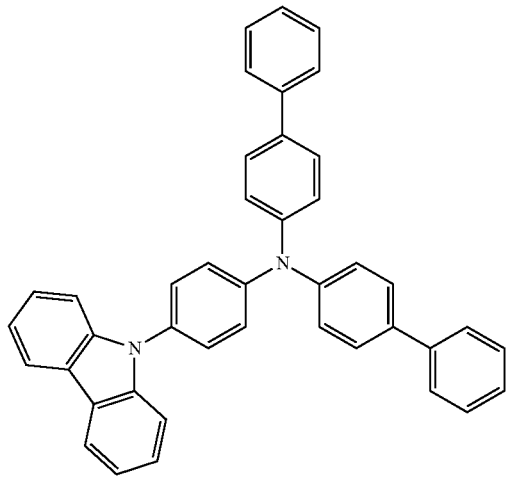

1-1

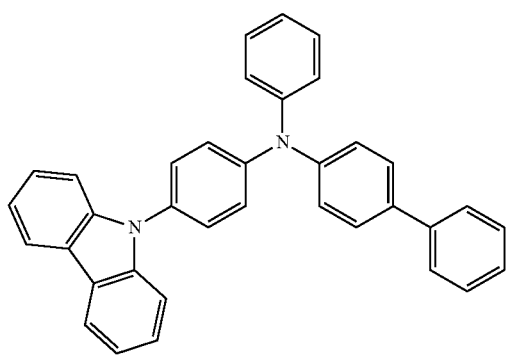

1-2

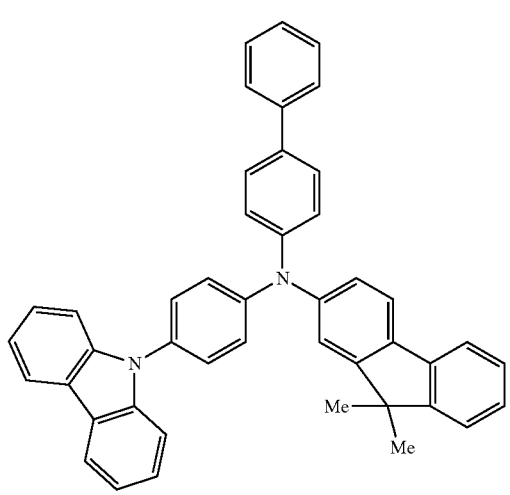

1-3

1-4
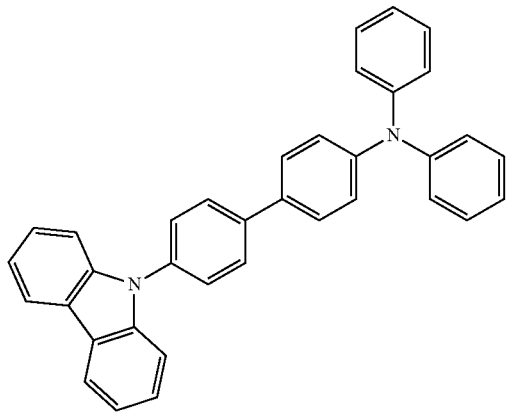
1-7
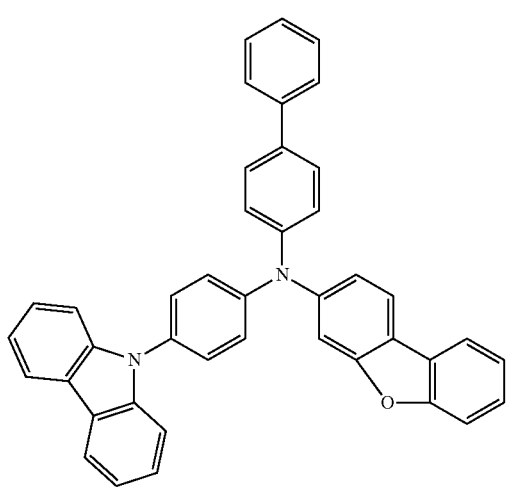
1-8
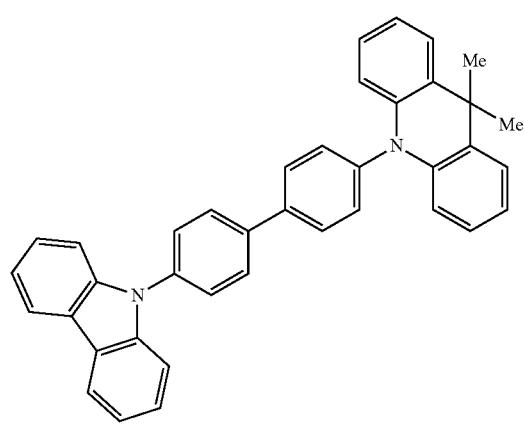
1-9
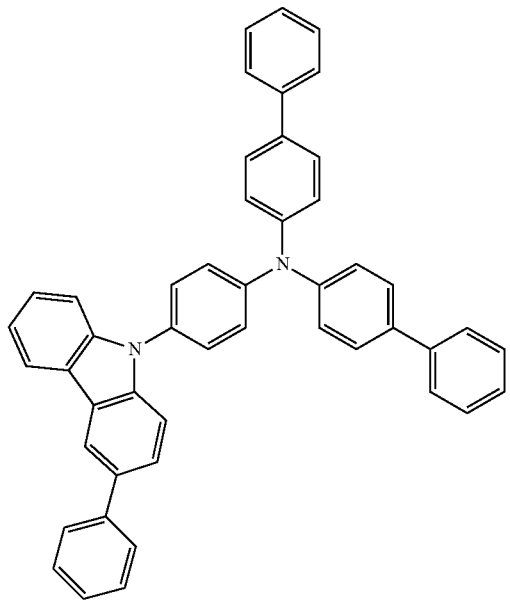
1-10
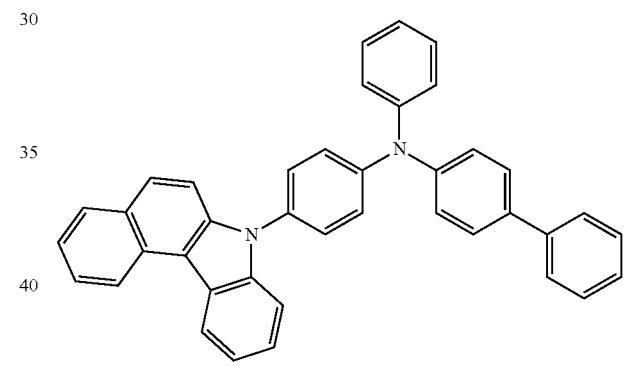
1-11
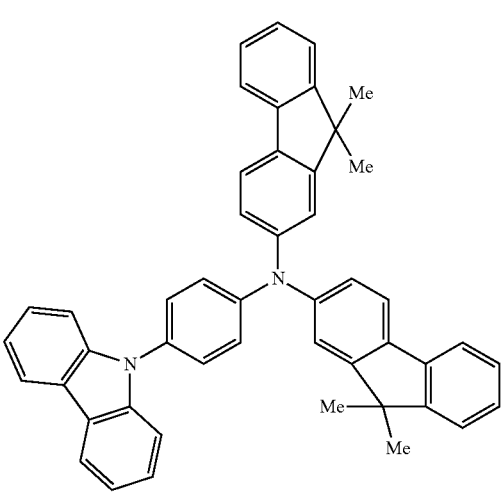

1-12
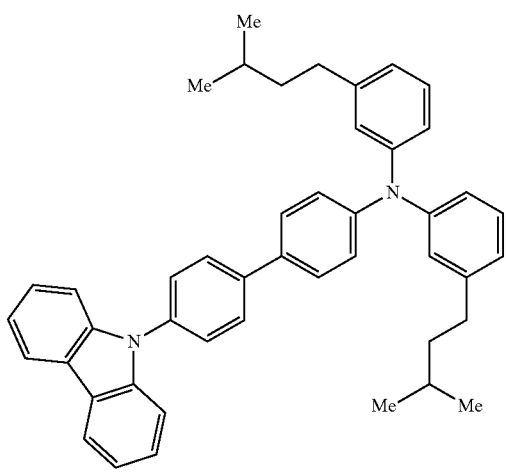
1-13
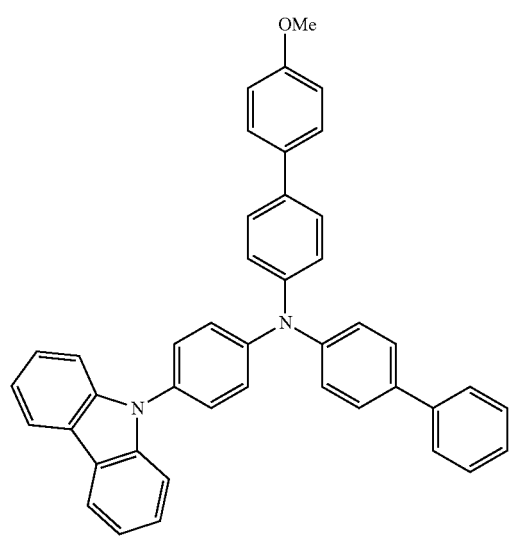
1-14
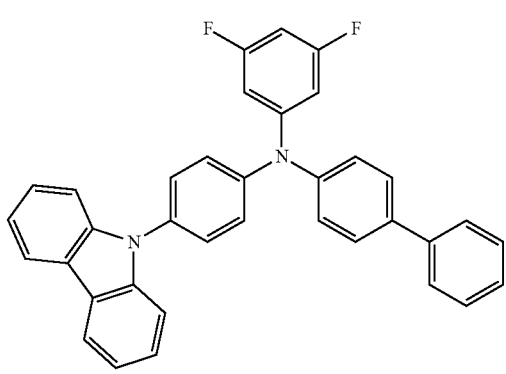
1-15
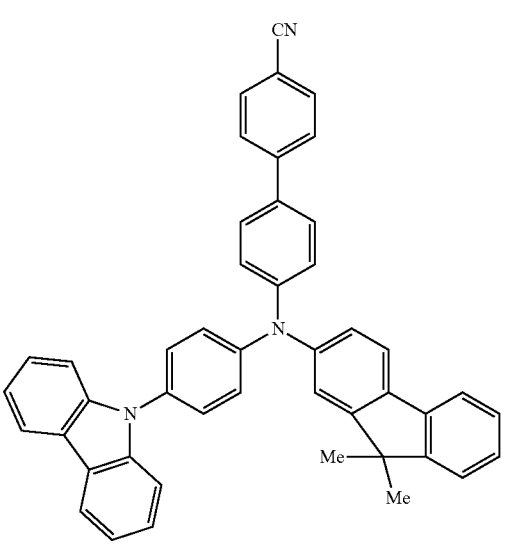
1-16
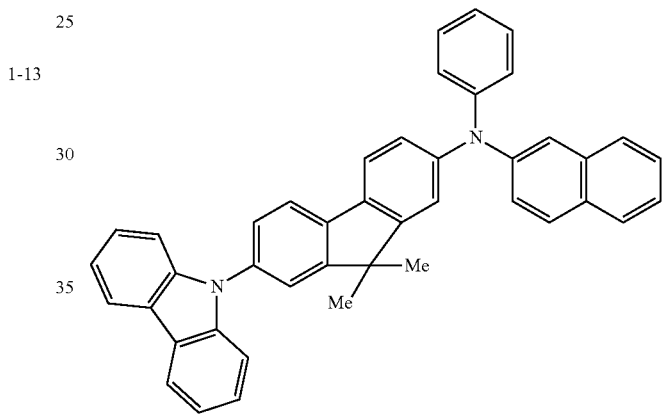
1-17
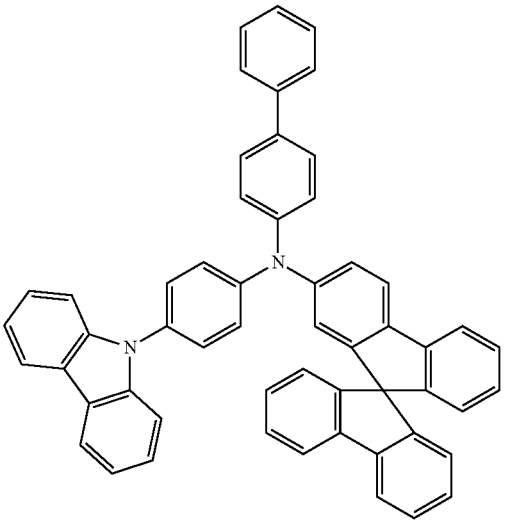

-continued

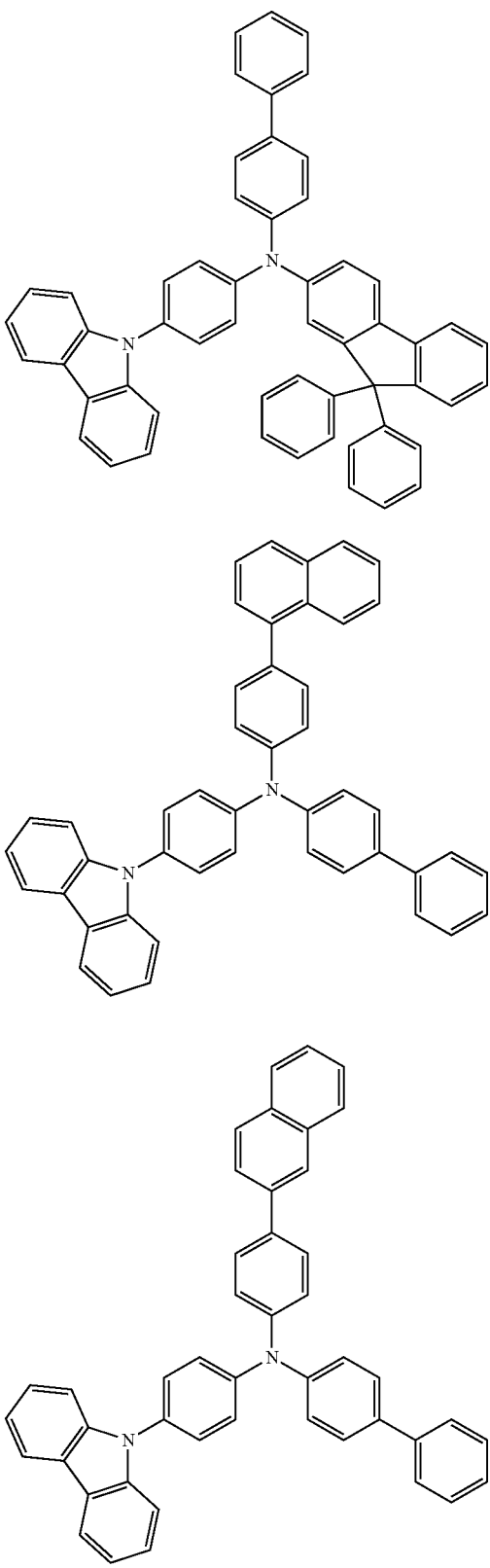

1-18

1-19

1-20

In an implementation, in Formula 2, $Ar_3$ and $Ar_4$ may each independently be selected from or include, e.g., a substituted or unsubstituted aryl group having 6 to 30 ring carbon atoms, a substituted or unsubstituted heteroaryl group having 5 to 30 ring carbon atoms, a substituted or unsubstituted alkyl group having 1 to 20 carbon atoms, a substituted or unsubstituted silyl group, a halogen atom, a deuterium atom, or a hydrogen atom.

In an implementation, in Formula 2, $Ar_3$ and $Ar_4$ may each independently be selected from or include, e.g., a substituted or unsubstituted phenyl group, a substituted or unsubstituted biphenyl group, a substituted or unsubstituted naphthyl group, a substituted or unsubstituted fluorenyl group, or a substituted or unsubstituted spirobifluorenyl group.

In an implementation, in Formula 2, $Ar_3$ and $Ar_4$ may each independently be selected from or include, e.g., an unsubstituted or alkyl substituted fluorenyl group, an unsubstituted or alkyl substituted acridine group, an unsubstituted or alkyl substituted phenyl group, an unsubstituted or alkoxy substituted phenyl group, an unsubstituted or halogen substituted phenyl group, an unsubstituted or nitrile substituted phenyl group, or an unsubstituted or aryl substituted phenyl group.

In an implementation, in Formula 2, $Ar_3$ and $Ar_4$ may each independently be selected from or include, e.g., an unsubstituted or phenyl substituted phenyl group or an unsubstituted or naphthyl substituted phenyl group.

In an implementation, in Formula 2, $Ar_3$ and $Ar_4$ may combine with each other to form a ring. In an implementation, in Formula 2, $Ar_3$ and $Ar_4$ may combine with each other to form a substituted or unsubstituted aryl group. In an implementation, in Formula 2, $Ar_3$ and $Ar_4$ may combine with each other to form a substituted or unsubstituted acridine group.

In an implementation, in Formula 2, $Ar_5$ may be selected from or include, e.g., a substituted or unsubstituted aryl group having 6 to 30 ring carbon atoms, a substituted or unsubstituted heteroaryl group having 5 to 30 ring carbon atoms, a substituted or unsubstituted alkyl group having 1 to 20 carbon atoms, a substituted or unsubstituted silyl group, a halogen atom, a deuterium atom, or a hydrogen atom.

In an implementation, $Ar_5$ may be selected from or include, e.g., a substituted or unsubstituted phenyl group, a substituted or unsubstituted dibenzofuran group, or a substituted or unsubstituted pyridine group.

In an implementation, in Formula 2, $L_2$ may be selected from or include, e.g., a direct linkage, a substituted or unsubstituted alkyl group having 6 to 30 carbon atoms, a substituted or unsubstituted arylene group having 6 to 30 ring carbon atoms, or a substituted or unsubstituted heteroarylene group having 5 to 30 ring carbon atoms.

In an implementation, $L_2$ may be selected from or include, e.g., a substituted or unsubstituted phenylene group, a substituted or unsubstituted divalent biphenyl group, or a substituted or unsubstituted fluorenylene group.

In an implementation, in Formula 2, $R_3$ and $R_4$ may each independently be selected from or include, e.g., a substituted or unsubstituted aryl group having 6 to 30 ring carbon atoms, substituted or unsubstituted heteroaryl group having 5 to 30 ring carbon atoms, a substituted or unsubstituted alkyl group having 1 to 20 carbon atoms, a substituted or unsubstituted silyl group, a halogen atom, a deuterium atom, or a hydrogen atom.

In an implementation, in Formula 2, c may be, e.g., an integer of 0 to 4. In an implementation, in Formula 2, d may be, e.g., an integer of 0 to 3.

In the case where c is an integer of 1 or more (e.g., 1 to 4), a plurality of $R_3$ may be the same or different, or at least one $R_3$ may be different. In the case where d is an integer of 1 or more (e.g., 1 to 3), a plurality of $R_4$ may be the same or different, or at least one $R_4$ may be different.
In an implementation, the second hole transport material may include one of the following Compounds 2-1 to 2-20.
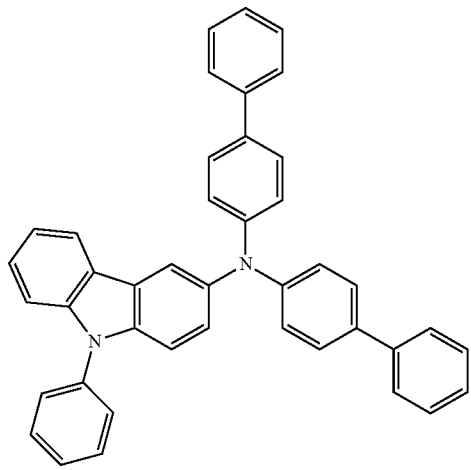
2-1
2-2
2-3
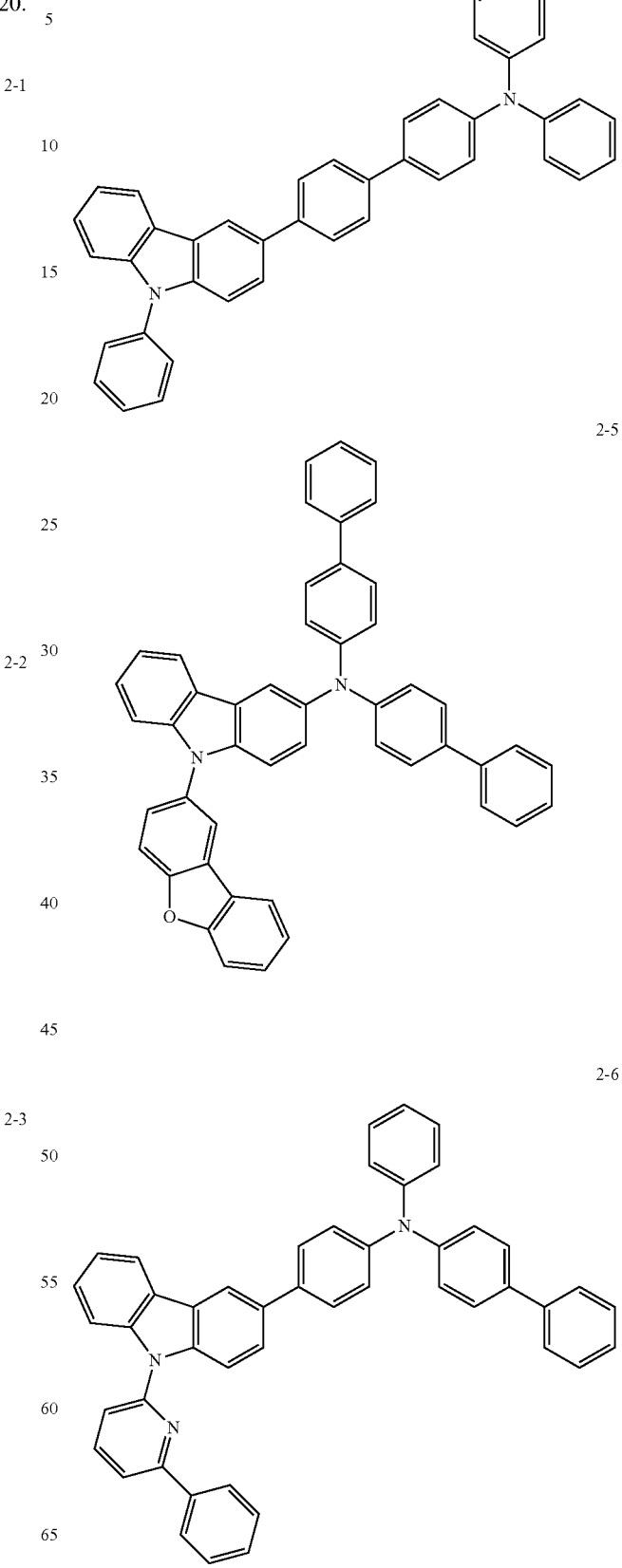
2-4
2-5
2-6

2-7
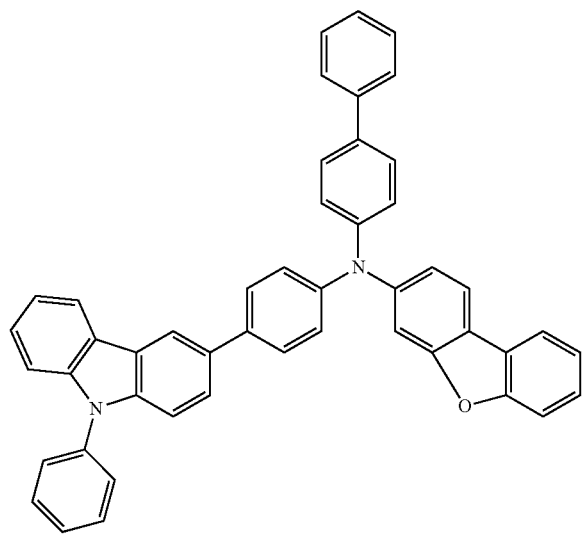
2-10
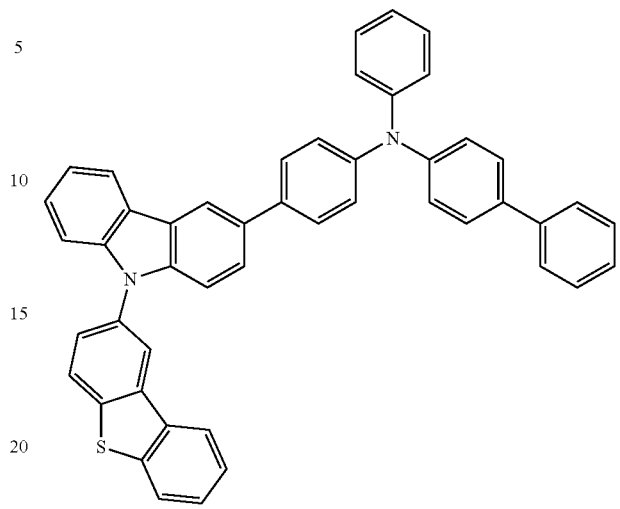
2-8
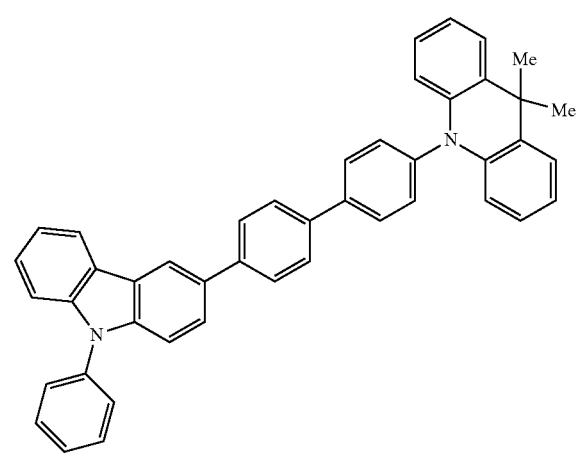
2-11
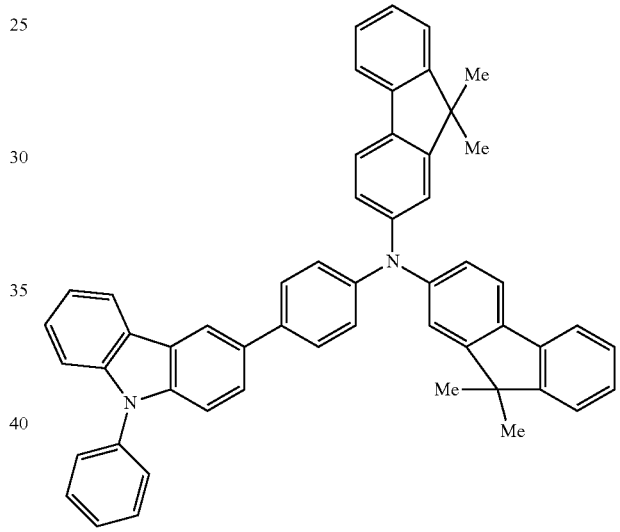
2-9
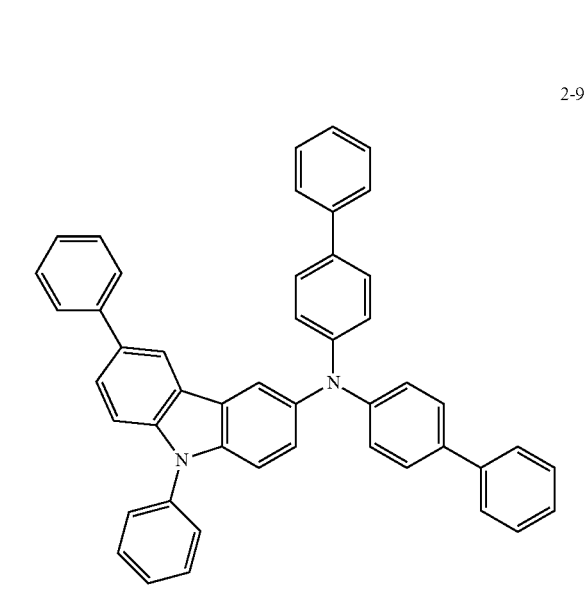
2-12
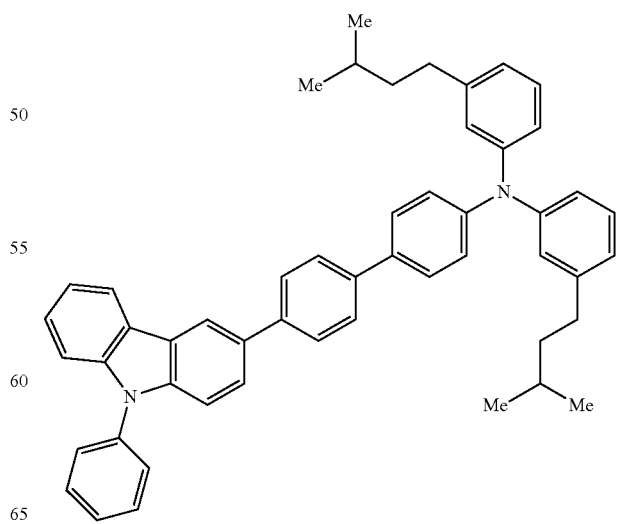

2-13
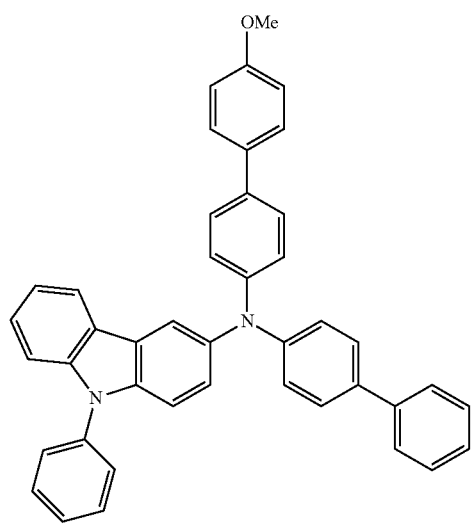
2-14
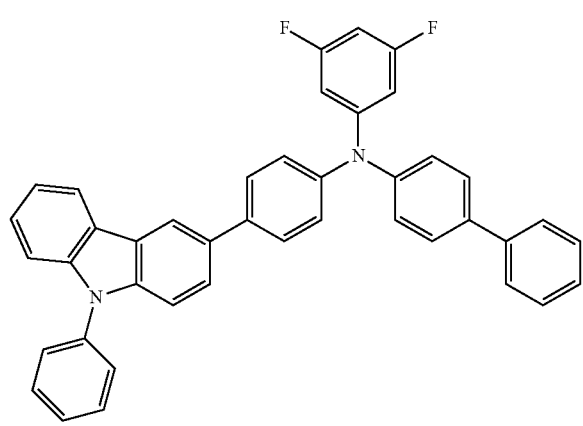
2-15
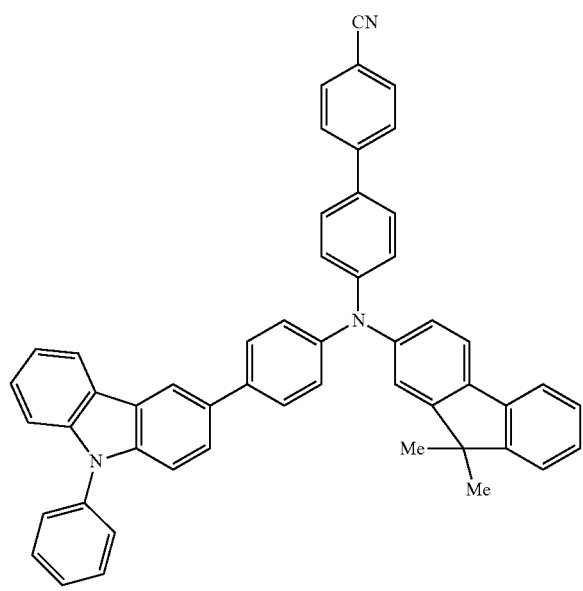
2-16
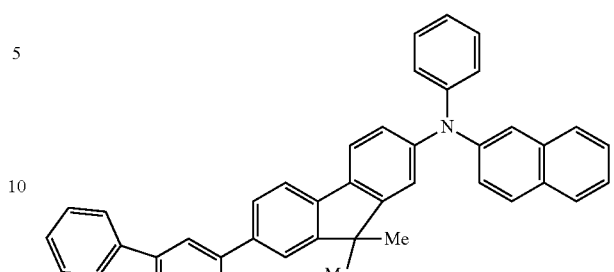
2-17
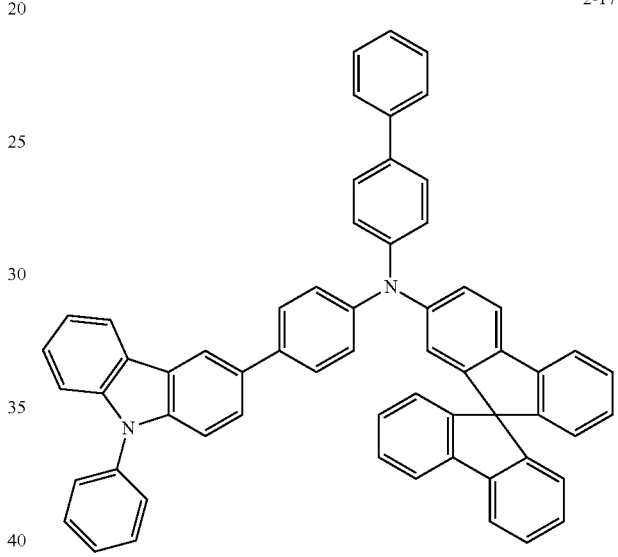
2-18
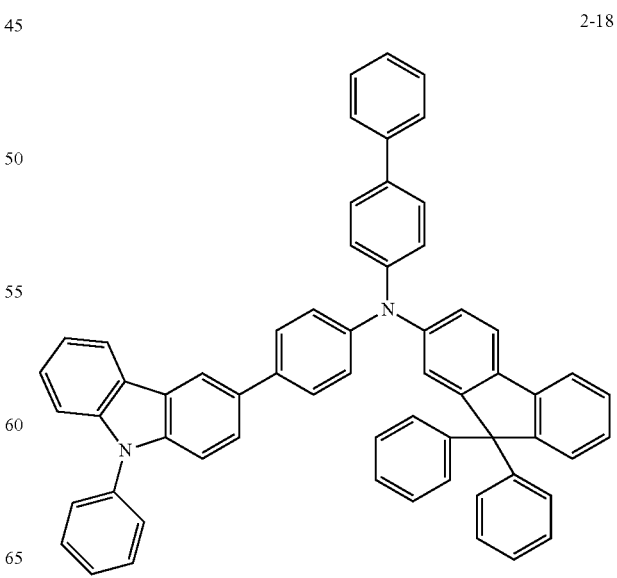

2-19

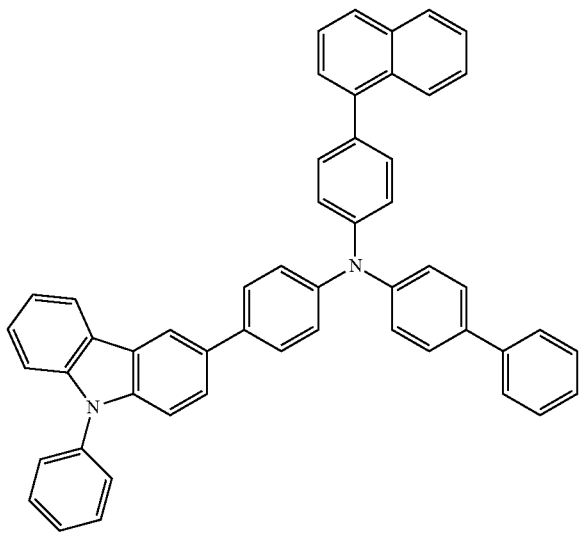

2-20

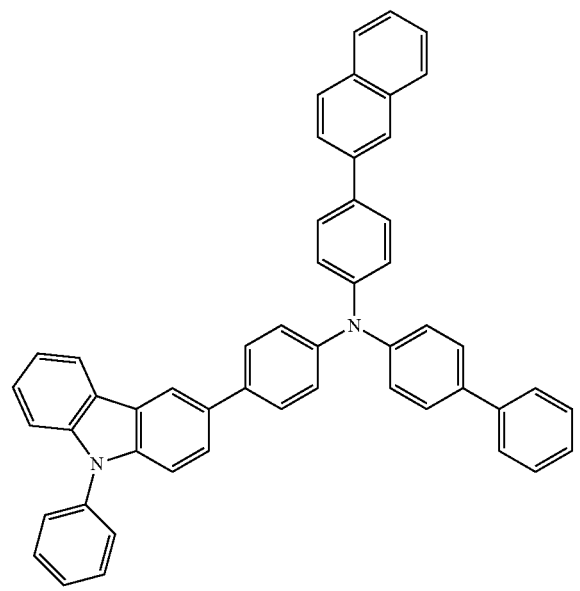

In an implementation, in Formula 3, $Ar_6$ and $Ar_7$ may each independently be selected from or include, e.g., a substituted or unsubstituted aryl group having 6 to 30 ring carbon atoms, a substituted or unsubstituted heteroaryl group hav- ing 5 to 30 ring carbon atoms, a substituted or unsubstituted alkyl group having 1 to 20 carbon atoms, a substituted or unsubstituted silyl group, a halogen atom, a deuterium atom, or a hydrogen atom.

In an implementation, $Ar_6$ and $Ar_7$ may each independently be selected from or include, e.g., a substituted or unsubstituted phenyl group, a substituted or unsubstituted biphenyl group, a substituted or unsubstituted naphthyl group, a substituted or unsubstituted dibenzofuran group, or a substituted or unsubstituted dibenzothiophene group.

In an implementation, $Ar_6$ and $Ar_7$ may each independently be selected from or include, e.g., an unsubstituted or aryl substituted phenyl group, an unsubstituted or silyl substituted phenyl group, an unsubstituted or aryl substituted dibenzothiophene group, or an unsubstituted or aryl substituted biphenyl group.

In an implementation, $Ar_6$ and $Ar_7$ may each independently be selected from or include, e.g., an unsubstituted or phenyl substituted phenyl group, an unsubstituted or naphthyl substituted phenyl group, an unsubstituted or benzo[def]carbazole substituted phenyl group, an unsubstituted or triphenylsilyl substituted phenyl group.

In an implementation, $Ar_6$ and $Ar_7$ may each independently be selected from or include, e.g., an unsubstituted or dibenzofuran substituted biphenyl group, an unsubstituted or benzo[def]carbazole substituted biphenyl group, or an unsubstituted or carbazole substituted biphenyl group.

In an implementation, in Formula 3, $R_5$ may be selected from or include, e.g., a substituted or unsubstituted aryl group having 6 to 30 ring carbon atoms, a substituted or unsubstituted heteroaryl group having 5 to 30 ring carbon atoms, a substituted or unsubstituted alkyl group having 1 to 20 carbon atoms, a substituted or unsubstituted silyl group, a halogen atom, a deuterium atom, or a hydrogen atom.

In an implementation, in Formula 3, $R_5$ may be selected from or include, e.g., a substituted or unsubstituted phenyl group, a substituted or unsubstituted biphenyl group, a substituted or unsubstituted naphthyl group, a substituted or unsubstituted fluorenyl group, a substituted or unsubstituted dibenzofuran group, or a substituted or unsubstituted benzo[def]carbazole group.

In an implementation, in Formula 3, $R_5$ may be selected from or include, e.g., an unsubstituted or silyl substituted phenyl group, an unsubstituted or aryl substituted fluorenyl group, an unsubstituted or aryl substituted phenyl group, an unsubstituted or aryl substituted benzo[def]carbazole group, or an unsubstituted or aryl substituted dibenzofuran group.

In an implementation, in Formula 3, $R_5$ may be selected from or include, e.g., an unsubstituted or naphthyl substituted phenyl group, an unsubstituted or carbazole substituted phenyl group, an unsubstituted or benzo[def]carbazole substituted phenyl group, an unsubstituted or dibenzofuran substituted phenyl group, or an unsubstituted or dibenzofuran substituted biphenyl group.

In Formula 3, e may be, e.g., an integer of 0 to 5. In the case where e is an integer of 1 or more (e.g., 1 to 5), a plurality of $R_5$ may be the same or different, or at least one $R_5$ may be different.

In an implementation, the third hole transport material may include one of the following Compounds 3-1 to 3-20.

3-1
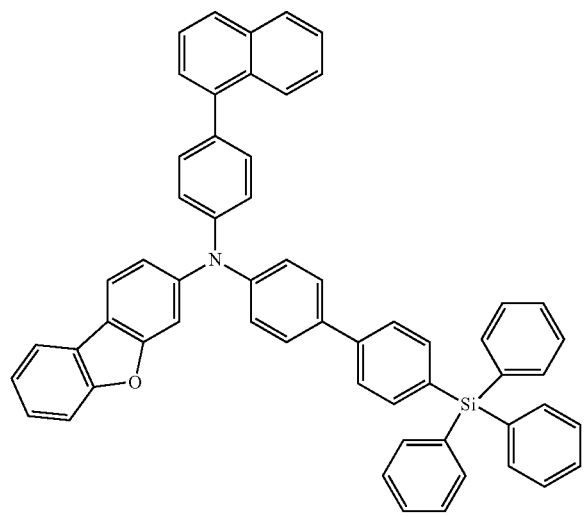
3-2
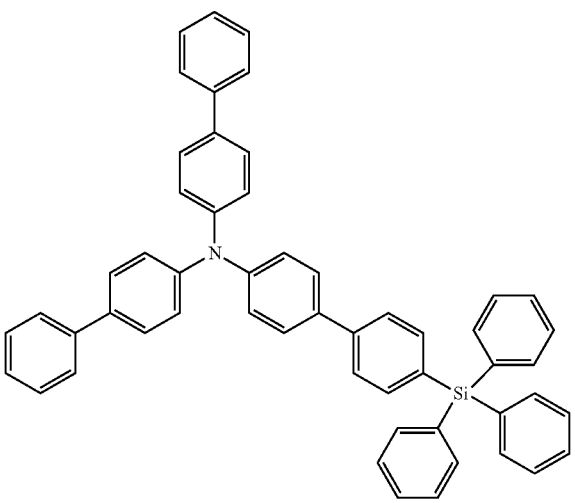
3-3
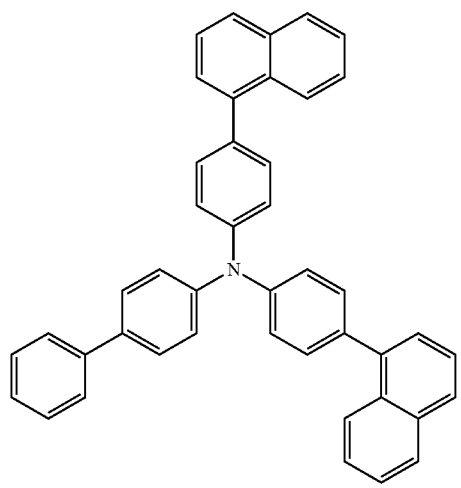
3-4
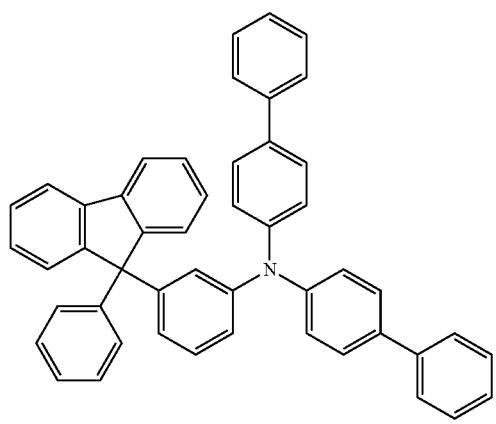
3-5
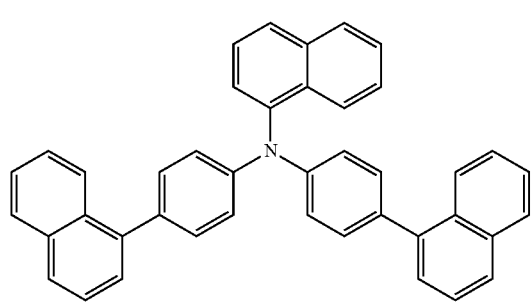
3-6
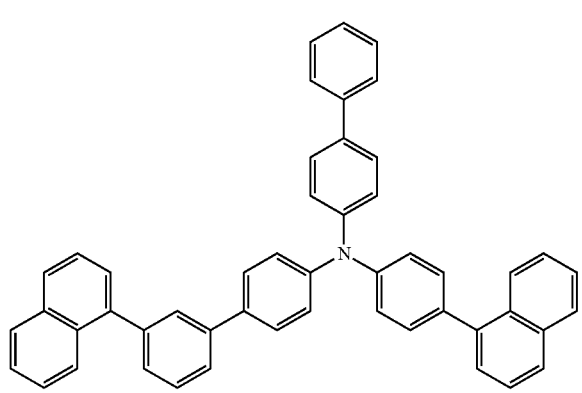

3-7
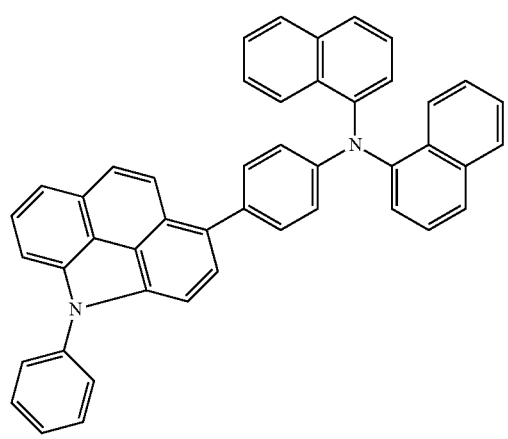
3-8
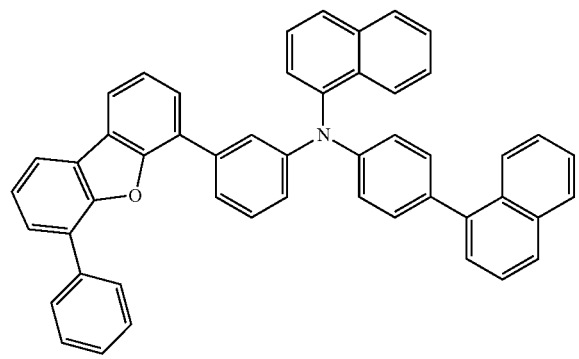
3-9
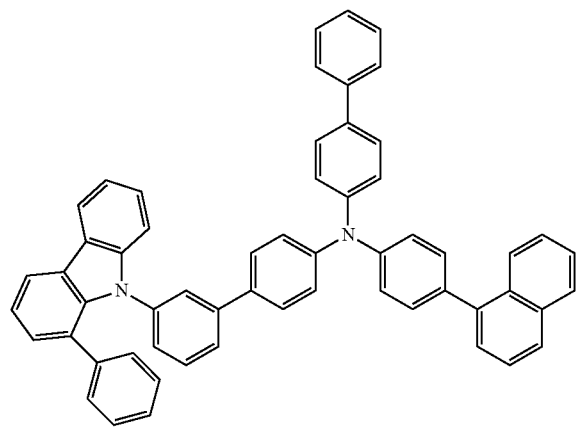
3-10
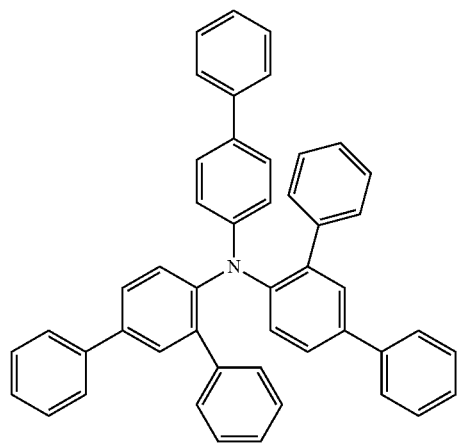
3-11
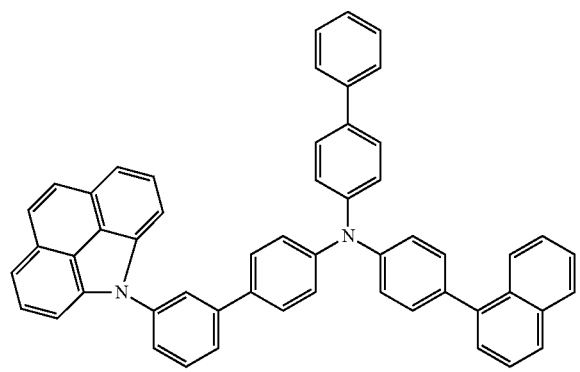
3-12
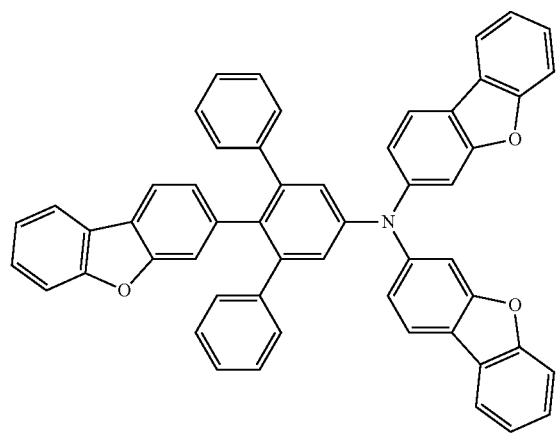

3-13
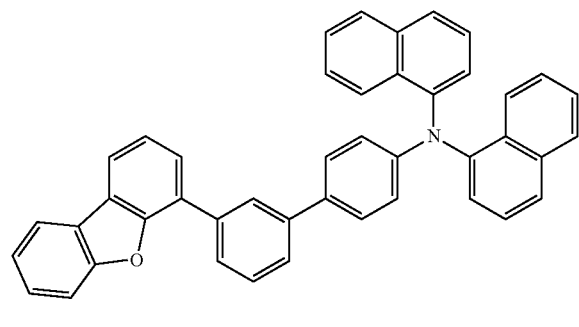
3-14
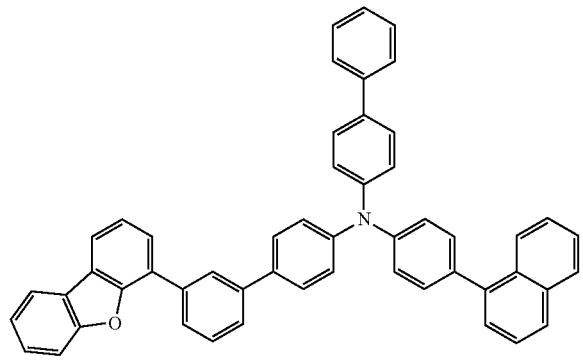
3-15
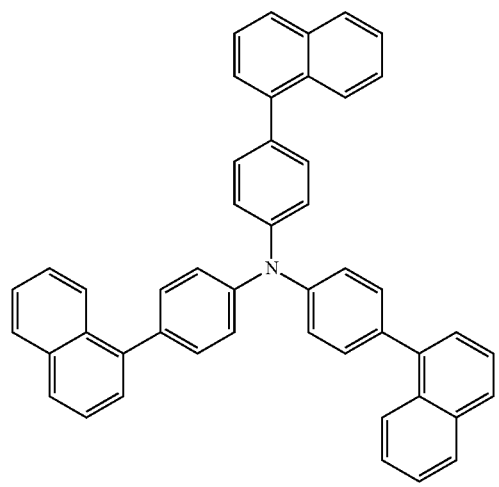
3-16
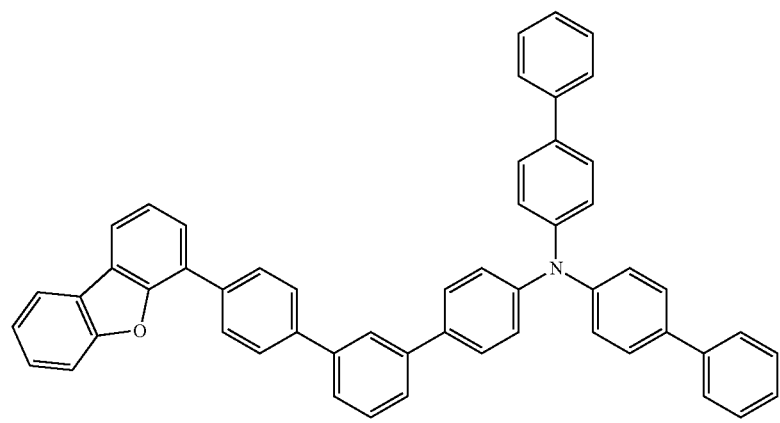

-continued 3-17
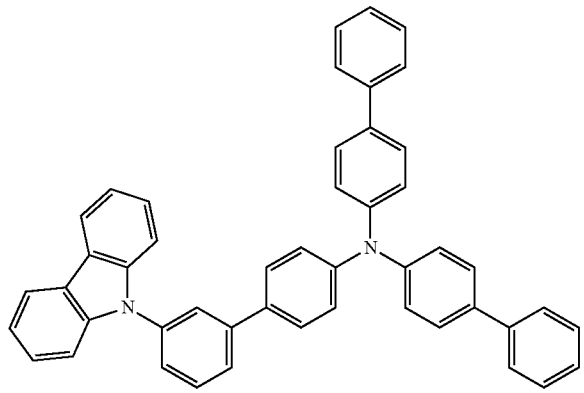

3-18
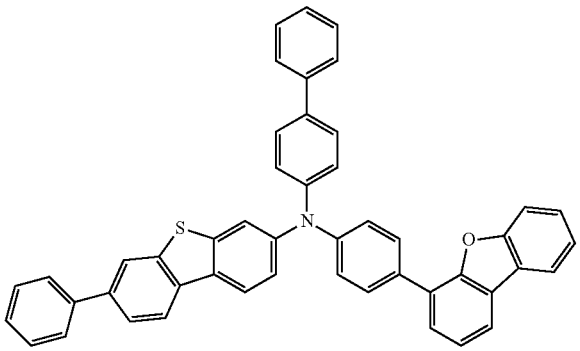

3-19
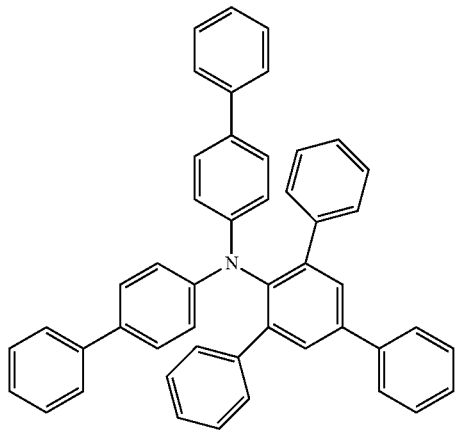

3-20
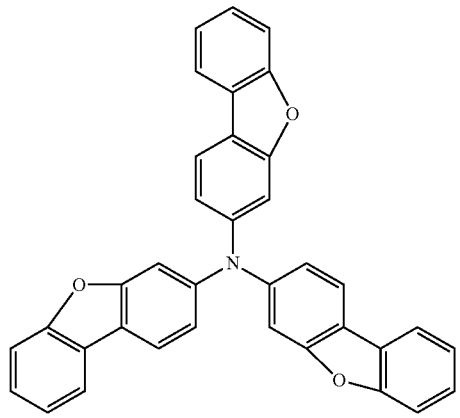

In an implementation, in Formula 4, $Ar_8$ may be selected from or include, e.g., a substituted or unsubstituted aryl group having 6 to 30 ring carbon atoms, a substituted or unsubstituted heteroaryl group having 5 to 30 ring carbon atoms, a substituted or unsubstituted alkyl group having 1 to 20 carbon atoms, a substituted or unsubstituted silyl group, a halogen atom, a deuterium atom, or a hydrogen atom.

In an implementation, in Formula 4, $Ar_8$ may be selected from or include, e.g., a substituted or unsubstituted phenyl group, a substituted or unsubstituted biphenyl group, or a substituted or unsubstituted carbazole group.

In an implementation, in Formula 4, $Ar_8$ may be selected from or include, e.g., an unsubstituted or silyl substituted phenyl group, an unsubstituted or aryl substituted phenyl group, an unsubstituted or aryl substituted biphenyl group, or an unsubstituted or aryl substituted carbazole group.

In an implementation, in Formula 4, $Ar_8$ may be selected from or include, e.g., an unsubstituted or triphenylsilyl substituted phenyl group, an unsubstituted or phenanthryl substituted phenyl group, an unsubstituted or dibenzofuran substituted phenyl group, an unsubstituted or carbazole substituted phenyl group, an unsubstituted or triphenylene substituted phenyl group, or an unsubstituted or phenyl substituted carbazole group.

In an implementation, in Formula 4, $Ar_8$ may combine with at least one of $R_6$ or $R_{13}$ to form a ring. $Ar_8$ may combine with at least one of $R_6$ or $R_{13}$ and thus, the fourth hole transport material may include substituted or unsubstituted benzo furo quinolino acridine in the chemical structure thereof.

In an implementation, in Formula 4, $R_9$ and $R_{10}$ may combine with each other to form a ring that includes X. X may be a direct linkage or $CR_{14}R_{15}$. N and X combining with $Ar_8$ may form a pentagonal ring or a hexagonal ring.

In an implementation, in Formula 4, $R_9$ and $R_{10}$ may combine or bond with each other to form a ring, and thus, the fourth hole transport material may include, e.g., a substituted or unsubstituted indolocarbazole group, a substituted or unsubstituted benzo[def]carbazole group, a substituted or unsubstituted benzocarbazole group, a substituted or unsubstituted benzofurocarbazole group, or a substituted or unsubstituted benzo[def]indolocarbazole group in the compound structure thereof.

In an implementation, in Formula 4, $R_6$, $R_7$, $R_8$, $R_9$, $R_{10}$, $R_{11}$, $R_{12}$, $R_{13}$, $R_{14}$ and $R_{15}$ may each independently be selected from or include, e.g., a substituted or unsubstituted aryl group having 6 to 30 ring carbon atoms, a substituted or unsubstituted heteroaryl group having 5 to 30 ring carbon atoms, a substituted or unsubstituted alkyl group having 1 to 20 carbon atoms, a substituted or unsubstituted silyl group, a halogen atom, a deuterium atom, or a hydrogen atom.

In an implementation, in Formula 4, $R_6$, $R_7$, $R_8$, $R_9$, $R_{10}$, $R_{11}$, $R_{12}$, $R_{13}$, $R_{14}$ and $R_{15}$ may each independently be selected from or include, e.g., a substituted or unsubstituted phenyl group, a substituted or unsubstituted naphthyl group, a substituted or unsubstituted carbazole group, a substituted or unsubstituted benzo[def]carbazole group, a substituted or unsubstituted fluorenyl group, a substituted or unsubstituted dibenzofuran group, a substituted or unsubstituted triphenylene group, a substituted or unsubstituted phenanthrene group, or a substituted or unsubstituted dibenzosilole group.

In an implementation, in Formula 4, $R_6$, $R_7$, $R_8$, $R_9$, $R_{10}$, $R_{11}$, $R_{12}$, $R_{13}$, $R_{14}$ and $R_{15}$ may each independently be selected from or include, e.g., an unsubstituted or aryl substituted phenyl group, an unsubstituted or silyl substituted phenyl group, an unsubstituted or aryl substituted naphthyl group, an unsubstituted or aryl substituted carbazole group, an unsubstituted or aryl substituted benzo[def]carbazole group, an unsubstituted or aryl substituted fluorenyl group, an unsubstituted or aryl substituted dibenzofuran group, an unsubstituted or aryl substituted triphenylene group, an unsubstituted or aryl substituted phenanthrene group, or an unsubstituted or aryl substituted dibenzosilole group.

In an implementation, in Formula 4, $R_6$, $R_7$, $R_8$, $R_9$, $R_{10}$, $R_{11}$, $R_{12}$, $R_{13}$, $R_{14}$ and $R_{15}$ may each independently be selected from or include, e.g., an unsubstituted or triphenylsilyl substituted phenyl group, an unsubstituted or carbazole substituted phenyl group, an unsubstituted or dibenzofuran substituted phenyl, an unsubstituted or carbazole substituted naphthyl group, an unsubstituted or phenyl substituted carbazole group, an unsubstituted or carbazole substituted carbazole group, an unsubstituted or phenyl substituted benzo[def]carbazole group, an unsubstituted or carbazole substituted benzo[def]carbazole group, an unsubstituted or carbazole substituted fluorenyl group, an unsubstituted or carbazole substituted dibenzofuran group, an unsubstituted or benzo[def]carbazole substituted dibenzofuran group, an unsubstituted or carbazole substituted triphenylene group, an unsubstituted or carbazole substituted phenanthrene group, or an unsubstituted or carbazole substituted dibenzosilole group.

In an implementation, the fourth hole transport material may include, e.g., one of the following Compounds 4-1 to 4-20.

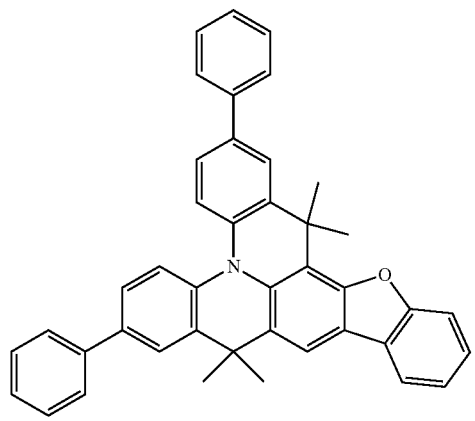

4-1

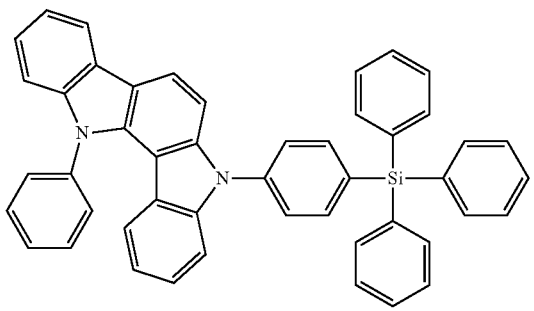

4-2

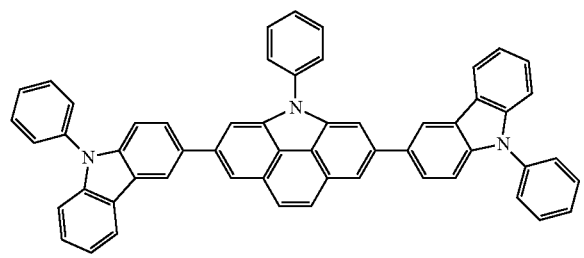

4-3

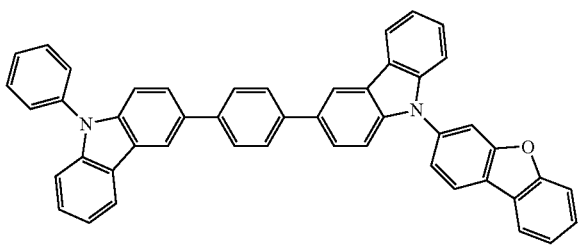

4-4

-continued
4-5
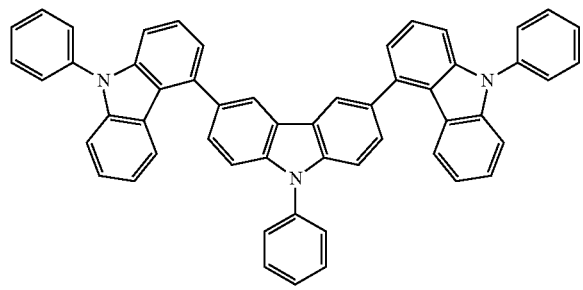
4-6
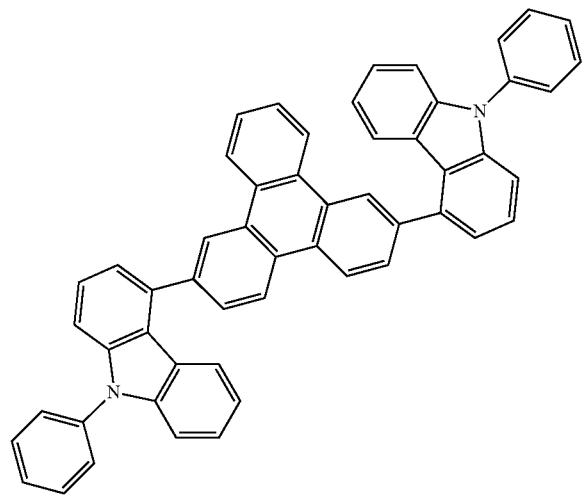
4-7
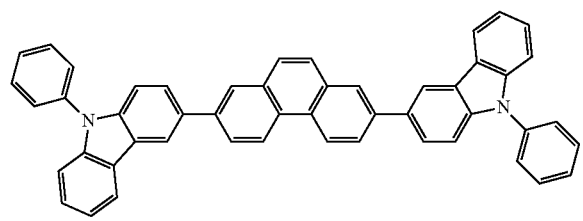
4-8
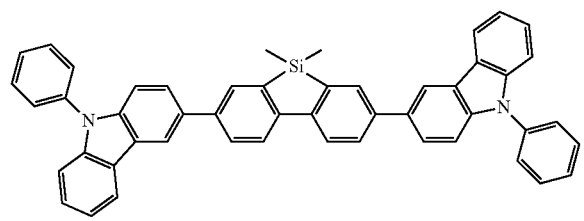
4-9
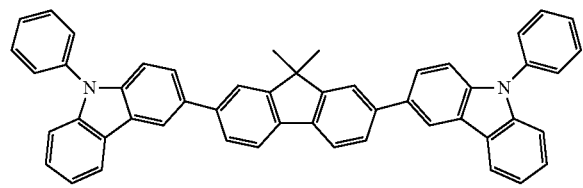
4-10
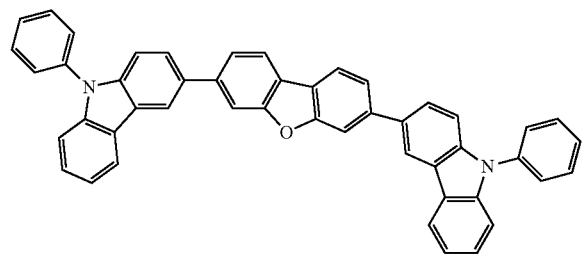
4-11
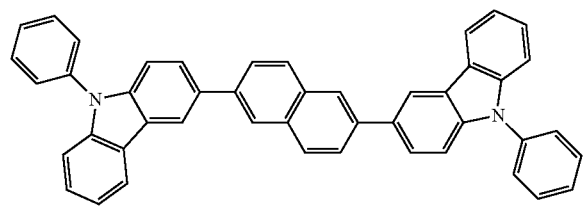
4-12
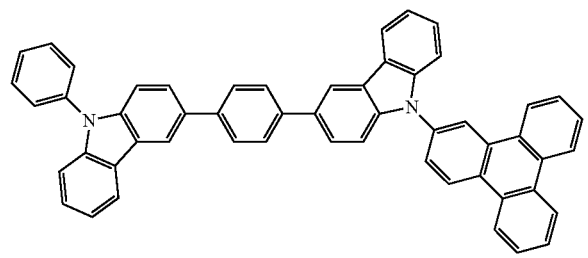

4-13
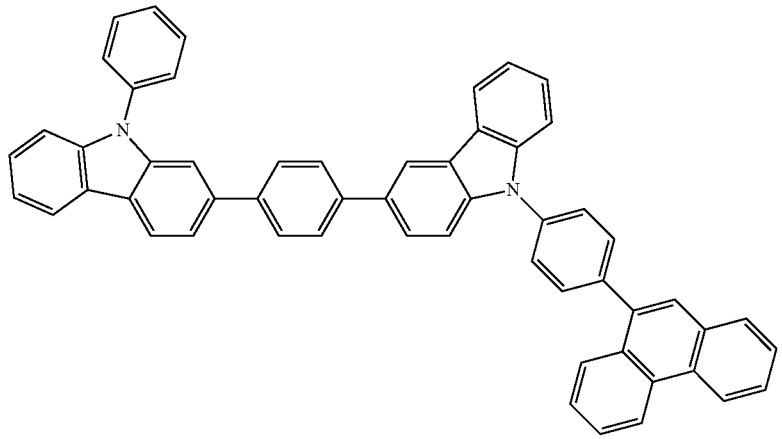
4-14
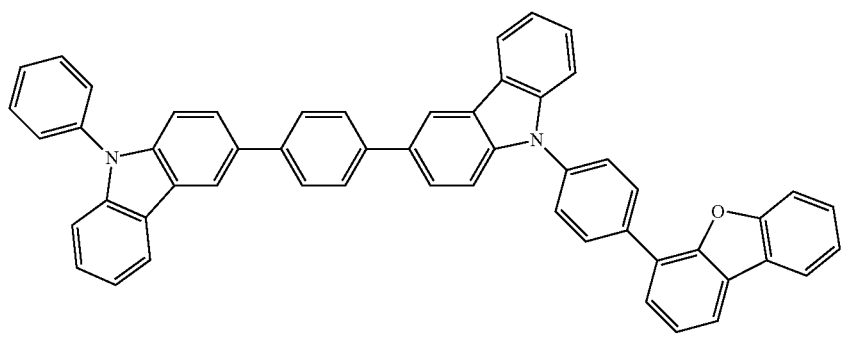
4-15
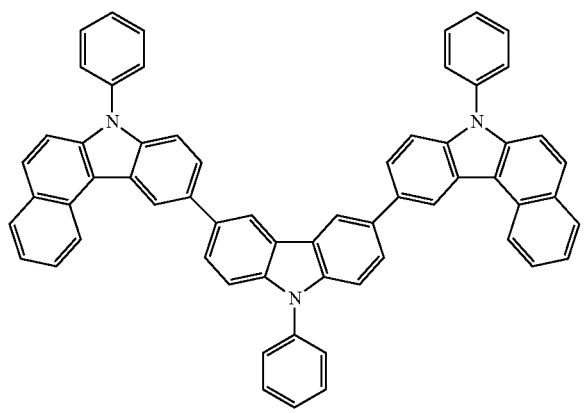
4-16
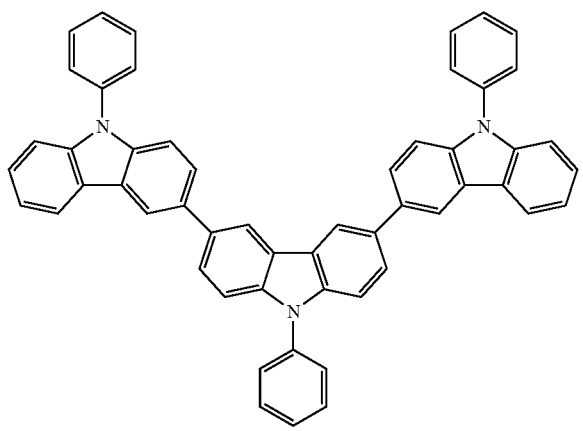
4-17
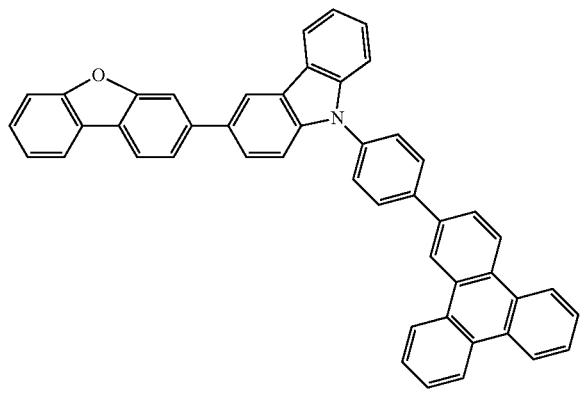
4-18
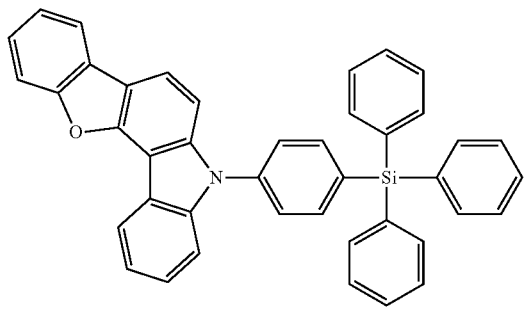

-continued
4-19
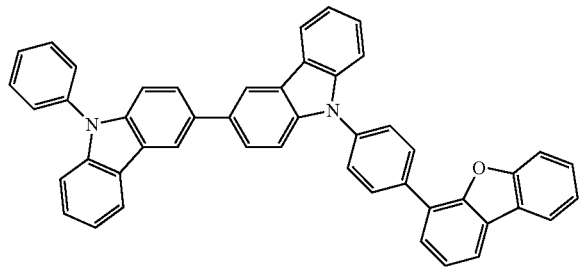
4-20
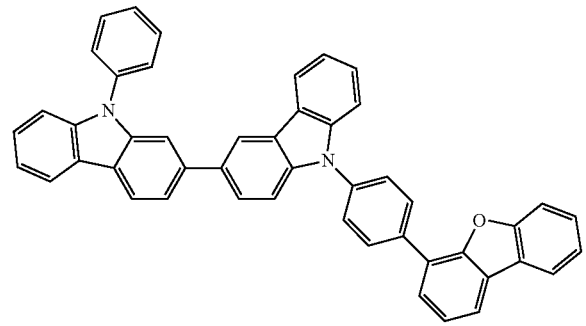
4-21
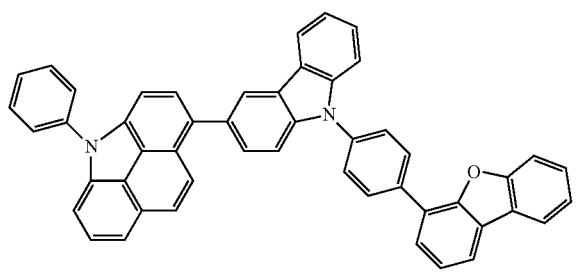
4-22
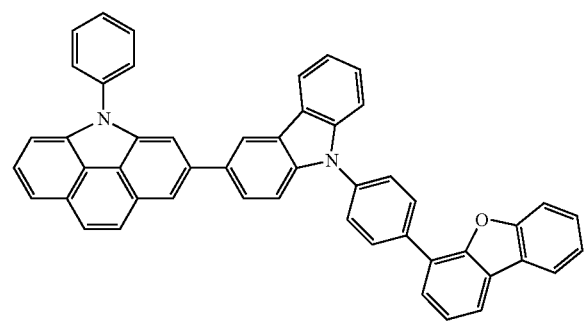
4-23
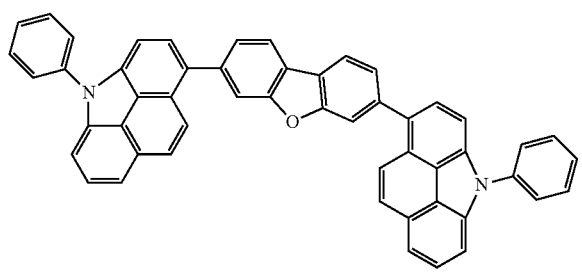
4-24
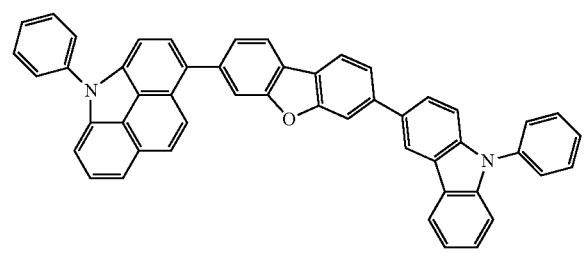
4-25
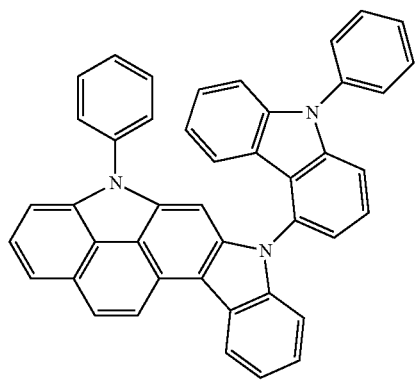
4-26
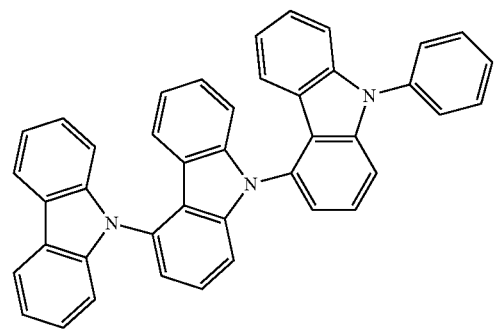

-continued 4-27                    4-28

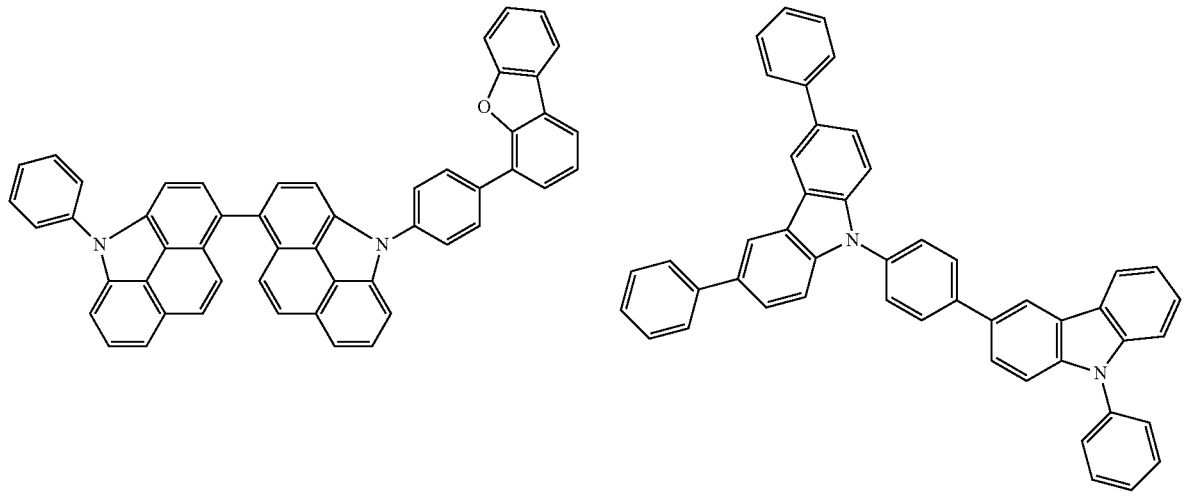

In an implementation, the hole transport region HTR may further include a charge generating material in addition to the above-described materials to help improve conductivity. The charge generating material may be dispersed in the hole transport region HTR uniformly or non-uniformly. The charge generating material may be, e.g., a p-dopant. In an implementation, the p-dopant may be one of a quinone derivative, a metal oxide, or a cyano group-containing compound. Examples of the p-dopant may include a quinone derivative such as tetracyanoquinodimethane (TCNQ), and 2,3,5,6-tetrafluoro-tetracyanoquinodimethane (F4-TCNQ), a metal oxide such as tungsten oxide, and molybdenum oxide.

As described above, the hole transport region HTR may further include at least one of a hole buffer layer or an electron blocking layer in addition to the hole injection layer HIL, the first hole transport layer HTL1 and the second hole transport layer HTL2. The hole buffer layer may help compensate an optical resonance distance according to the wavelength of light emitted from the emission layer EML and increase light emission efficiency. Materials included in the hole transport region HTR may be used as materials included in the hole buffer layer. The electron blocking layer is a layer that helps to prevent electron injection from the electron transport region ETR into the hole transport region HTR.

The emission layer EML may be provided on the hole transport region HTR. The emission layer EML may be provided on the second hole transport layer HTL2. In an implementation, the thickness of the emission layer EML may be, e.g., from about 100 Å to about 300 Å. In an implementation, the emission layer EML may have a single layer formed using a single material, a single layer formed using a plurality of different materials, or a multilayer structure having a plurality of layers formed using a plurality of different materials.

The emission layer EML may emit one of red light, green light, blue light, white light, yellow light, or cyan light. The emission layer EML may include a fluorescent material or a phosphorescent material. The emission layer EML may include a thermally activated delayed fluorescence material. In an implementation, the emission layer EML may include a host and a dopant. The emission layer EML may have a thickness of about 10 nm to about 60 nm.

In an implementation, the host may include, e.g., tris(8-hydroxyquinolino)aluminum (Alq3), 4,4'-bis(N-carbazolyl)-1,1'-biphenyl (CBP), poly(n-vinylcarbazole) (PVK), 9,10-di(naphthaline-2-yl)anthracene (ADN), 4,4',4"-tris (carbazol-9-yl)-triphenylamine (TCTA), 1,3,5-tris(N-phenylbenzimidazole-2-yl)benzene (TPBi), 3-tert-butyl-9,10-di (naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), etc.

In an implementation, the dopant may include an emission material (thermally activated delayed fluorescence material) containing a donor and an acceptor.

When the emission layer EML emits red light, the emission layer EML may include as a host material, e.g., 4,4'-bis(9-carbazolyl)-1,1'-biphenyl (CBP), and 1,3,5-tri[(3-pyridyl)-phen-3-yl]benzene (BmPyPb). The dopant may be selected from, for example, 4,4',4"-(1,3,3a$^1$,4,6,7,9-heptaazaphenalene-2,5,8-triyl)tris(N,N-bis(4-(tert-butyl)phenyl)aniline) (HAP-3TPA), 2,4,6-tri(4-(10H-phenoxazin-10H-yl)phenyl)-1,3,5-triazine (tri-PXZ-TRZ), or derivatives thereof.

When the emission layer EML emits green light, the emission layer EML may include as a host material, e.g., N,N'-dicarbazolyl-3,5-benzene (mCP), and 1,3,5-tri[(3-pyridyl)-phen-3-yl]benzene (BmPyPb). The dopant may be selected from, for example, 1,2,3,5-tetrakis(carbazol-9-yl)-4,6-dicyanobenzene (4CzIPN), 2,5-bis(carbazol-9-yl)-1,4-dicyanobenzene (CzTPN), or derivatives thereof.

When the emission layer EML emits blue light, the emission layer EML may include as a host material, e.g., 4,4',4"-tris(carbazol-9-yl)-triphenylamine (TCTA). The dopant may be selected from, for example, bis[4-(9,9-dimethyl-9,10-dihydroacridine)phenyl]sulfone (DMAC-DSP), 4,5-bis(carbazol-9-yl)-1,2-dicyanobenzene (2CzPN), m-bisCzTRZ, or derivatives thereof.

The electron transport region ETR may be provided on the emission layer EML. In an implementation, the electron transport region ETR may include, e.g., at least one of an electron blocking layer, an electron transport layer ETL or an electron injection layer EIL.

In an implementation, the electron transport region ETR may have a single layer formed using a single material, a single layer formed using a plurality of different materials, or a multilayer structure having a plurality of layers formed using a plurality of different materials.

For example, the electron transport region ETR may have a single layer structure of the electron injection layer EIL or the electron transport layer ETL, or a single layer structure formed using an electron injection material and an electron transport material. In an implementation, the electron transport region ETR may have a single layer structure having a plurality of different materials, or a structure laminated from the anode AN of electron transport layer ETL/electron injection layer EIL, or hole blocking layer/electron transport layer ETL/electron injection layer EIL. In an implementation, the thickness of the electron transport region ETR may be, e.g., from about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

In the case where the electron transport region ETR includes the electron transport layer ETL, the electron transport region ETR may include, e.g., tris(8-hydroxyquinolinato)aluminum (Alq3), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), berylliumbis(benzoquinolin-10-olate (Bebq2), 9,10-di(naphthalene-2-yl)anthracene (ADN), or a mixture thereof. In an implementation, the thickness of the electron transport layer ETL may be from about 100 Å to about 1,000 Å, e.g., about 150 Å to about 500 Å. If the thickness of the electron transport layer ETL satisfies the above-described range, satisfactory electron transport property may be obtained without substantial increase of a driving voltage.

When the electron transport region ETR includes the electron injection layer EIL, the electron transport region ETR may include, e.g., LiF, lithium quinolate (LiQ), $Li_2O$, BaO, NaCl, CsF, a metal in lanthanoides such as Yb, or a metal halide such as RbCl and RbI. In an implementation, the electron injection layer EIL also may be formed using a mixture material of an electron transport material and an insulating organo metal salt. The organo metal salt may be a material having an energy band gap of about 4 eV or more. In an implementation, the organo metal salt may include, e.g., a metal acetate, a metal benzoate, a metal acetoacetate, a metal acetylacetonate, or a metal stearate. In an implementation, the thickness of the electron injection layer EIL may be from about 1 Å to about 100 Å, or from about 3 Å to about 90 Å. In the case where the thickness of the electron injection layer EIL satisfies the above described range, satisfactory electron injection property may be obtained without inducing the substantial increase of a driving voltage.

The electron transport region ETR may include a hole blocking layer as described above. In an implementation, the hole blocking layer may include, e.g., at least one of 2,9-dimethyl-4,7-diphenyl-1,10-phenanthroline (BCP), or 4,7-diphenyl-1,10-phenanthroline (Bphen).

The cathode CAT may be provided on the electron transport region ETR. The cathode CAT may be a common electrode or a negative electrode. The cathode CAT may be a transmissive electrode, a transflective electrode, or a reflective electrode. In the case where the cathode CAT is the transmissive electrode, the cathode CAT may include a transparent metal oxide, e.g., ITO, IZO, ZnO, ITZO, etc.

In the case where the cathode CAT is the transflective electrode or the reflective electrode, the cathode CAT may include, e.g., Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). In an implementation, the cathode CAT may have a multilayered structure including a reflective layer or a transflective layer formed using the above-described materials and a transparent conductive layer formed using ITO, IZO, ZnO, ITZO, etc.

In an implementation, the cathode CAT may be connected with an auxiliary electrode. In the case where the cathode CAT is connected with the auxiliary electrode, the resistance of the cathode CAT may decrease.

In the organic light emitting device 10, according to the application of a voltage to each of the anode AN and the cathode CAT, holes injected from the anode AN may move via the hole transport region HTR to the emission layer EML, and electrons injected from the cathode CAT may move via the electron transport region ETR to the emission layer EML. The electrons and the holes may be recombined in the emission layer EML to generate excitons, and the excitons may emit light via transition from an excited state to a ground state.

In the case where the organic light emitting device 10 is a top emission type, the anode AN may be a reflective electrode, and the cathode CAT may be a transmissive electrode or a transflective electrode. In the case where the organic light emitting device 10 is a bottom emission type, the anode AN may be a transmissive electrode or a transflective electrode, and the cathode CAT may be a reflective electrode.

The organic light emitting device according to an embodiment of the present disclosure may include, e.g., a first hole transport layer including a first hole transport material or a second hole transport material (each containing an amine) and a second hole transport layer including a third hole transport material (containing one amine group) or a fourth hole transport material (containing a ring that includes N). Each of the first hole transport material and the second hole transport material may include the amine, and hole transport properties may be high. The third hole transport material may include the one amine group and the fourth hole transport material may include the N-containing ring, charge tolerance may be high. Accordingly, a charge balance of holes and electrons in an emission layer may be appropriate in the organic light emitting device according to an embodiment of the present disclosure, and high emission efficiency and long life may be accomplished.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

Synthetic Examples

[Synthesis of Compounds]
(Synthesis of Compound A)

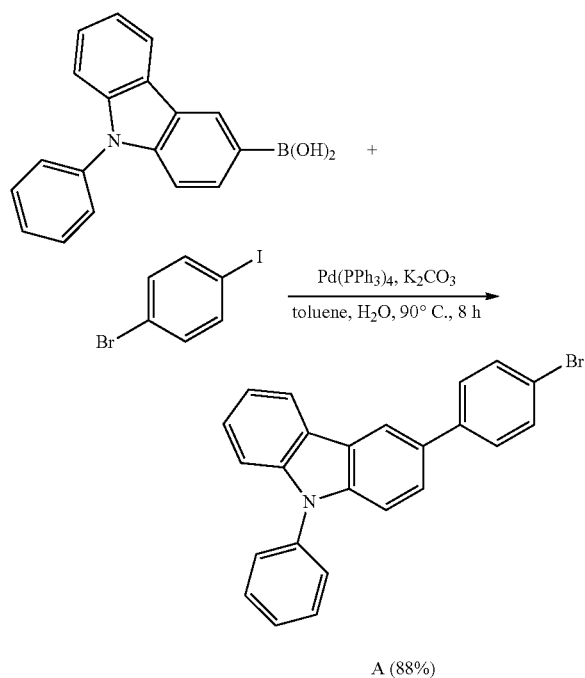

A (88%)

Under an Ar atmosphere, 2.87 g of 9-phenylcarbazole-3-boronic acid, 2.99 g of 1-bromo-4-iodobenzene, 0.33 g of Pd(PPh$_3$)$_4$, and 1.86 g of potassium carbonate were added to a 200 mL, three-necked flask and were heated and stirred in a mixed solvent of 50 mL of toluene and 20 mL of water at about 90° C. for about 8 hours. After cooling in the air, water was added, an organic layer was separated, and solvents were distilled. The crude product thus obtained was separated by silica gel column chromatography (using a mixed solvent of dichloromethane and hexane) and recrystallized using a mixed solvent of toluene and hexane to obtain 3.50 g (yield 88%) of Compound A as a white solid. The molecular weight of Compound A as measured by FAB-MS was 398. FAB-MS was measured using JMS-700V manufactured by JEOL Co., and 1H-NMR was measured using AVAVCE300M manufactured by Bruker Biospin KK Co.

(Synthesis of Compound 2-3)

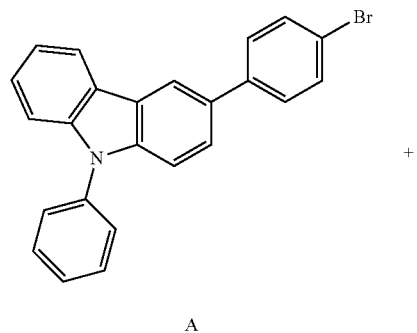

A

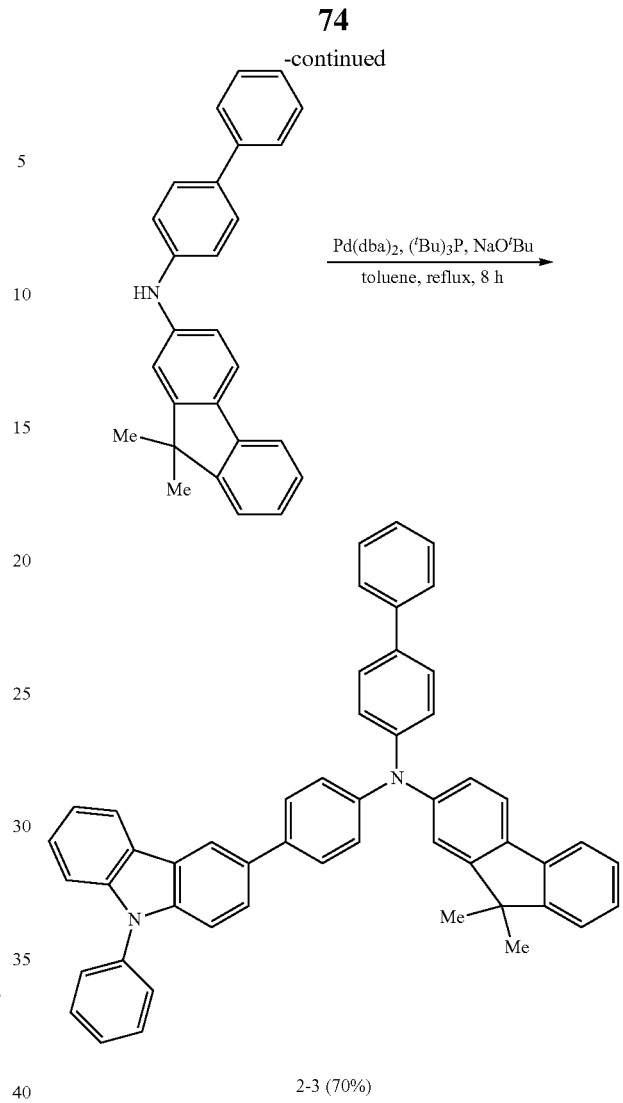

2-3 (70%)

Under an Ar atmosphere, 3.98 g of Compound A, 3.62 g of N-[1,1'-biphenyl]-4-yl-9,9-dimethyl-9H-fluoren-2-amine, 0.563 g of Pd(dba)$_2$, 0.19 g of (t-Bu)$_3$P, and 6.44 g of sodium t-butoxide were added to a 200 mL, three-necked flask and were heated and refluxed in 130 mL of a toluene solvent for about 8 hours. After cooling in the air, water was added, an organic layer was separated, and solvents were distilled. The crude product thus obtained was separated by silica gel column chromatography (using a mixed solvent of toluene and hexane) and recrystallized using a mixed solvent of toluene and hexane to obtain 4.75 g (yield 70%) of Compound 2-3 as a yellow solid. The molecular weight of Compound 2-3 measured by FAB-MS was 679. FAB-MS was measured using JMS-700V manufactured by JEOL Co., and $^1$H-NMR was measured using AVAVCE300M manufactured by Bruker Biospin KK Co.

(Synthesis of Compound 2-11)

Compound 2-11 was synthesized by performing the same synthetic method described in Synthesis of Compound 2-3 except for using N-(9,9-dimethyl-9H-fluoren-2-yl)-9,9-dimethyl-9H-fluoren-2-amine instead of N-[1,1'-biphenyl]-4-yl-9,9-dimethyl-9H-fluoren-2-amine. The molecular weight of Compound 2-11 measured by FAB-MS was 719. FAB-MS was measured using JMS-700V manufactured by JEOL Co., and $^1$H-NMR was measured using AVAVCE300M manufactured by Bruker Biospin KK Co.

(Synthesis of Compound 2-19)

Compound 2-19 was synthesized by performing the same synthetic method described in Synthesis of Compound 2-3 except for using N-[4-(1-naphthalenyl)phenyl]-[1,1'-biphenyl]-4-amine instead of N-[1,1'-biphenyl]-4-yl-9,9-dimethyl-9H-fluoren-2-amine. The molecular weight of Compound 2-19 measured by FAB-MS was 689. FAB-MS was measured using JMS-700V manufactured by JEOL Co., and $^1$H-NMR was measured using AVAVCE300M manufactured by Bruker Biospin KK Co.

(Synthesis of Compound 3-2)

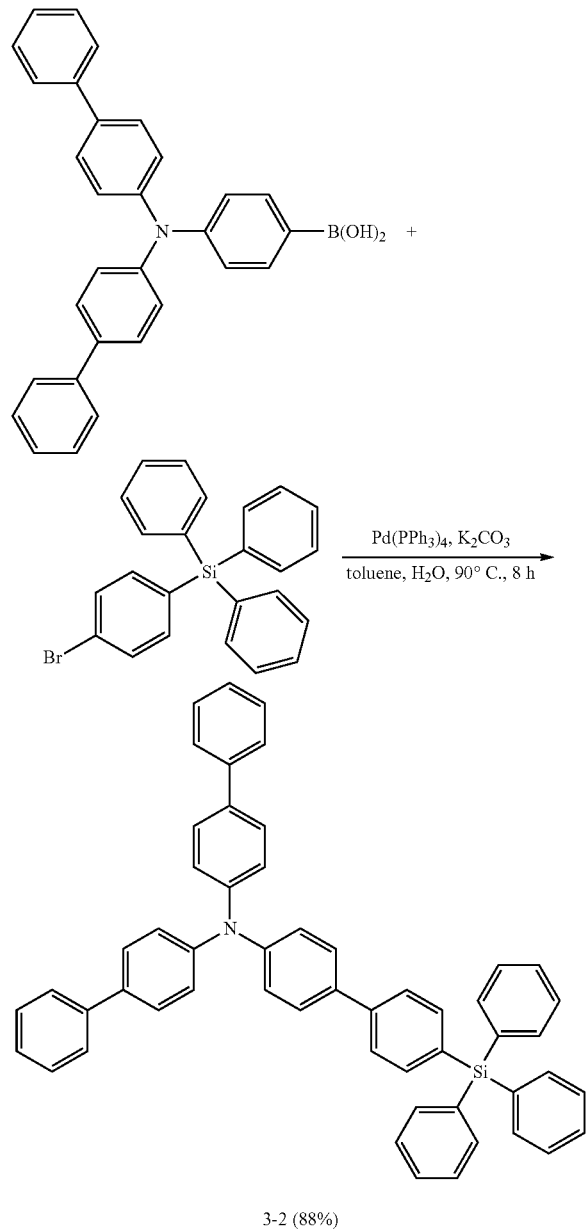

3-2 (88%)

Under an Ar atmosphere, 4.40 g of (4-(bis(1,1'-biphenyl)-4-yl)amino) phenylboronic acid, 4.15 g of 4-bromotetraphenylsilane, 2.263 g of Pd(PPh$_3$)$_4$, and 2.44 g of potassium carbonate were added to a 200 mL, three-necked flask and were heated and stirred in a mixed solvent of 50 mL of toluene and 20 mL of water at about 90° C. for about 8 hours. After cooling in the air, water was added, an organic layer was separated, and solvents were distilled. The crude product thus obtained was separated by silica gel column chromatography (using a mixed solvent of dichloromethane and hexane) and recrystallized using a mixed solvent of toluene and hexane to obtain 6.33 g (yield 88%) of Compound 3-2 as a white solid. The molecular weight of Compound 3-2 measured by FAB-MS was 719. FAB-MS was measured using JMS-700V manufactured by JEOL Co., and $^1$H-NMR was measured using AVAVCE300M manufactured by Bruker Biospin KK Co.

(Synthesis of Compound 3-17)

Compound 3-17 was synthesized by performing the same synthetic method described in Synthesis of Compound 3-2 except for using 9-(3-bromophenyl)-9H-carbazole instead of 4-bromotetraphenylsilane. The molecular weight of Compound 3-17 measured by FAB-MS was 639. FAB-MS was measured using JMS-700V manufactured by JEOL Co., and $^1$H-NMR was measured using AVAVCE300M manufactured by Bruker Biospin KK Co.

[Manufacture of Organic Light Emitting Device]

An anode was formed using ITO to a thickness of about 150 nm, a hole injection layer was formed using 2,3,6,7,10,11-hexacyano-1,4,5,8,9,12-hexaazatriphenylene (HAT-CN) to a thickness of about 5 nm, a first hole transport layer was formed using a material shown in the following Table 1 to a thickness of about 10 nm, a second hole transport layer was formed using a material shown in the following Table 1 to a thickness of about 100 nm, an emission layer was formed using 2,4,5,6-tetrakis(carbazol-9-yl)-1,3-dicyanobenzene (4CzIPN) and 3,3-di(9H-carbazol-9-yl)biphenyl (mCBP) to a thickness of about 20 nm, a first electron transport layer was formed using 2,4,6-tris(biphenyl-3-yl)-1,3,5-triaxine (T2T) to a thickness of about 5 nm, a second electron transport layer was formed using BPy-TP2 to a thickness of about 25 nm, an electron injection layer was formed using LiF to a thickness of about 1 nm, and a cathode was formed using Al to a thickness of about 100 nm.

The current density of a device was measured using Source Meter of 2400 Series manufactured by Keithley Instruments Co., a voltage was measured using CS-200 Chroma Meter manufactured by Konica Minolta Holdings Co., and emission efficiency was measured using PC Program LabVIEW8.2 for measurement, manufactured by National Instruments Co., Ltd. in Japan.

TABLE 1

| Device manufacturing example | First hole transport layer | Second hole transport layer | Emission efficiency (cd/A) | Life (h) (LT90) |
|---|---|---|---|---|
| Example 1 | 1-1 | 3-2 | 41 | 150 |
| Example 2 | 1-3 | 3-8 | 40 | 145 |
| Example 3 | 1-10 | 3-10 | 42 | 149 |
| Example 4 | 2-3 | 3-15 | 41 | 160 |
| Example 5 | 2-11 | 3-16 | 40 | 162 |
| Example 6 | 2-19 | 3-17 | 41 | 164 |
| Example 7 | 1-17 | 3-5 | 42 | 153 |
| Example 8 | 1-18 | 3-6 | 41 | 155 |
| Example 9 | 2-7 | 3-5 | 40 | 156 |
| Example 10 | 2-19 | 3-6 | 40 | 154 |
| Example 11 | 1-1 | 4-2 | 41 | 150 |
| Example 12 | 1-3 | 4-8 | 41 | 151 |
| Example 13 | 1-10 | 4-10 | 42 | 153 |

TABLE 1-continued

| Device manufacturing example | First hole transport layer | Second hole transport layer | Emission efficiency (cd/A) | Life (h) (LT90) |
|---|---|---|---|---|
| Example 14 | 2-3 | 4-15 | 41 | 161 |
| Example 15 | 2-11 | 4-16 | 42 | 158 |
| Example 16 | 2-19 | 4-17 | 41 | 162 |
| Comparative Example 1 | Tris-PCz | — | 28 | 80 |
| Comparative Example 2 | 2-3 | Comparative Compound 1 | 29 | 95 |

Tris-PCz: 9,9'-diphenyl-6-(9-phenyl-9H-carbazol-3-yl)-9H,9'H-3,3'-bicarbazole
Comparative Compound 1

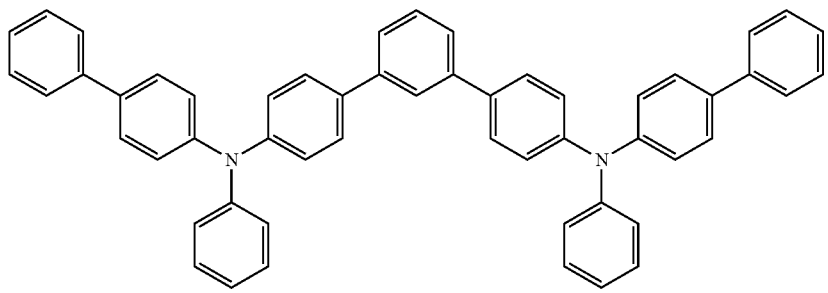 [SMILES: c1ccc(-c2ccc(N(c3ccccc3)c3ccc(-c4cccc(-c5ccc(N(c6ccccc6)c6ccc(-c7ccccc7)cc6)cc5)c4)cc3)cc2)cc1]

Referring to Table 1, the organic light emitting devices of Examples 1 to 16 had higher emission efficiency and longer life than the organic light emission devices of Comparative Examples 1 and 2. In Comparative Example 1, Tris-PCz (not including amine) was included as the material of a first hole transport layer but was not included in a second hole transport layer. Accordingly, a hole transport property was low, charge balance was low, and device life was short. In addition, in Comparative Example 2, Comparative Compound 1 (which is a diamine compound) was included in a second hole transport layer, and charge tolerance was low, and thus, device life was short.

By way of summation and review, in the application of an organic light emitting device to a display device, a decrease of the driving voltage, an increase of emission efficiency, and an increase of life of the organic light emitting device may be desirable.

The organic light emitting device according to an embodiment of the present disclosure may accomplish high emission efficiency and long life.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An organic light emitting device, comprising:
   an anode;
   a hole transport region on the anode;
   an emission layer on the hole transport region;
   an electron transport region on the emission layer; and
   a cathode on the electron transport region,
   wherein the hole transport region comprises:
   a first hole transport material represented by the following Formula 1 or Formula 2; and
   a second hole transport material represented by the following Formula 3 or Formula 4:

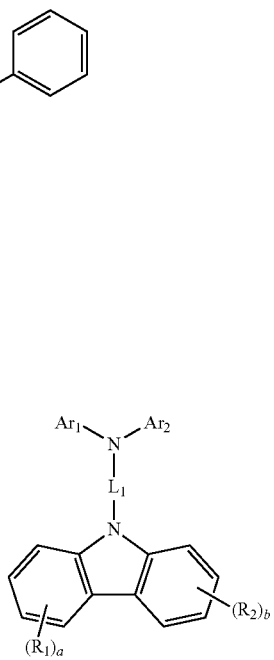

[Formula 1]

[Formula 2]

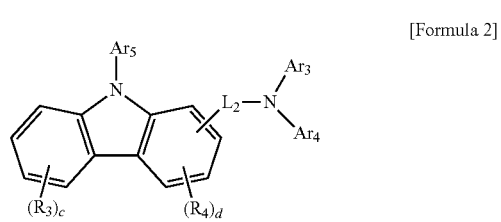

[Formula 3]

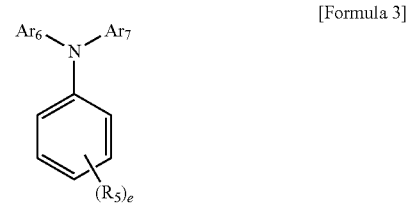

[Formula 4]

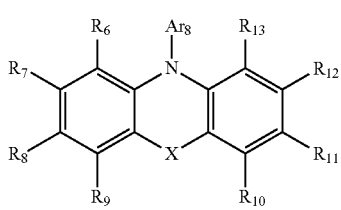

wherein, in Formulae 1, 2, 3 and 4, $Ar_1$, $Ar_2$, $Ar_3$, $Ar_4$, $Ar_5$, and $Ar_8$ are each independently a substituted or unsubstituted aryl group having 6 to 30 ring carbon atoms, a substituted or unsubstituted heteroaryl group having 5 to 30 ring carbon atoms, a substituted or unsubstituted alkyl group having 1 to 20 carbon atoms, a substituted or unsubstituted silyl group, a halogen atom, a deuterium atom, or a hydrogen atom, $Ar_6$ and $Ar_7$ are each independently a substituted aryl group having 6 to 30 ring carbon atoms, an unsubstituted aryl group having 10 to 30 ring carbon atoms, a substituted or unsubstituted heteroaryl group having 5 to 30 ring carbon atoms, a substituted or unsubstituted alkyl group having 1 to 20 carbon atoms, a substituted or unsubstituted silyl group, a halogen atom, a deuterium atom, or a hydrogen atom, provided that, in $Ar_6$ and $Ar_7$, a substituent of the substituted aryl group having 6 to 30 ring carbon atoms, the substituted heteroaryl group having 5 to 30 ring carbon atoms, the substituted alkyl group having 1 to 20 carbon atoms, and the substituted silyl group does not include an amino group, and provided that neither $Ar_6$ nor $Ar_7$ are a substituted fluorenyl group, X is a direct linkage or $CR_{14}R_{15}$, $R_1$ to $R_{15}$ are each independently a substituted or unsubstituted aryl group having 6 to 30 ring carbon atoms, a substituted or unsubstituted heteroaryl group having 5 to 30 ring carbon atoms, a substituted or unsubstituted alkyl group having 1 to 20 carbon atoms, a substituted or unsubstituted silyl group, a halogen atom, a deuterium atom, or a hydrogen atom, $R_1$ to $R_{15}$ are separate or combined with an adjacent group to form a ring, $R_5$ is a substituted or unsubstituted aryl group having 6 to 30 ring carbon atoms, a substituted or unsubstituted heteroaryl group having 5 to 30 ring carbon atoms, a substituted or unsubstituted alkyl group having 1 to 20 carbon atoms, a substituted or unsubstituted silyl group, a halogen atom, a deuterium atom, or a hydrogen atom, provided that, in $R_5$, a substituent of the substituted aryl group having 6 to 30 ring carbon atoms, the substituted heteroaryl group having 5 to 30 ring carbon atoms, the substituted alkyl group having 1 to 20 carbon atoms, and the substituted silyl group does not include an amino group, $L_1$ and $L_2$ are each independently a direct linkage, a substituted or unsubstituted alkyl group having 6 to 30 carbon atoms, a substituted or unsubstituted arylene group having 6 to 30 ring carbon atoms, or a substituted or unsubstituted heteroarylene group having 5 to 30 ring carbon atoms, a, b, and c are each independently an integer of 0 to 4, d is an integer of 0 to 3, and e is an integer of 0 to 5, wherein the emission layer comprises a thermally activated delayed fluorescence material.

2. The organic light emitting device as claimed in claim 1, wherein $Ar_1$ and $Ar_2$ in Formula 1 are each independently a substituted or unsubstituted phenyl group, a substituted or unsubstituted biphenyl group, a substituted or unsubstituted naphthyl group, a substituted or unsubstituted fluorenyl group, or a substituted or unsubstituted acridine group.

3. The organic light emitting device as claimed in claim 1, wherein Li in Formula 1 is a substituted or unsubstituted phenylene group, a substituted or unsubstituted divalent biphenyl group, or a substituted or unsubstituted fluorenylene group.

4. The organic light emitting device as claimed in claim 1, wherein the first hole transport material represented by the Formula 1 comprises one of the following Compounds:

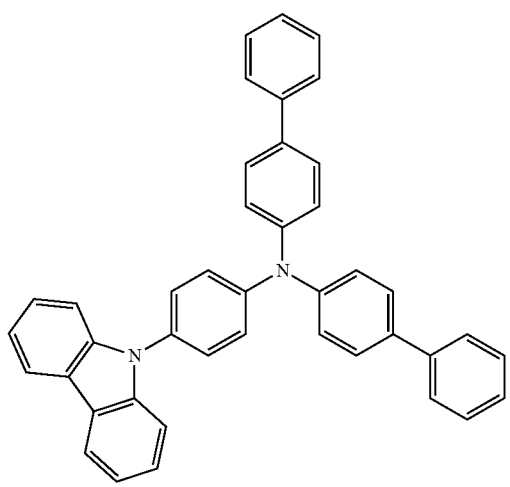

1-1

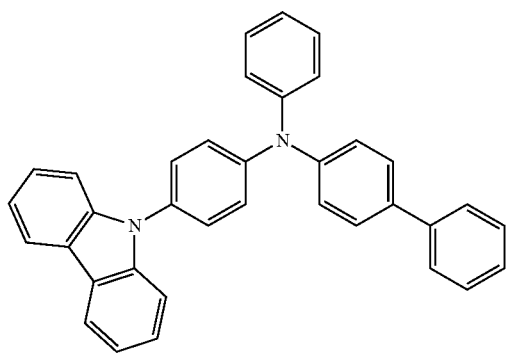

1-2

1-3
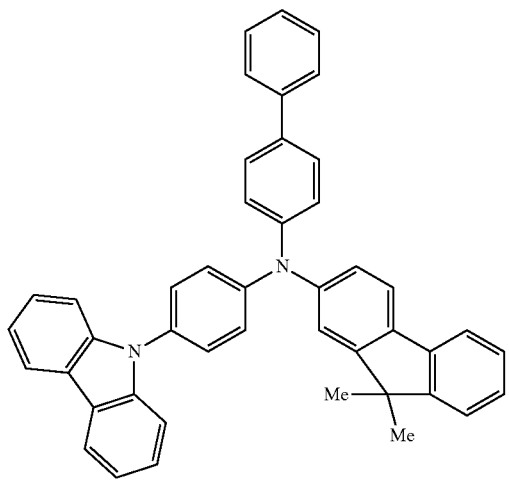
1-4
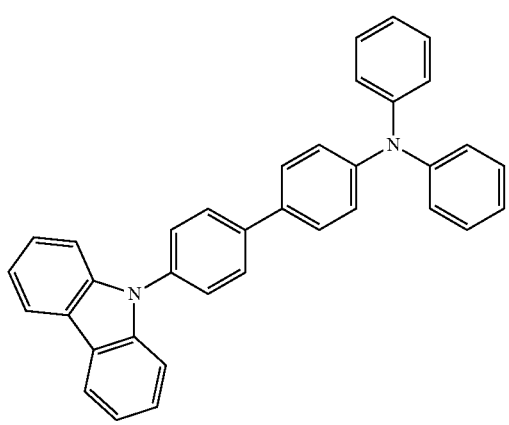
1-7
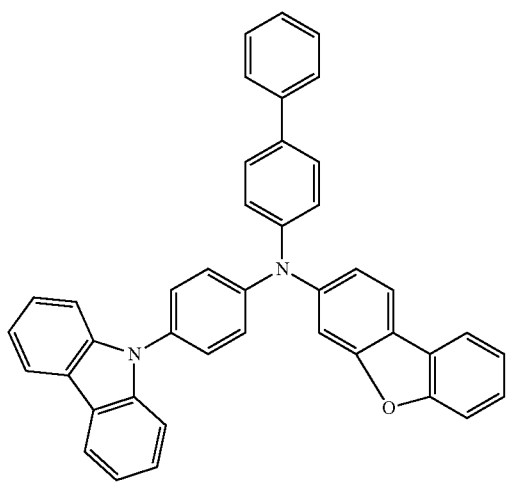
1-8
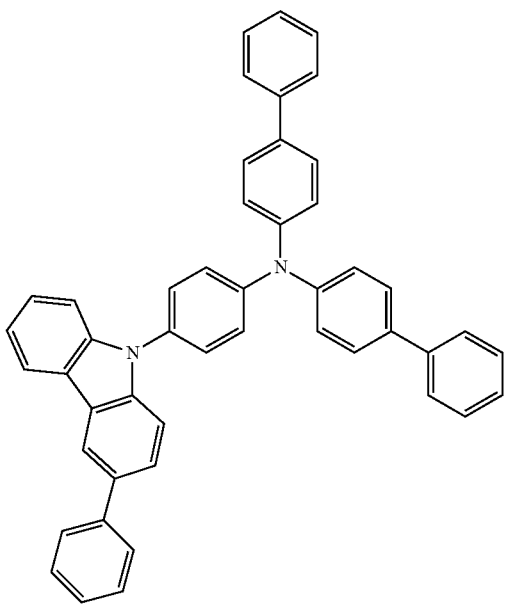
1-9
1-10
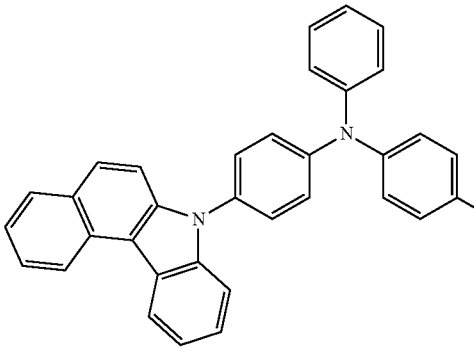

1-11
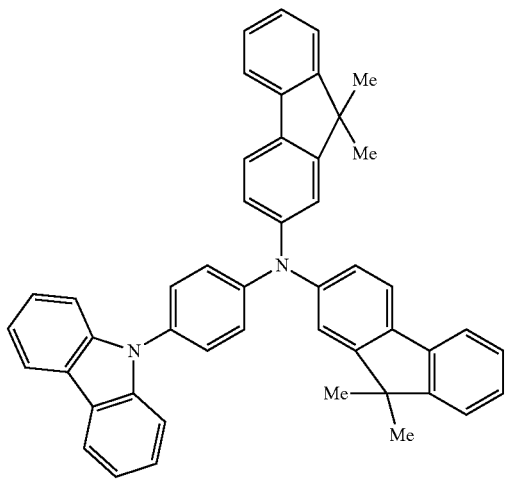
1-12
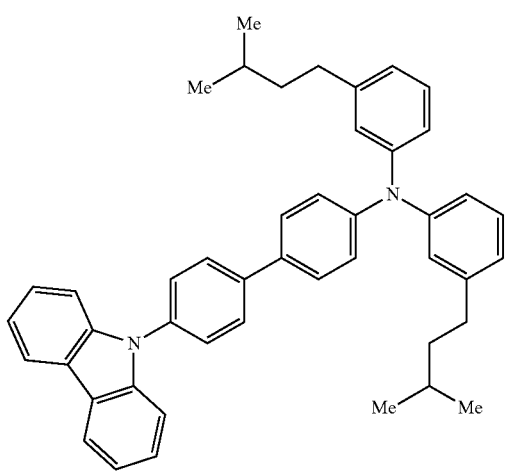
1-13
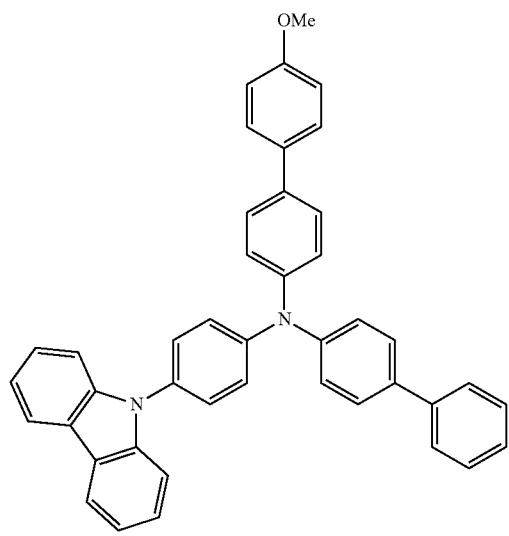
1-14
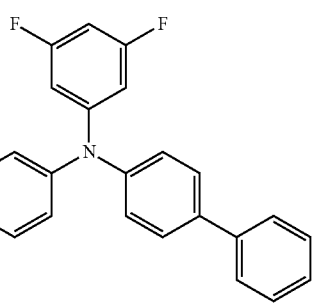
1-15
1-16
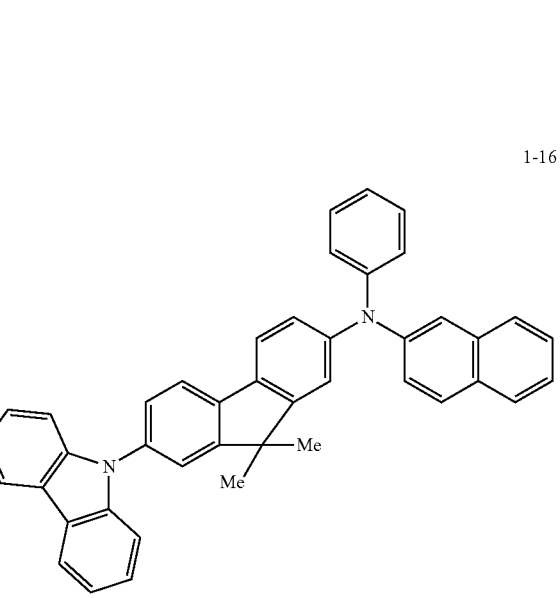

1-17

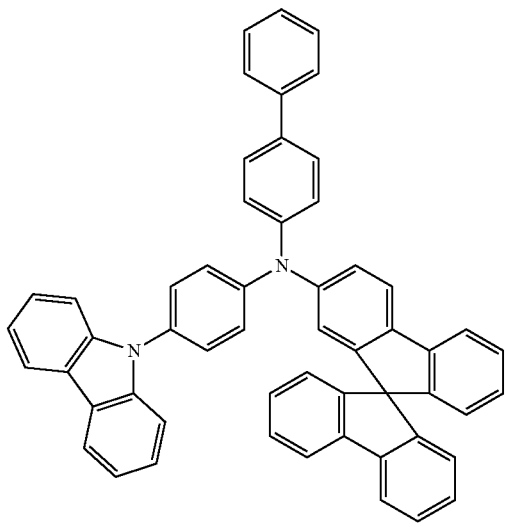

1-18

1-19

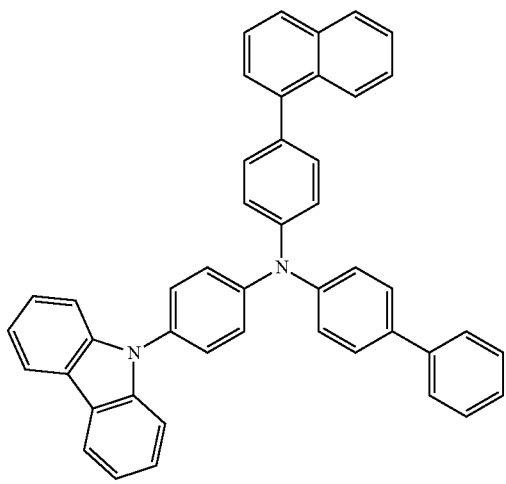

1-20

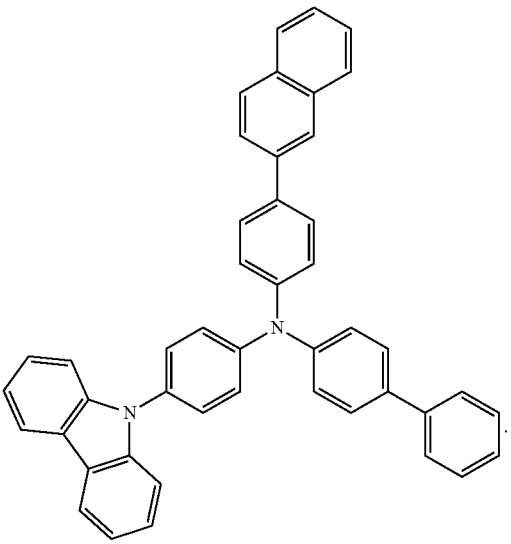

5. The organic light emitting device as claimed in claim 1, wherein $Ar_3$ and $Ar_4$ in Formula 2 are bound to form a ring.

6. The organic light emitting device as claimed in claim 1, wherein $Ar_3$ and $Ar_4$ in Formula 2 are each independently a substituted or unsubstituted phenyl group, a substituted or unsubstituted biphenyl group, a substituted or unsubstituted naphthyl group, a substituted or unsubstituted fluorenyl group, or a substituted or unsubstituted spirobifluorenyl group.

7. The organic light emitting device as claimed in claim 1, wherein $Ar_5$ in Formula 2 is a substituted or unsubstituted phenyl group, a substituted or unsubstituted dibenzofuran group, or a substituted or unsubstituted pyridine group.

8. The organic light emitting device as claimed in claim 1, wherein $L_2$ in Formula 2 is a direct linkage, a substituted or unsubstituted phenylene group, a substituted or unsubstituted divalent biphenyl group, or a substituted or unsubstituted fluorenylene group.

9. The organic light emitting device as claimed in claim 1, wherein the first hole transport material represented by Formula 2 comprises one of the following Compounds 2-1 to 2-20:

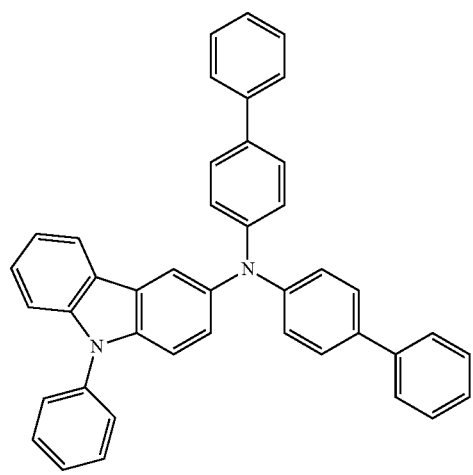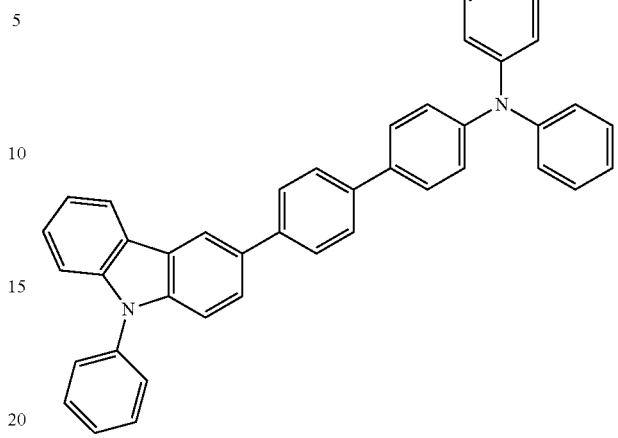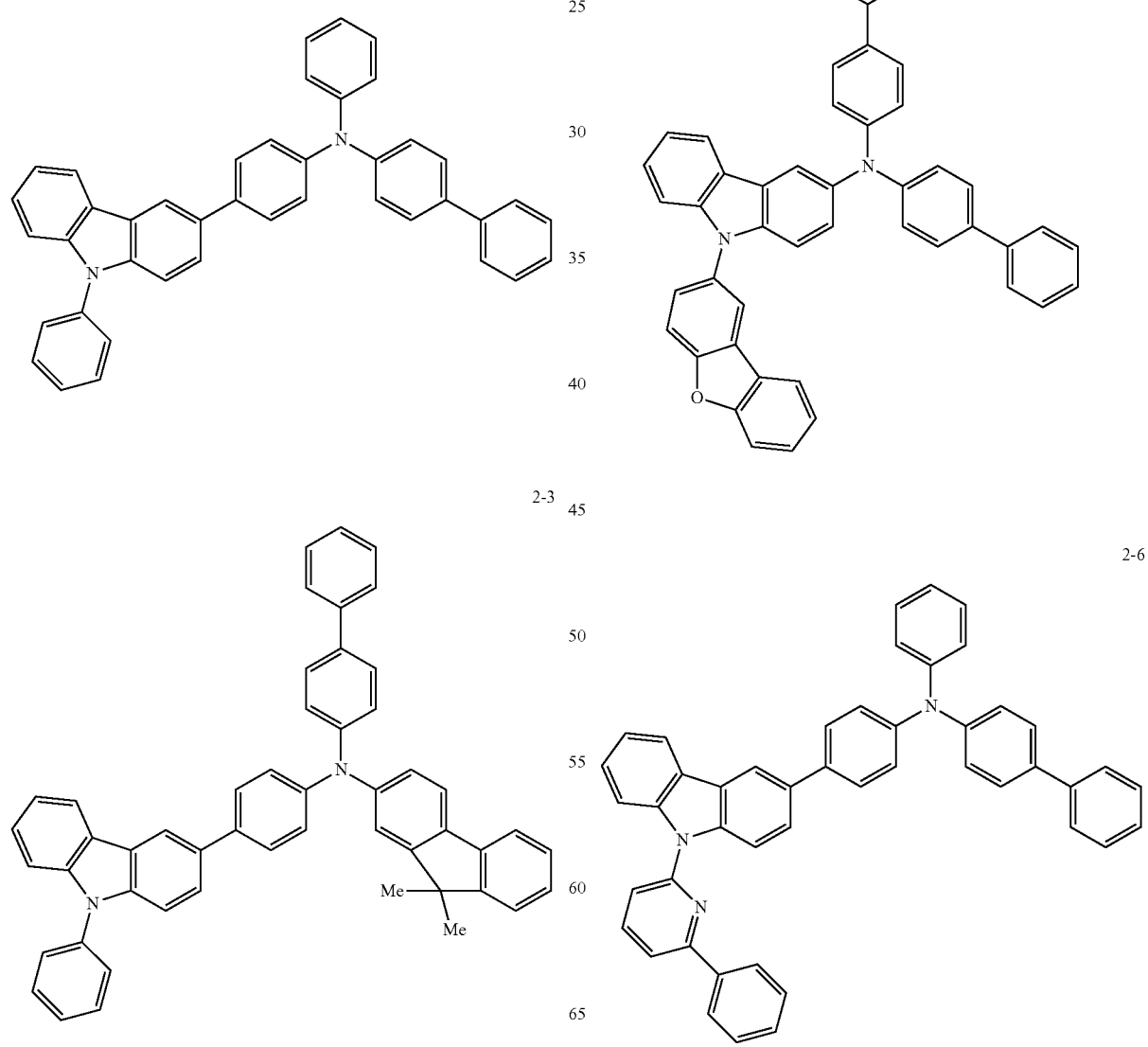

2-7
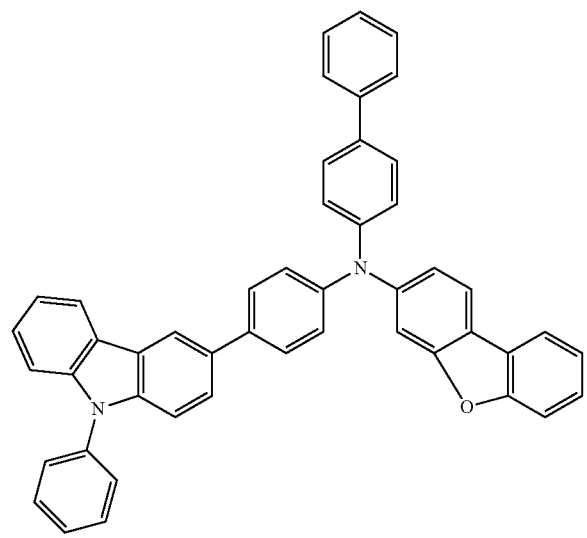
2-10
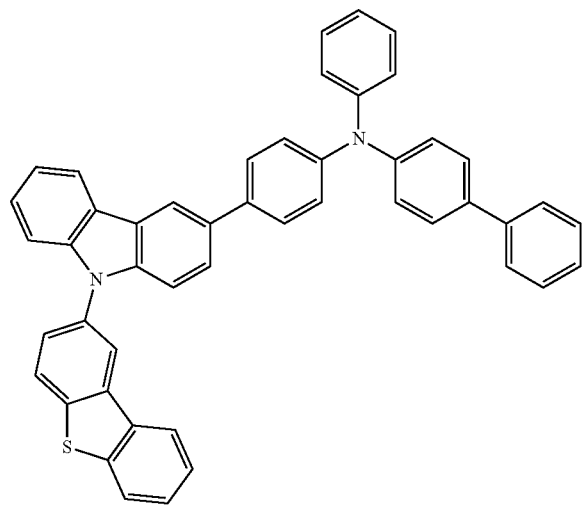
2-8
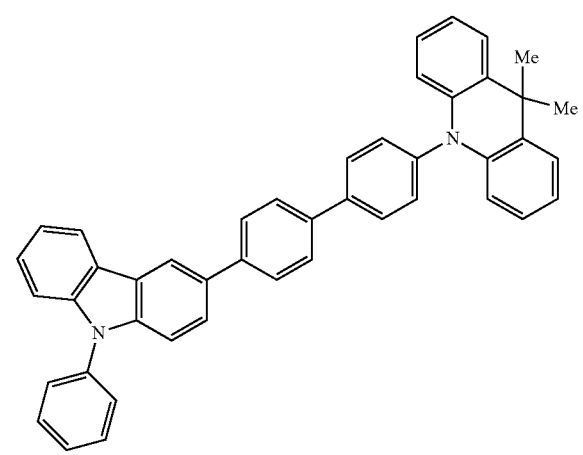
2-11
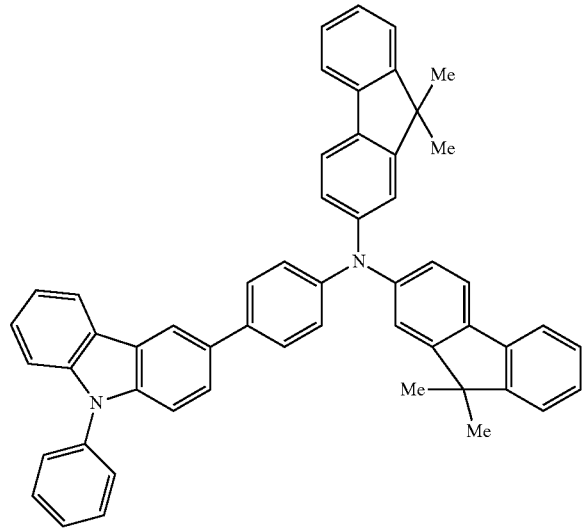
2-9
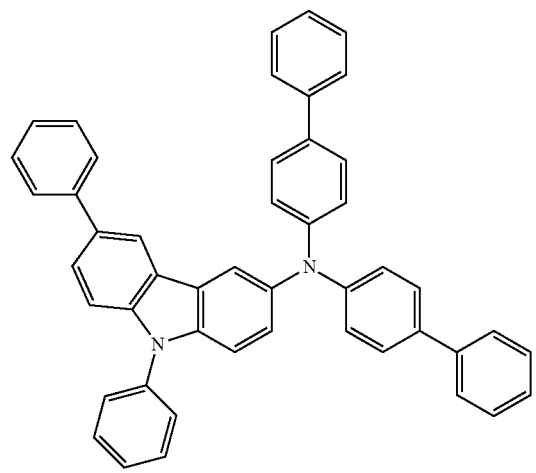
2-12
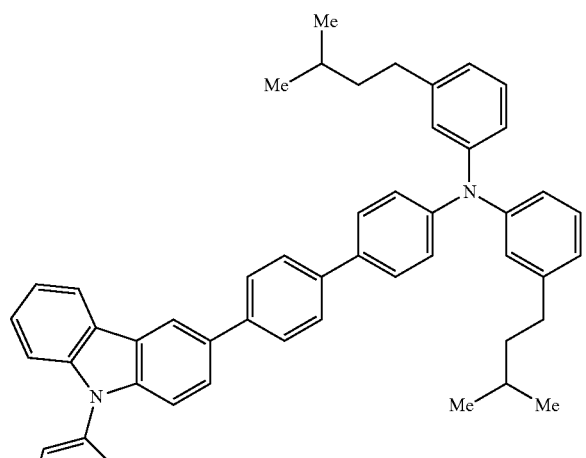

2-13
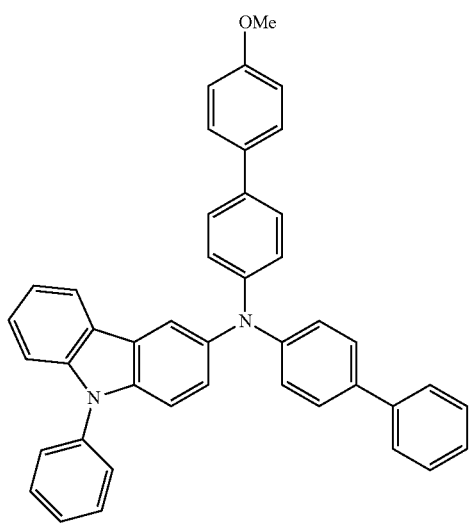
2-14
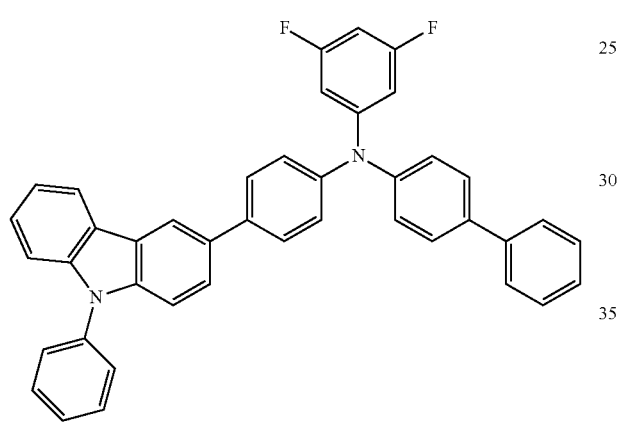
2-15
2-16
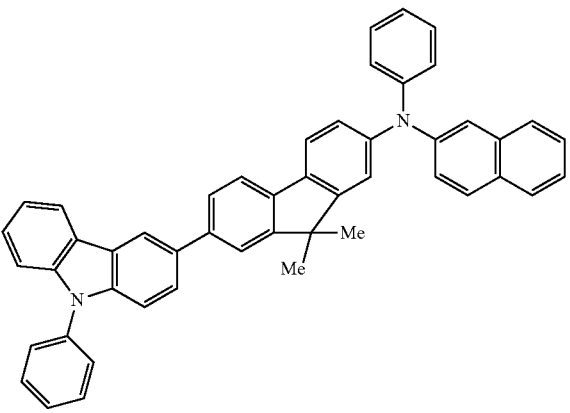
2-17
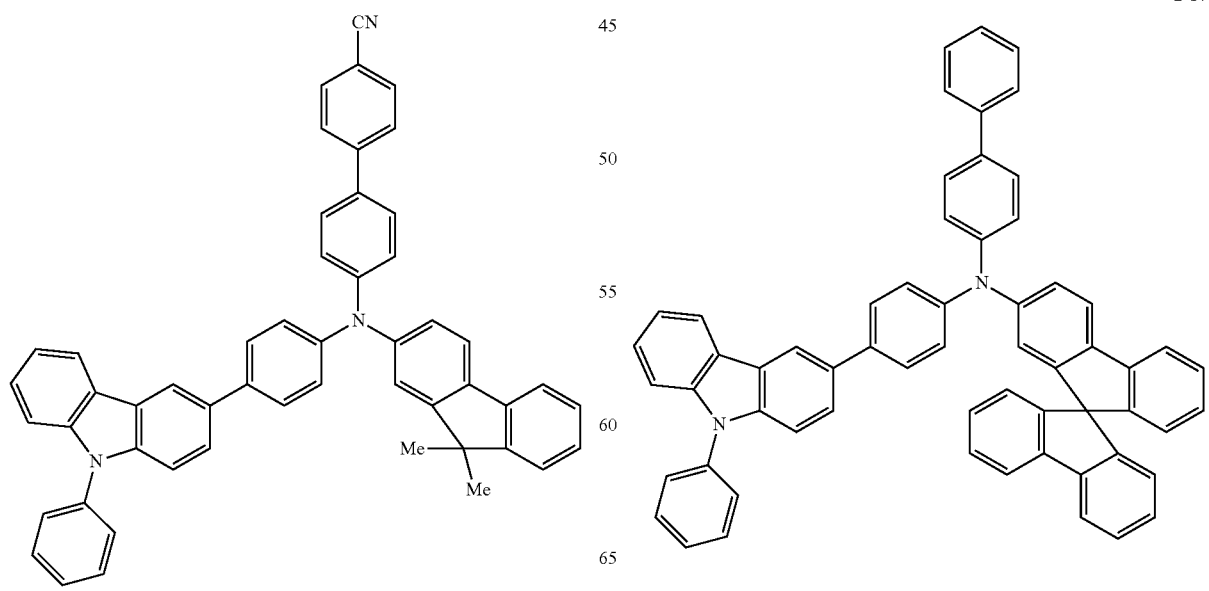

-continued 2-18

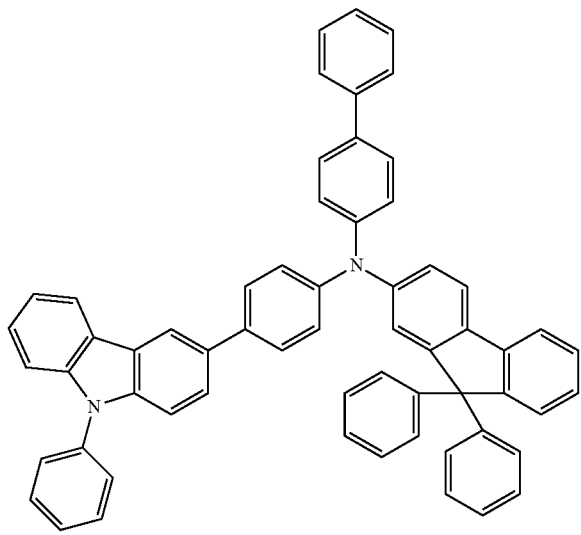

2-19

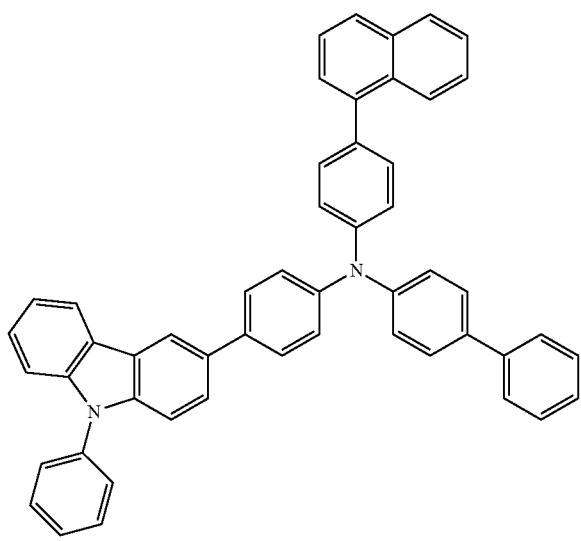

-continued 2-20

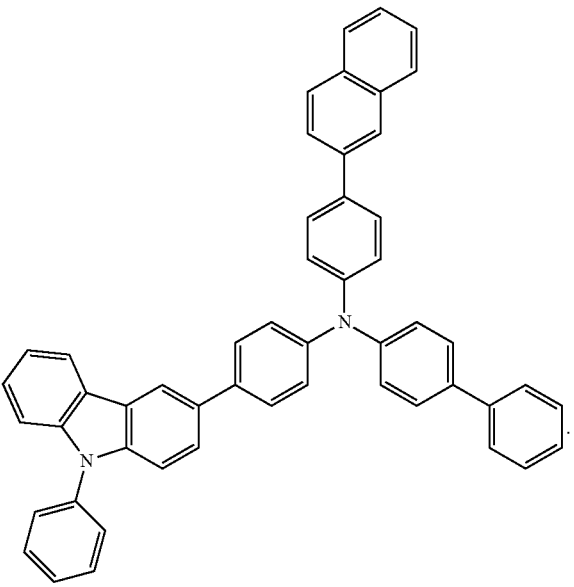

10. The organic light emitting device as claimed in claim 1, wherein $Ar_6$ and $Ar_7$ in Formula 3 are each independently a substituted phenyl group, a substituted or unsubstituted biphenyl group, a substituted or unsubstituted naphthyl group, a substituted or unsubstituted dibenzofuran group, or a substituted or unsubstituted dibenzothiophene group, provided that, in $Ar_6$ and $Ar_7$, a substituent of the substituted phenyl group, the substituted biphenyl group, the substituted naphthyl group, the substituted dibenzofuran group, and the substituted dibenzothiophene group does not include an amino group.

11. The organic light emitting device as claimed in claim 1, wherein, in Formula 3:

e is an integer of 1 to 5, and $R_5$ in Formula 3 is a substituted or unsubstituted phenyl group, a substituted or unsubstituted biphenyl group, a substituted or unsubstituted naphthyl group, a substituted or unsubstituted fluorenyl group, a substituted or unsubstituted dibenzofuran group, or a substituted or unsubstituted benzo[def]carbazole group, provided that, in $R_5$, a substituent of the substituted phenyl group, the substituted biphenyl group, the substituted naphthyl group, the substituted fluorenyl group, the substituted dibenzofuran group, and the substituted benzo[def]carbazole group does not include an amino group.

12. The organic light emitting device as claimed in claim 1, wherein the second hole transport material represented by Formula 3 comprises one of the following Compounds 3-1 to 3-20:

95 96
3-1
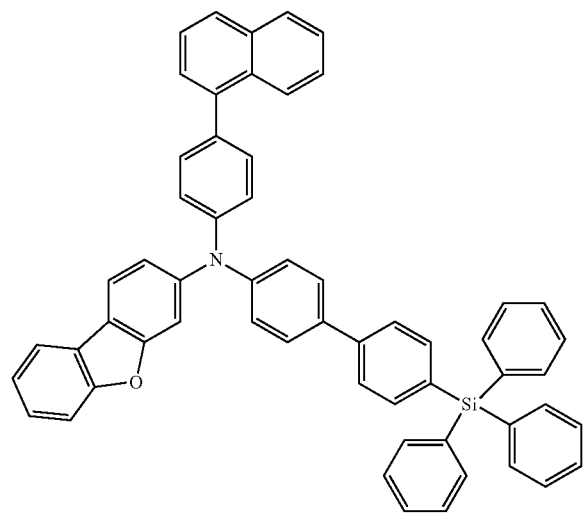
3-2
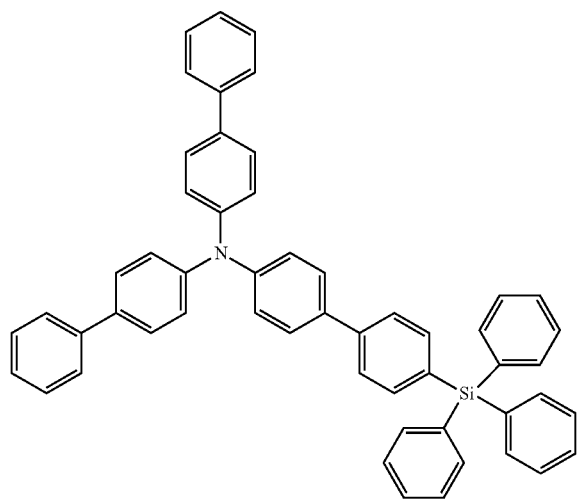
3-3
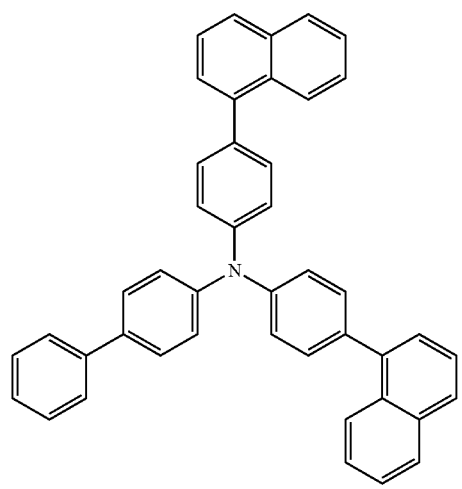
3-4
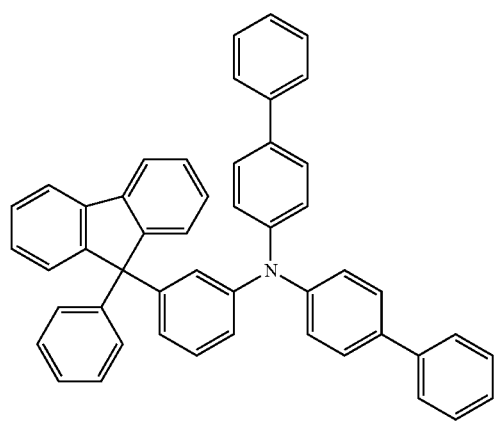
3-5
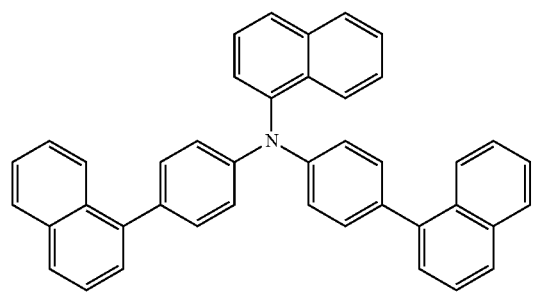
3-6
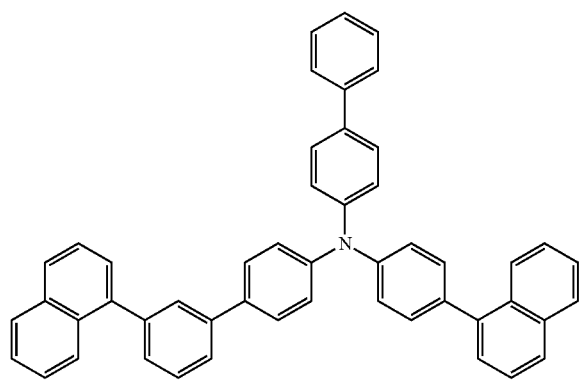

-continued
3-7
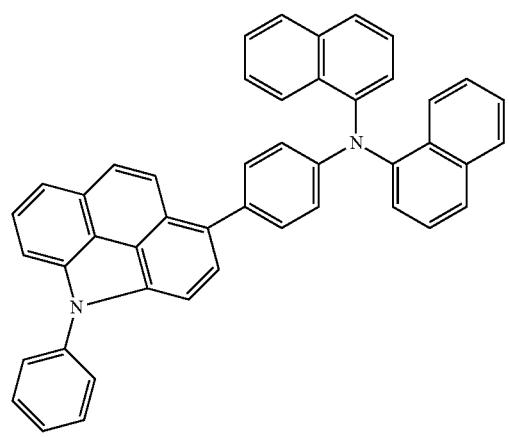
3-8
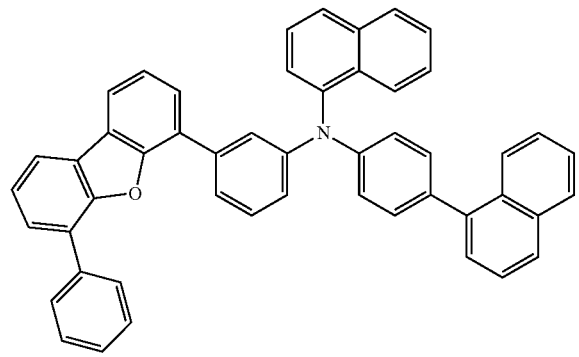
3-9
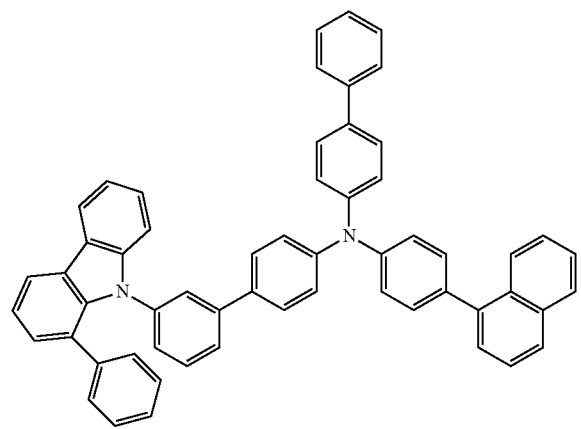
3-10
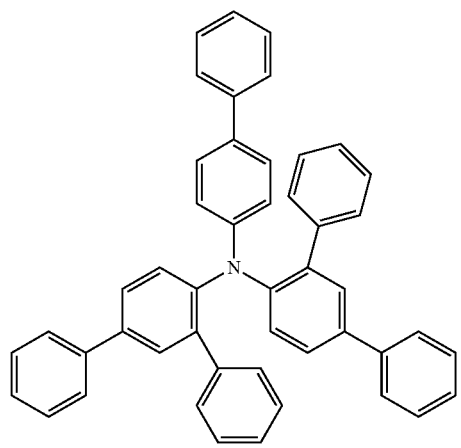
3-11
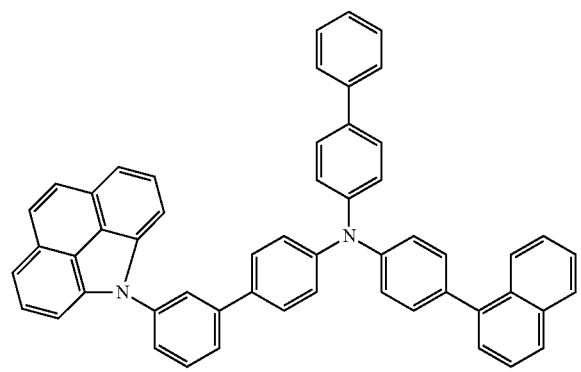
3-12
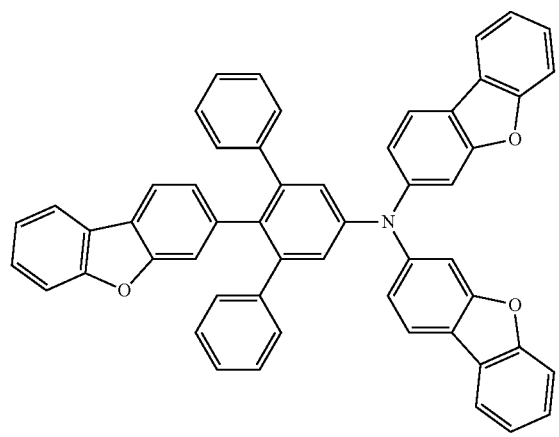

-continued
3-13
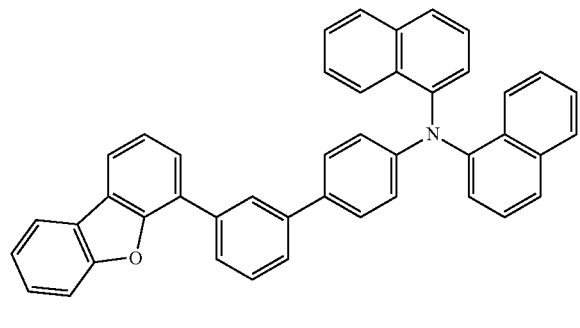
3-14
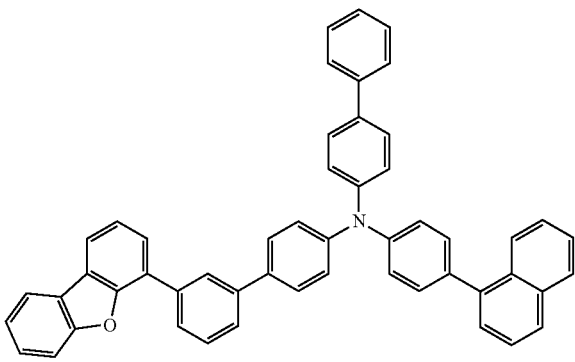
3-15
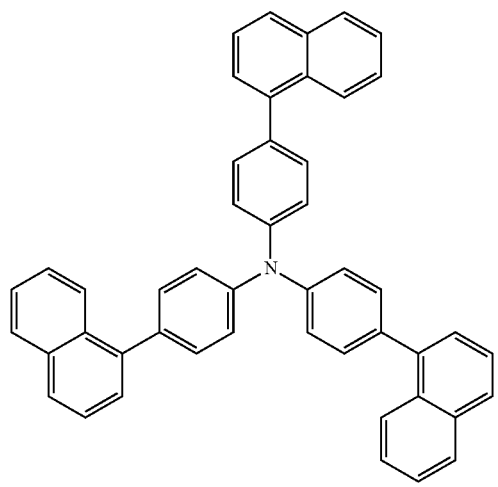
3-16
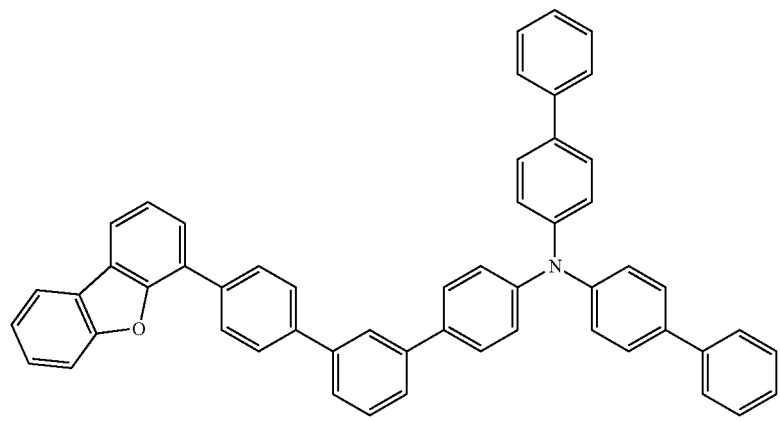

-continued 3-17

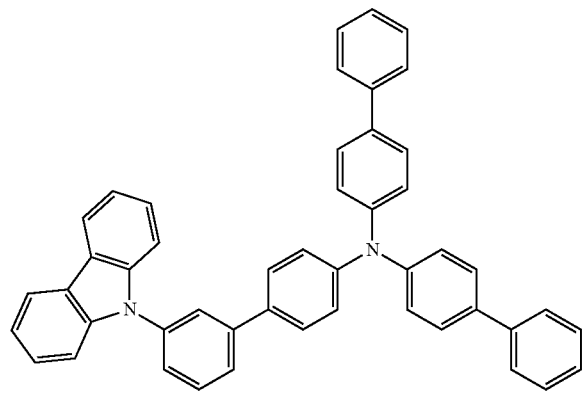

3-18

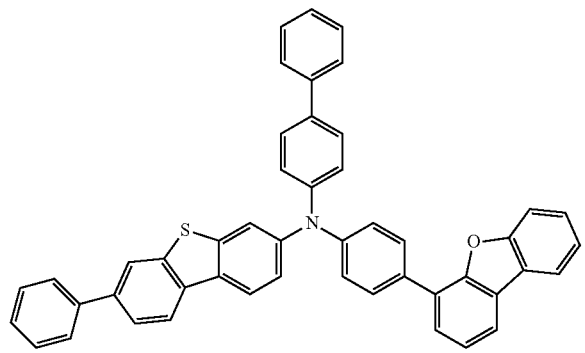

3-19

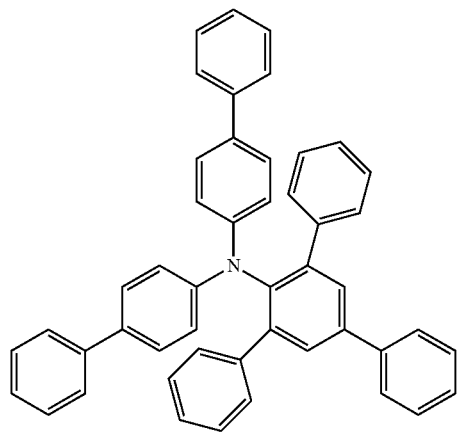

3-20

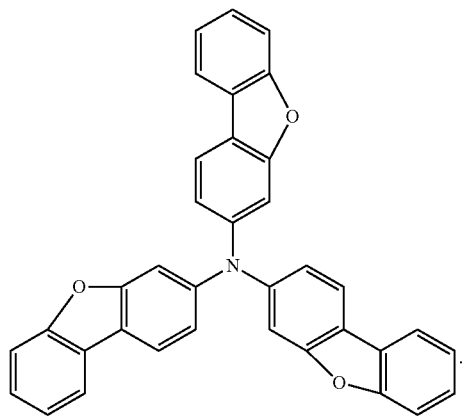

13. The organic light emitting device as claimed in claim 1, wherein $Ar_8$ in Formula 4 combines with at least one of $R_6$ or $R_{13}$ to form a ring.

14. The organic light emitting device as claimed in claim 1, wherein $R_9$ and $R_{10}$ in Formula 4 combine to form a ring that comprises X.

15. The organic light emitting device as claimed in claim 1, wherein $Ar_8$ in Formula 4 is a substituted or unsubstituted phenyl group, a substituted or unsubstituted biphenyl group, or a substituted or unsubstituted carbazole group.

16. The organic light emitting device as claimed in claim 1, wherein $R_6$ to $R_{15}$ in Formula 4 are each independently a substituted or unsubstituted phenyl group, a substituted or unsubstituted naphthyl group, substituted or unsubstituted carbazole group, a substituted or unsubstituted benzo[def]carbazole group, a substituted or unsubstituted fluorenyl group, a substituted or unsubstituted dibenzofuran group, a substituted or unsubstituted triphenylene group, a substituted or unsubstituted phenanthrene group, or a substituted or unsubstituted dibenzosilole group.

17. The organic light emitting device as claimed in claim 1, wherein the second hole transport material represented by Formula 4 comprises one of the following Compounds 4-1 to 4-28:

103 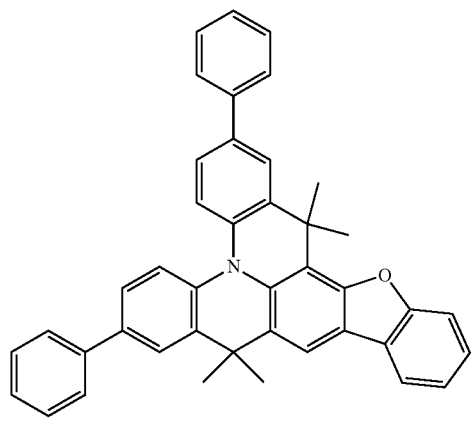
104
4-1 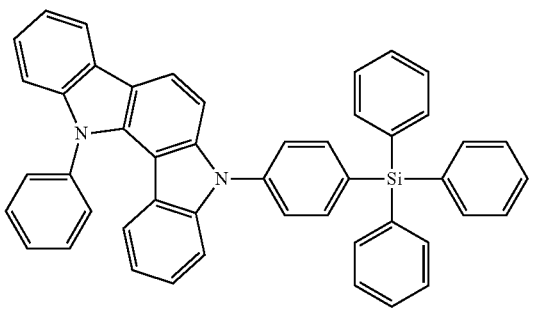 4-2
4-3 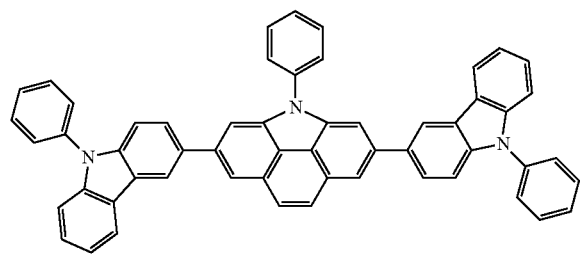 4-4
4-5 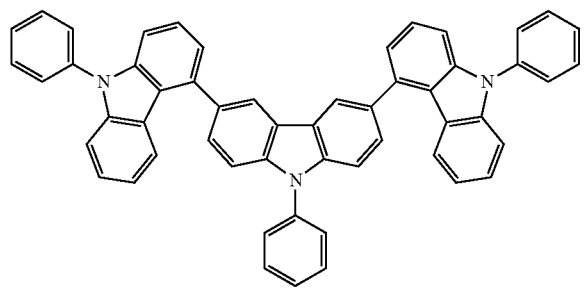 4-6 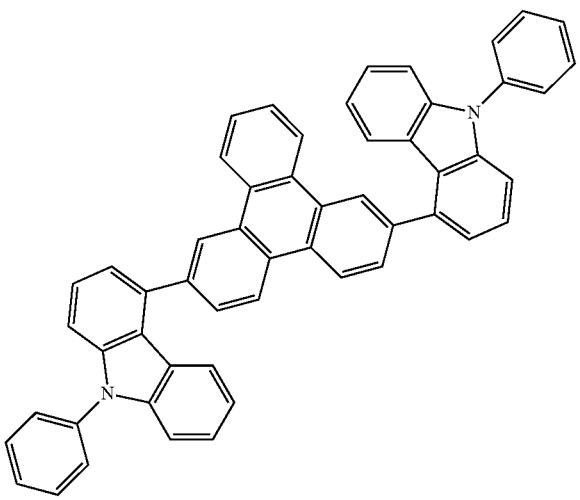
4-7 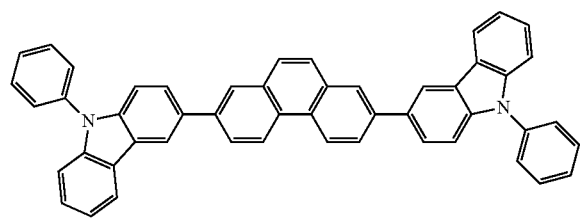 4-8 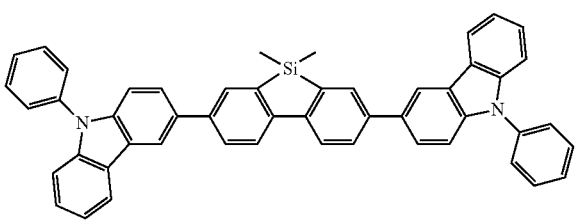

-continued
4-9
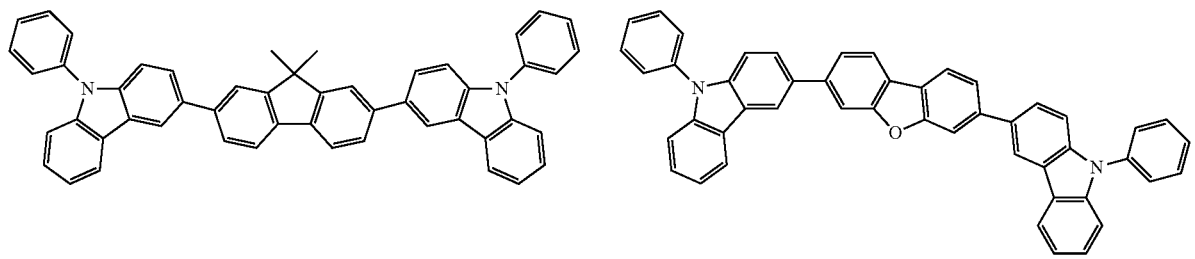
4-10
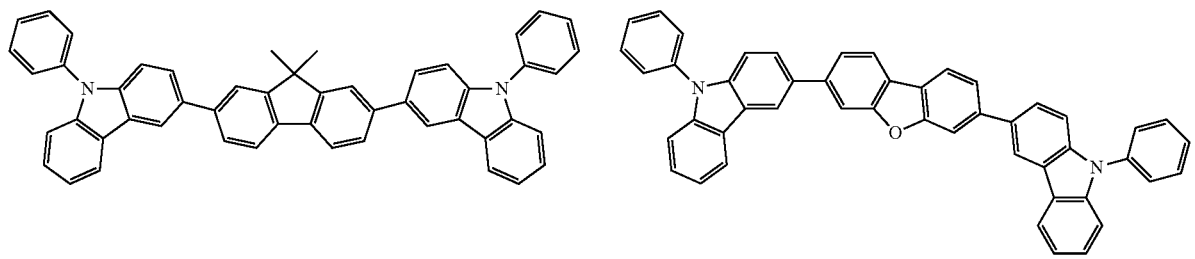
4-11
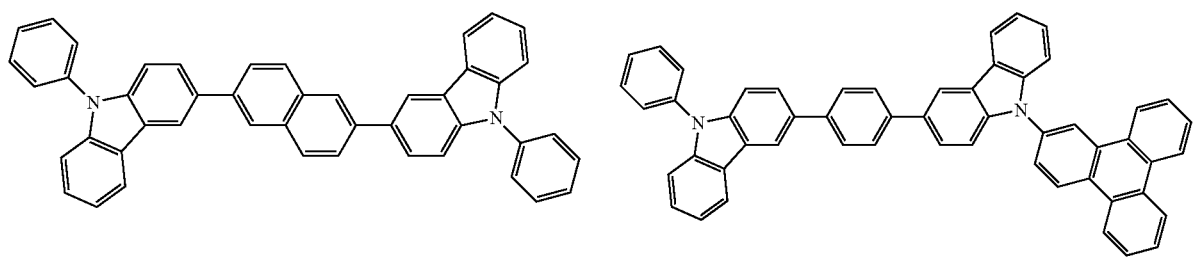
4-12
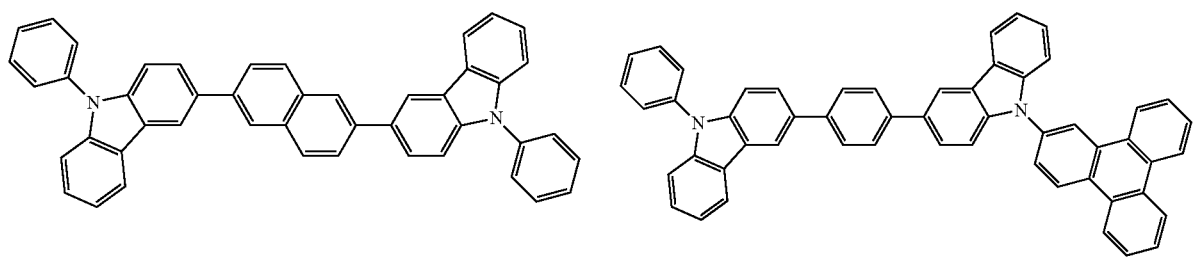
4-13
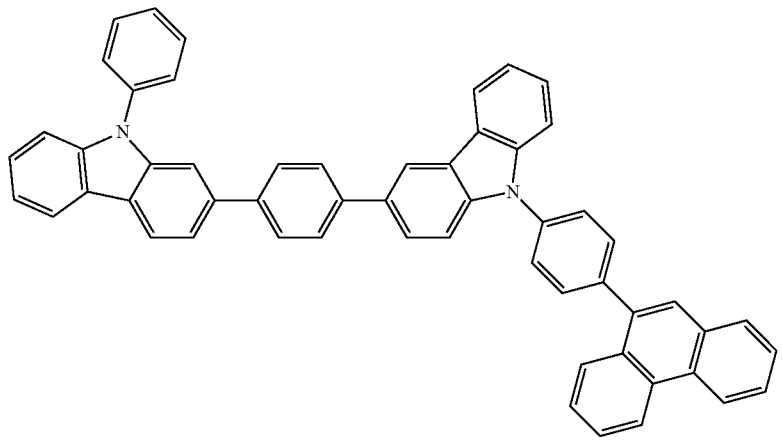
4-14
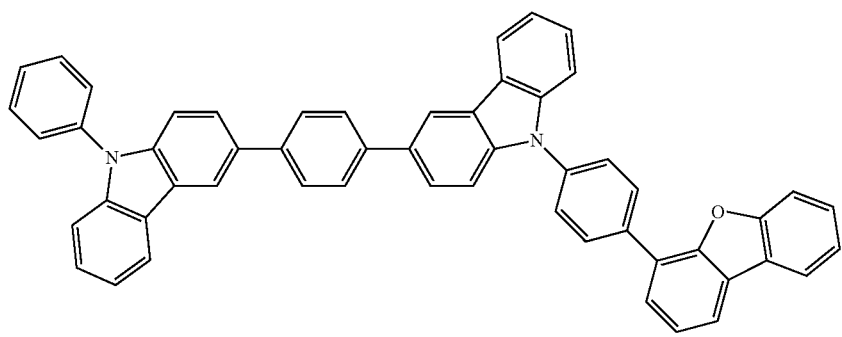

-continued
4-15
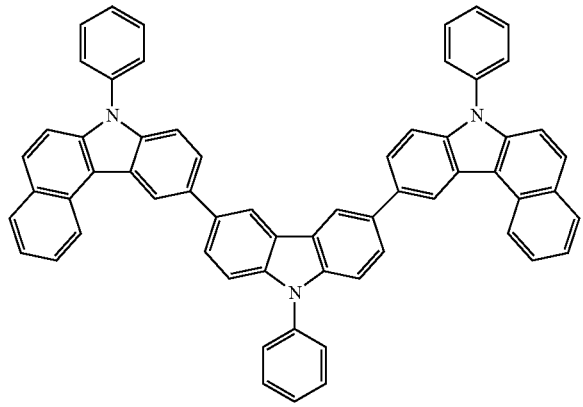
4-16
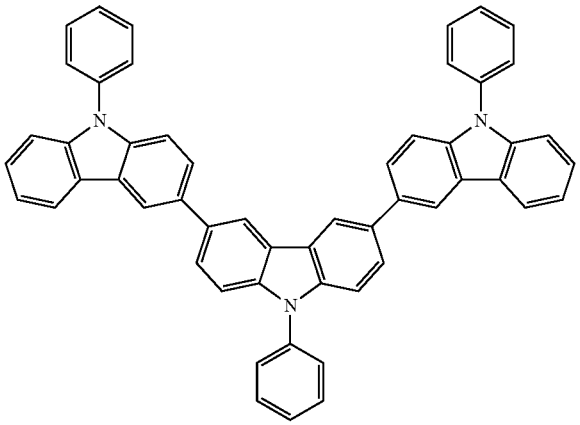
4-17
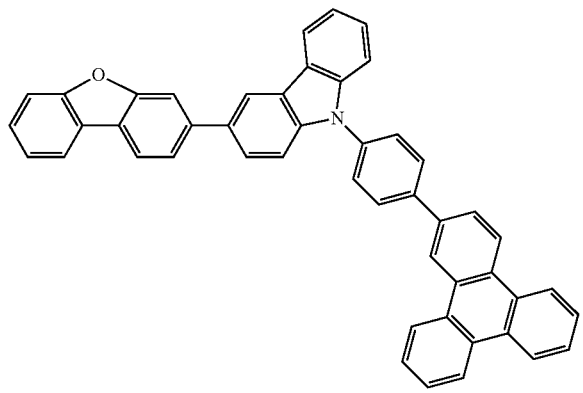
4-18
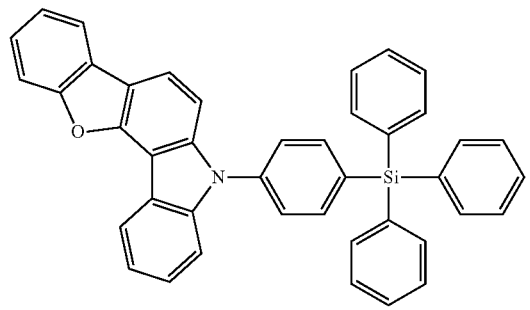
4-19
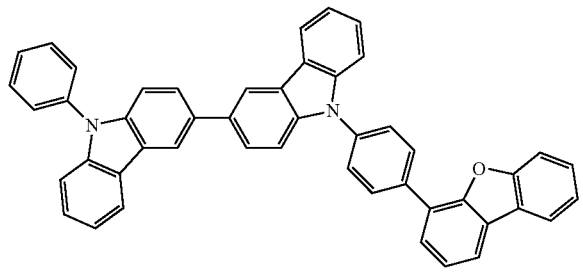
4-20
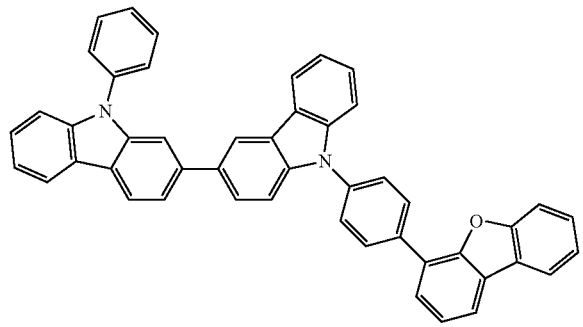
4-21
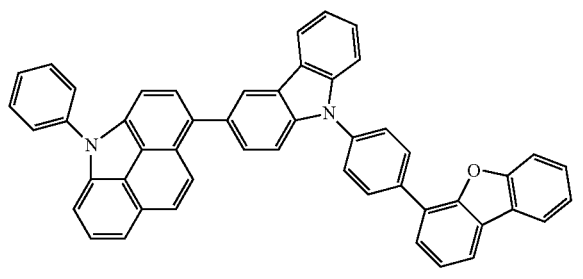
4-22
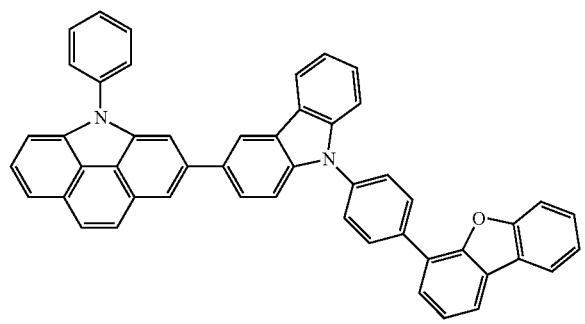

-continued
4-23
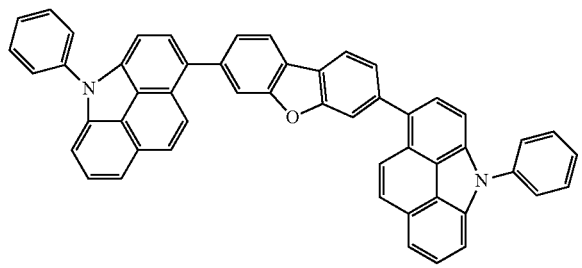
4-24
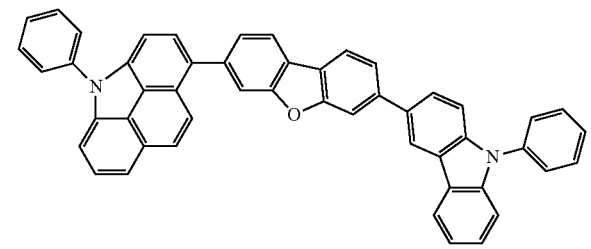
4-25
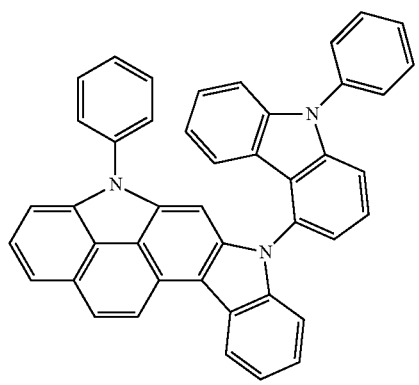
4-26
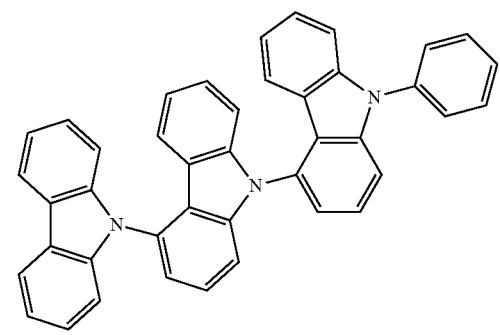
4-27
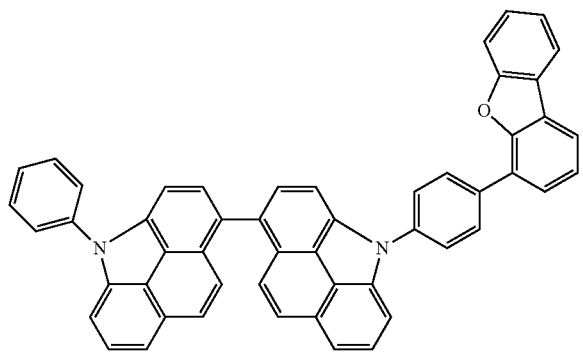
4-28
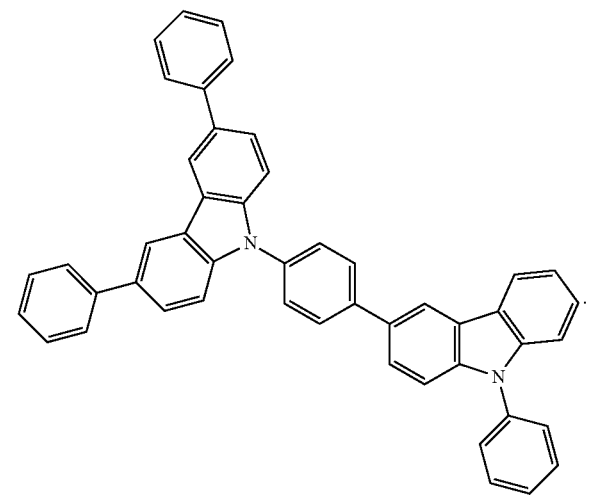
18. The organic light emitting device as claimed in claim 1, wherein the hole transport region further comprises a hole injection layer on the anode.
19. The organic light emitting device as claimed in claim 1, wherein the electron transport region comprises:
an electron transport layer; and
an electron injection layer on the electron transport layer.
* * * * *

UNITED STATES PATENT AND TRADEMARK OFFICE
CERTIFICATE OF CORRECTION

| | |
|---|---|
| PATENT NO. | : 11,925,111 B2 |
| APPLICATION NO. | : 17/495551 |
| DATED | : March 5, 2024 |
| INVENTOR(S) | : Yoshimasa Fujita et al. |

It is certified that error appears in the above-identified patent and that said Letters Patent is hereby corrected as shown below:

In the Claims

In Column 80, Line 15, in Claim 3, delete "Li" and Insert -- $L_1$ --.

In Column 102, Line 55, in Claim 16, delete "substituted" and Insert -- a substituted --.

Signed and Sealed this
Tenth Day of December, 2024

Katherine Kelly Vidal
*Director of the United States Patent and Trademark Office*